United States Patent
Saitoh et al.

(10) Patent No.: US 7,977,869 B2
(45) Date of Patent: Jul. 12, 2011

(54) ORGANIC LUMINESCENT DEVICE AND BENZO[K]FLUORANTHENE COMPOUND

(75) Inventors: Akihito Saitoh, Yokohama (JP); Masanori Muratsubaki, Hachioji (JP); Satoshi Igawa, Fujisawa (JP); Hiroki Ohrui, Kawasaki (JP); Chika Negishi, Yokosuka (JP); Masashi Hashimoto, Tokyo (JP); Takao Takiguchi, Chofu (JP); Akihiro Senoo, Kawasaki (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 336 days.

(21) Appl. No.: 12/296,574

(22) PCT Filed: Jul. 18, 2007

(86) PCT No.: PCT/JP2007/064615
§ 371 (c)(1),
(2), (4) Date: Oct. 9, 2008

(87) PCT Pub. No.: WO2008/015945
PCT Pub. Date: Feb. 7, 2008

(65) Prior Publication Data
US 2009/0278447 A1 Nov. 12, 2009

(30) Foreign Application Priority Data

Aug. 4, 2006 (JP) .............................. 2006-213606
May 1, 2007 (JP) .............................. 2007-120565

(51) Int. Cl.
*H01J 1/63* (2006.01)
*C07C 13/62* (2006.01)
*C07D 401/10* (2006.01)
(52) U.S. Cl. ........... 313/504; 585/27; 546/255; 546/165
(58) Field of Classification Search .................. 428/690; 313/504; 585/27; 546/255, 165
See application file for complete search history.

(56) References Cited

U.S. PATENT DOCUMENTS

| | | | |
|---|---|---|---|
| 6,652,997 B2 | 11/2003 | Suzuki et al. | 428/690 |
| 7,049,011 B2* | 5/2006 | Ebisawa et al. | 428/690 |
| 2004/0265632 A1* | 12/2004 | Okinaka et al. | 428/690 |
| 2005/0236977 A1 | 10/2005 | Yamada et al. | 313/504 |
| 2006/0121312 A1 | 6/2006 | Yamada et al. | 428/690 |
| 2006/0158102 A1 | 7/2006 | Kawamura et al. | 313/504 |
| 2007/0024341 A1 | 2/2007 | Muggler et al. | 327/520 |

FOREIGN PATENT DOCUMENTS

| | | |
|---|---|---|
| JP | 11-012205 | 1/1999 |
| JP | 2000-178212 | 6/2000 |
| JP | 2002-025776 | 1/2002 |
| JP | 2004-002351 | 1/2004 |
| JP | 2005-068087 | 3/2005 |
| JP | 2005068087 A * | 3/2005 |
| JP | 2007-291061 | 11/2007 |
| WO | WO 2005/090365 A1 | 9/2005 |
| WO | WO 2007/100010 A1 | 9/2007 |
| WO | WO 2007-114038 A1 | 10/2007 |

OTHER PUBLICATIONS

Machine English translation JP 2005-068087 A. Nov. 4, 2010.*
International Preliminary Report on Patentability issued Feb. 10, 2009 in International Application PCT/JP 2007/065328.

* cited by examiner

*Primary Examiner* — Angela Ortiz
*Assistant Examiner* — J. L. Yang
(74) *Attorney, Agent, or Firm* — Fitzpatrick, Cella, Harper & Scinto

(57) ABSTRACT

An organic luminescent device having organic-compound layers is provided which takes on luminous hues with very good purity and has optical power with high efficiency, high luminance and a long life. At least one of the organic-compound layers contains a benzo[k]fluoranthene compound represented by the following general formula (1):

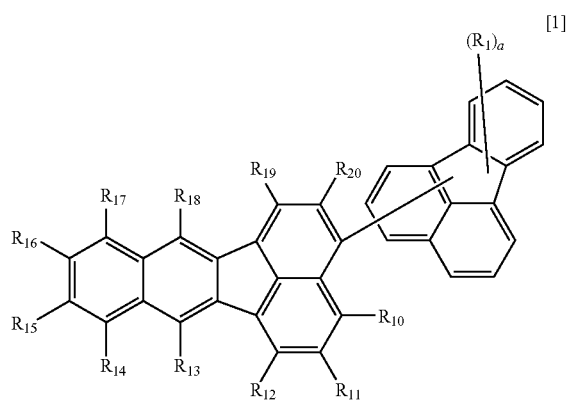

[1]

wherein $R_1$ is a group selected from the group consisting of alkyl, aralkyl and a heterocyclic group which may be substituted, and $R_1$'s may be the same or different; $R_{10}$ to $R_{20}$ are each independently a group selected from the group consisting of hydrogen, halogen, alkyl, aralkyl, phenyl, a condensed bicyclic aromatic group and a heterocyclic group which may be substituted; and a is an integer of 0 or more to 9 or less.

13 Claims, 5 Drawing Sheets

ORGANIC LUMINESCENT DEVICE AND BENZO[K]FLUORANTHENE COMPOUND

TECHNICAL FIELD

This invention relates to an organic luminescent device (organic EL(electroluminescent) device) using a benzo[k]fluoranthene compound, and relates to the benzo[k]fluoranthene compound.

BACKGROUND ART

Organic luminescent devices are devices in which a thin film containing a fluorescent organic compound is held between an anode and a cathode, electrons and holes are injected from each electrode to produce excitons of the fluorescent organic compound, and the light is utilized that is emitted when the excitons return to the ground state.

Recent progress seen in such organic luminescent devices is noticeable, and they have characteristics capable of realizing luminescent devices which can achieving high luminance at a low applied voltage, a variety of luminescent wavelengths and high-speed response, and are thin and light-weight. Thus, there is a possibility that they are applied to a wide variety of uses. However, they still have many problems in respect of durability, such as changes over time caused by long-time service and deterioration due to oxygen-containing environmental gases and humidity. Considering that they are applied to full-color displays, blue, green and red light emissions with much longer lifetime, much higher conversion efficiency and much higher color purity are required under existing circumstances. Accordingly, various proposals have been made.

Japanese Patent Application Laid-Open No. 2002-025776, Japanese Patent Application Laid-Open No. H11-012205 and Japanese Patent Application Laid-Open No. 2000-178212 may be cited as patent documents relating to the compound concerning the present invention. However, in these documents there is no disclosure concerning the present invention.

DISCLOSURE OF THE INVENTION

An object of the present invention is to provide a compound for an organic luminescent device which takes on luminous hues with a very high degree of purity and has optical power with high efficiency, high luminance and a long life, and to provide an organic luminescent device using such a compound.

A further object of the present invention is to provide an organic luminescent device which can be fabricated with ease and can be manufactured at relatively low costs.

The present inventors have conducted extensive research in order to solve the problems stated above. As a result, they have accomplished the present invention.

The present invention provides an organic luminescent device constituted of an anode and a cathode at least one of which is transparent or semitransparent, and a layer containing an organic compound, held between a pair of electrodes consisting of the anode and the cathode, wherein;

the layer containing an organic compound contains a benzo[k]fluoranthene compound represented by the following general formula (1).

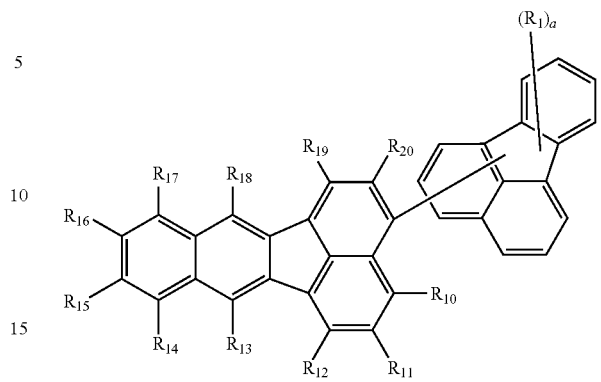

In the general formula (1), $R_1$ is a group selected from the group consisting of a substituted or unsubstituted alkyl group, a substituted or unsubstituted aralkyl group and a substituted or unsubstituted heterocyclic ring group, and $R_1$'s may be the same or different;

$R_{10}$ to $R_{20}$ are each independently a group selected from the group consisting of a hydrogen atom, a halogen atom, a substituted or unsubstituted alkyl group, a substituted or unsubstituted aralkyl group, a substituted or unsubstituted phenyl group, a substituted or unsubstituted condensed bicyclic aromatic group and a substituted or unsubstituted heterocyclic group; and a is an integer of 0 or more and 9 or less.

The present invention also provides a benzo[k]fluoranthene compound represented by the following general formula (3).

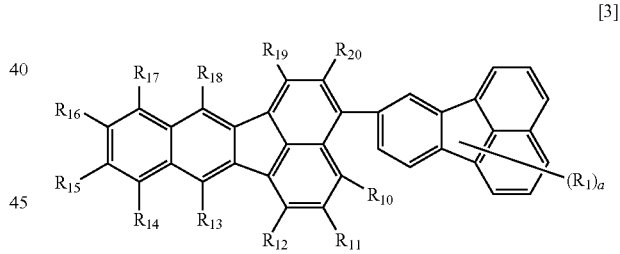

In the general formula (3), $R_1$ is a group selected from the group consisting of a substituted or unsubstituted alkyl group, a substituted or unsubstituted aralkyl group and a substituted or unsubstituted heterocyclic group, and $R_1$'s may be the same or different;

$R_{10}$ to $R_{20}$ are each independently a group selected from the group consisting of a hydrogen atom, a halogen atom, a substituted or unsubstituted alkyl group, a substituted or unsubstituted aralkyl group, a substituted or unsubstituted alkoxyl group, a substituted or unsubstituted phenyl group, a substituted or unsubstituted condensed bicyclic aromatic group and a substituted or unsubstituted heterocyclic group; and a is an integer of 0 or more and 9 or less.

The organic luminescent device and compound of the present invention affords highly efficient light emission at a low applied voltage, and also has high thermal stability and ensure superior durability.

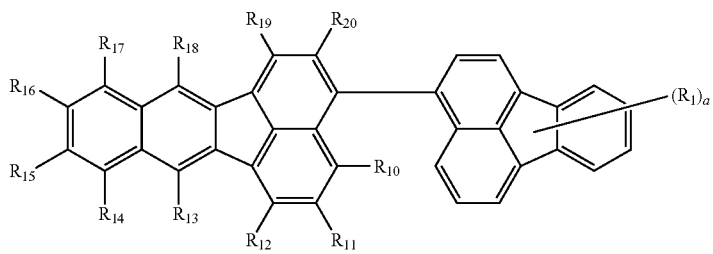

[2]

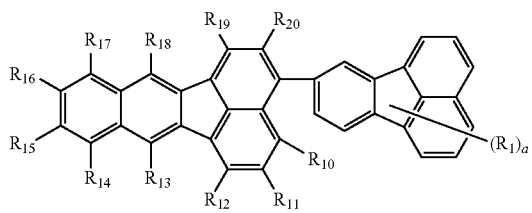

[3]

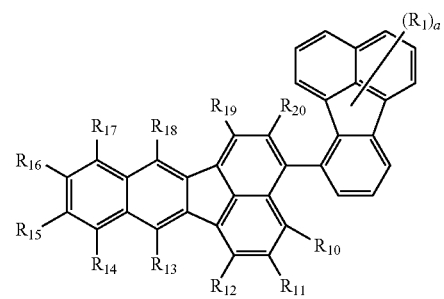

(11)

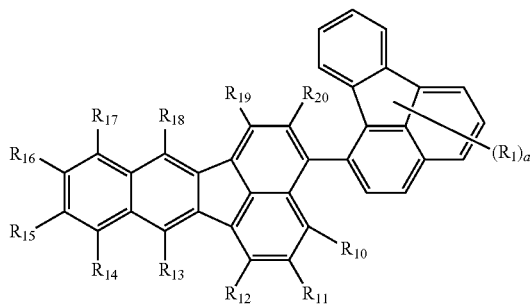

(12)

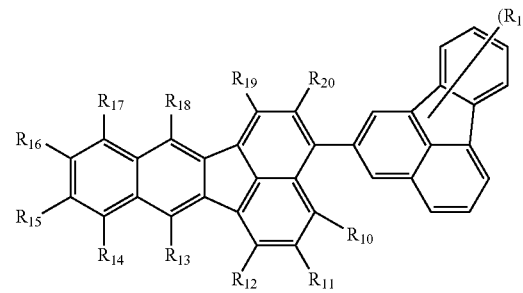

(13)

Figure 2:
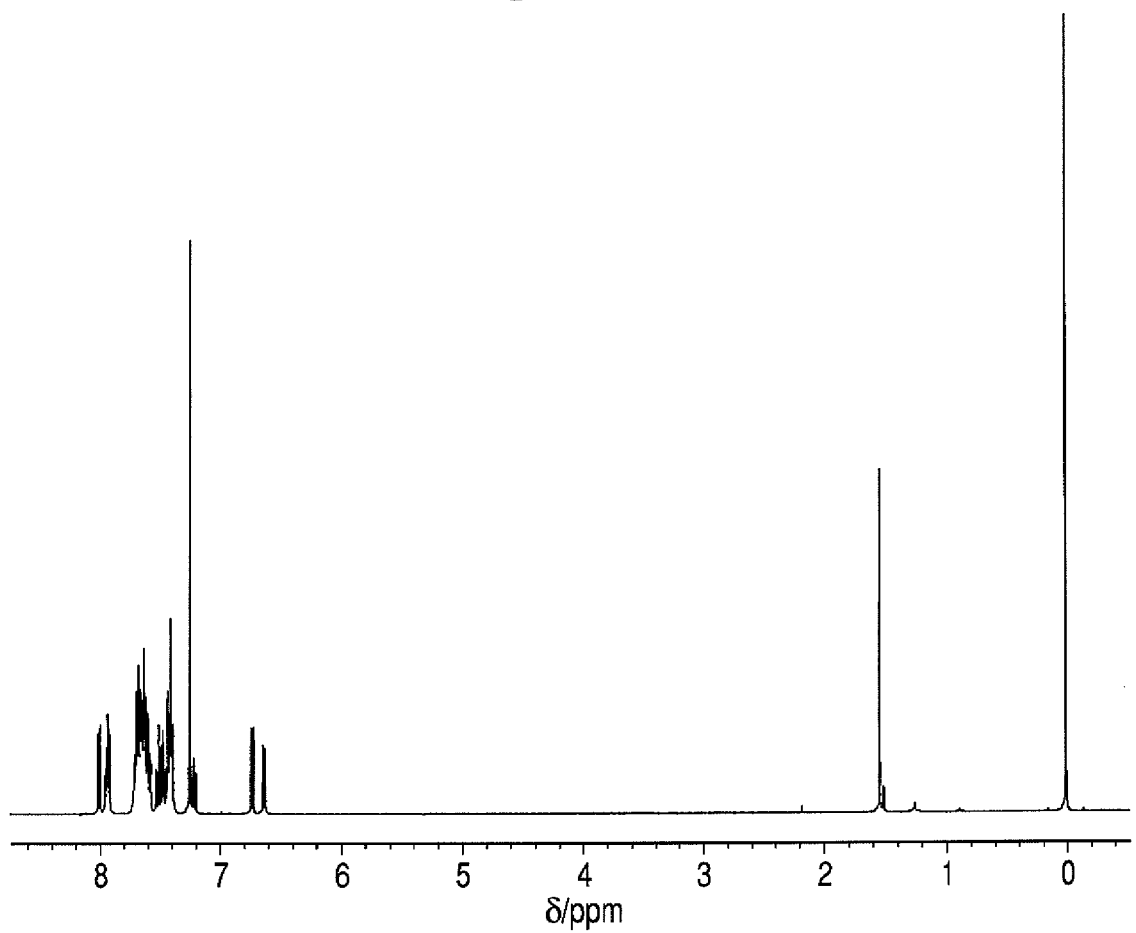

FIG. 2 is a graph showing a $^1$H-NMR (CDCl$_3$) spectrum of Exemplary Compound 101.

Figure 3:
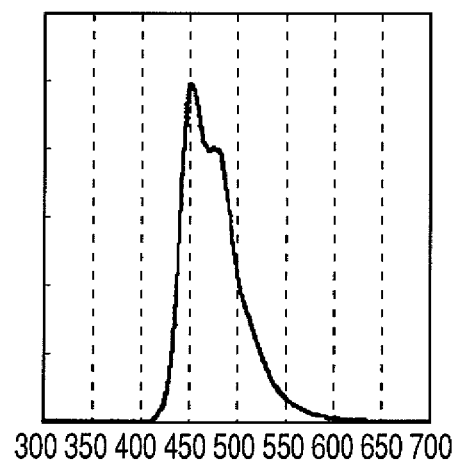

FIG. 3 is a graph showing a PL spectrum (excitation wavelength: 420 nm) of a toluene solution containing Exemplary Compound 101 in a concentration of $1 \times 10^{-5}$ mol/l.

Figure 4:
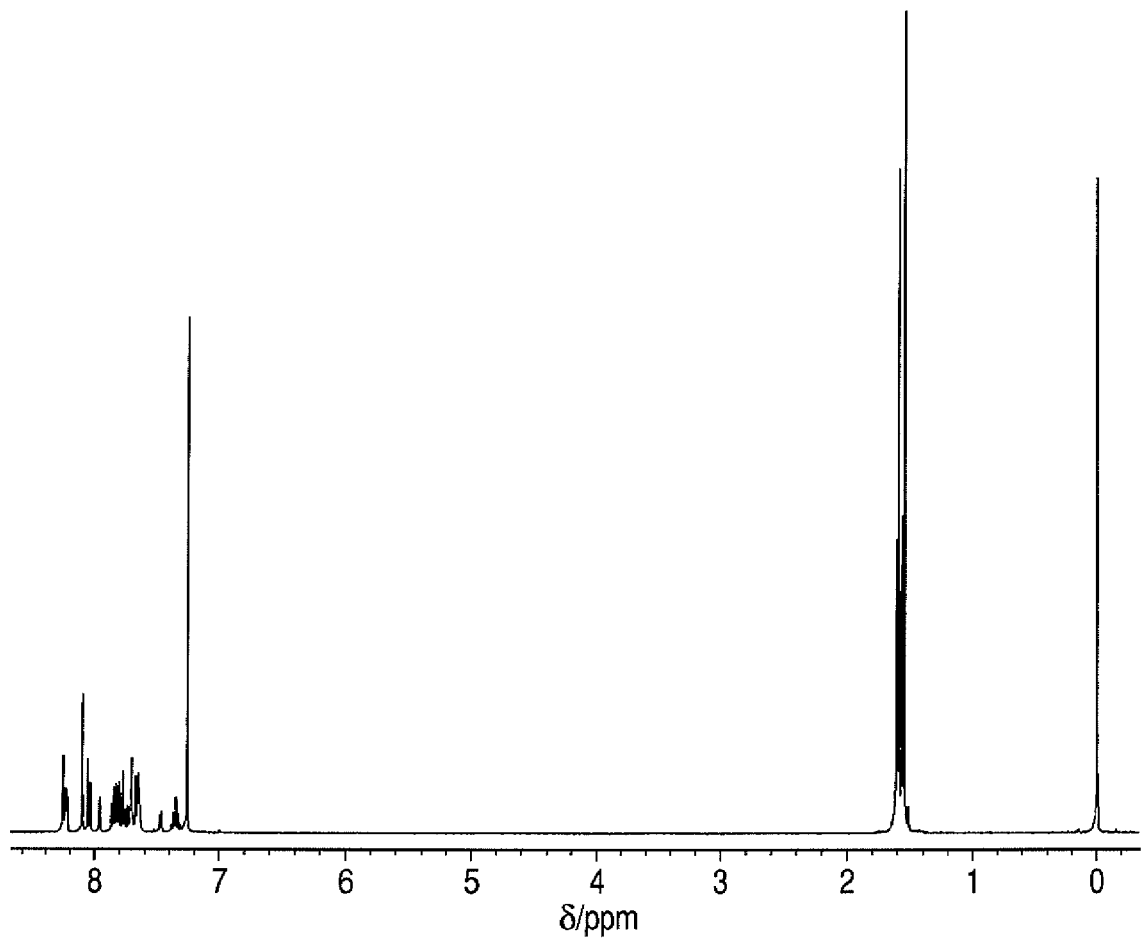

FIG. 4 is a graph showing a $^1$H-NMR (CDCl$_3$) spectrum of Exemplary Compound H2-3.

Figure 5:
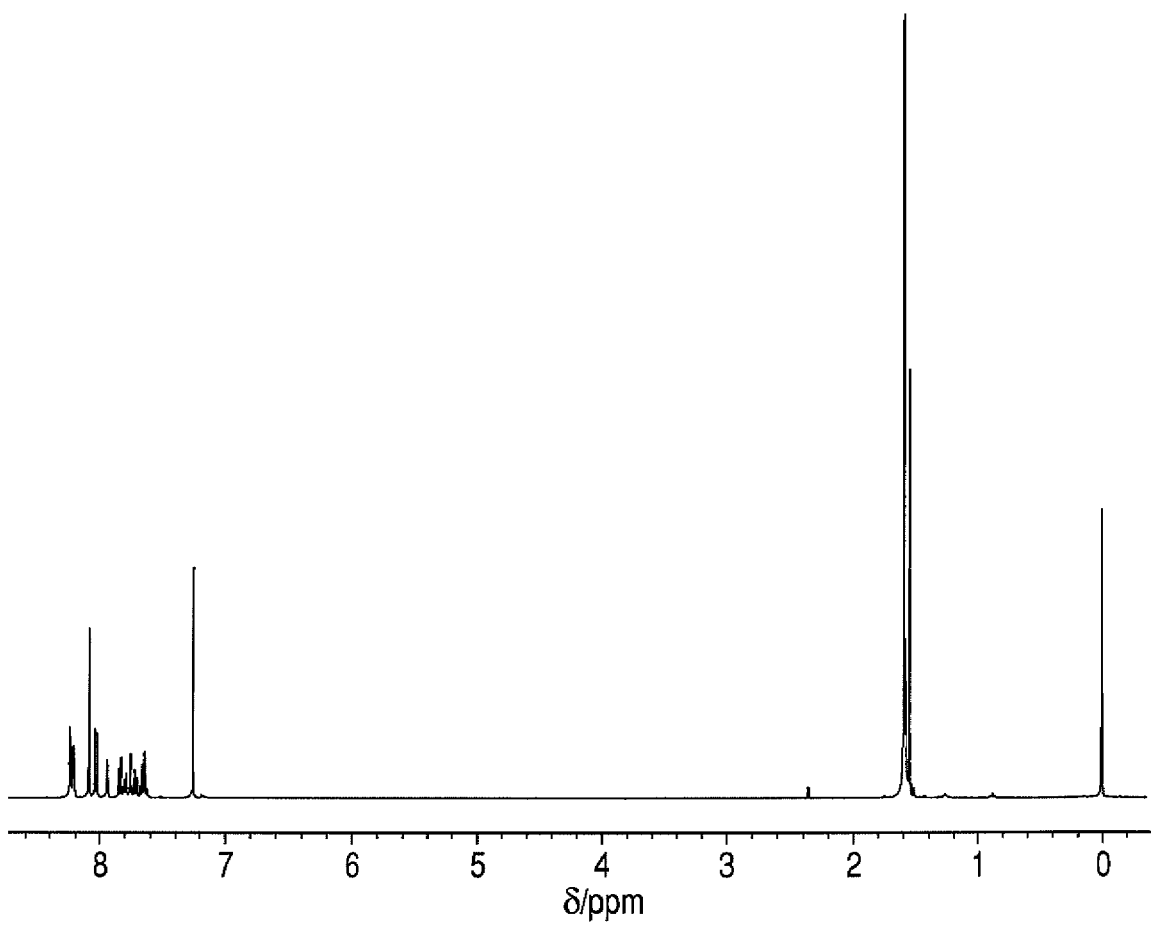

FIG. 5 is a graph showing a $^1$H-NMR (CDCl$_3$) spectrum of Exemplary Compound H4-2.

Figure 6:
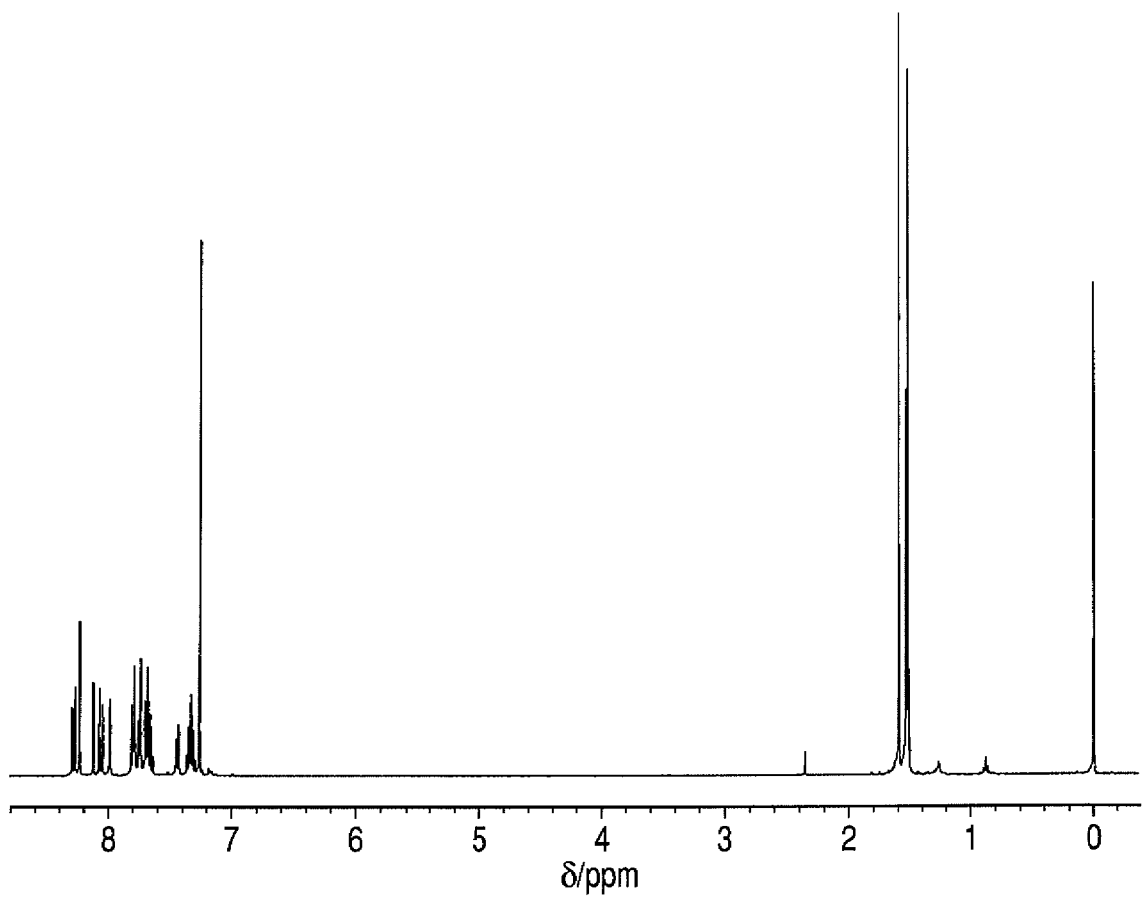

FIG. 6 is a graph showing a $^1$H-NMR (CDCl$_3$) spectrum of Exemplary Compound H9-1.

Figure 7:
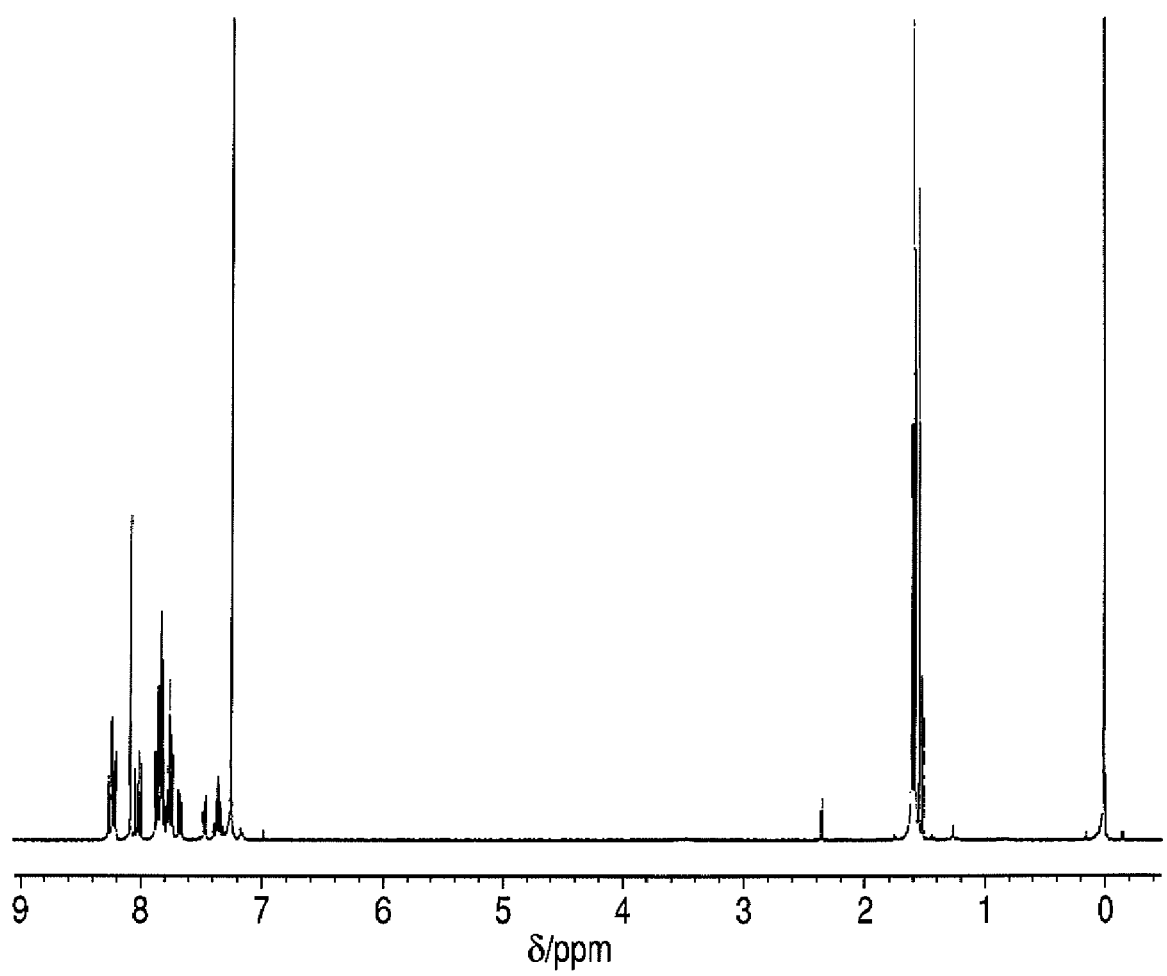

FIG. 7 is a graph showing a $^1$H-NMR (CDCl$_3$) spectrum of Exemplary Compound H14-3.

BEST MODE FOR CARRYING OUT THE INVENTION

The present invention is described below in detail.

In the first place, the benzo[k]fluoranthene compound used in the organic luminescent device of the present invention is described.

The benzo[k]fluoranthene compound of the present invention is represented by the general formula (1). This compound can be used without regard to the substitution position of the fluoranthene ring at which the fluoranthene ring is bonded to the 3-position of the benzo[k]fluoranthene ring, and is specifically represented by any one of the following general formulas (2) and (3) and the general formulas (11) to (13).

In the general formulas (2) and (3) and (11) to (13), $R_1$, $R_{10}$ to $R_{20}$ and a are as defined in the general formula (1).

Where the substituent on the benzo[k]fluoranthene ring is a substituted phenyl group, a compound having the substituent at the ortho-position is particularly preferred in order to control concentration quenching due to cohesion. This is because the compound has a structure in which the phenyl rises from the plane of the benzofluoranthene ring in virtue of steric repulsion attributable to the substituent at the ortho-position.

The benzo[k]fluoranthene compound used in the present invention can be used as a material for organic luminescent devices. In particular, when used for a light-emitting layer, it can be used alone in the light-emitting layer, and can be used as a dopant (guest) material or a host material. Thus, a device can be obtained which emits light at high efficiency, keeps high luminance over a long period of time and is reduced in deterioration due to electrification.

Where the light-emitting layer is formed of carrier-transporting host and guest materials, the main course that comes up with light emission consists of the following several steps.

1. Transport of electrons and holes in the light-emitting layer.
2. Formation of excitons of the host.
3. Transmission of excitation energy between host molecules.
4. Movement of excitation energy from the host to the guest.

The desired energy movement and light emission in the respective steps take place through various deactivation processes and competitions.

In order to improve luminous efficiency of EL devices, it is needless to say that a luminescent center material itself has a large light emission quantum yield. However, it is also a great question how efficiently the host-to-host or host-to-guest energy movement can be made. In addition, the cause of deterioration in light emission due to electrification is unclear at present, is presumed to correlate with the luminescent center material itself or environmental changes caused by its peripheral molecules.

Accordingly, the present inventors have made various studies, and have discovered that a device using a compound in which fluoranthene and benzofluoranthene are combined with each other through one single bond especially as the host or guest of the light-emitting layer, emits blue light at high efficiency, keeps high luminance over a long period of time and is reduced in deterioration due to electrification.

The molecular orbital has been calculated for 3-(8-fluoranthenyl)-benzo[k]fluoranthene which is a compound having the basic skeleton of the benzo[k]fluoranthene compound used in the present invention. As a result, it has been indicated that the LUMO orbital spreads from the fluoranthene to the benzofluoranthene and the HOMO orbital is localized at the benzofluoranthene. On account of this calculation, the present inventors conceived that it is possible to improve luminescent colors in virtue of the electron trapping performance and CT (charge transfer) performance attributable to the LUMO spreading from the fluoranthene to the benzofluoranthene.

Further, in order to control the concentration quenching due to the mutual action of intermolecular condensed-ring aromatic groups, it is preferable for improving a quantum yield that steric hindrance groups such as tert-butyl groups are introduced into the condensed-ring aromatic groups.

The compound of the present invention can be used without regard to the substitution position of the fluoranthene ring at which the fluoranthene is bonded to the 3-position of the benzo[k]fluoranthene ring. Taking into account steric hindrance due to the peri-position, an effect on rotation restraint and further the process of synthesizing the compound, it is preferable that the fluoranthene ring is substituted at its 3-position.

In the above general formulas (1) to (3) and general formulas (11) to (13), the hydrogen substituents may be replaced with heavy hydrogen.

The substituted or unsubstituted alkyl group includes, but is not limited to, e.g., the following:

A methyl group, a methyl-d1 group, a methyl-d3 group, an ethyl group, an ethyl-d5 group, a n-propyl group, a n-butyl group, a n-pentyl group, a n-hexyl group, a n-heptyl group, a n-octyl group, a n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, an iodoethyl group, a hydroxymethyl group, a hydroxyethyl group, a cyclopropyl group, a cyclobutyl group, a cyclopentyl group, a cyclohexyl group, a cyclopentyl methyl group, a cyclohexyl methyl group, a cyclohexyl ethyl group, a 4-fluorocyclohexyl group, a norbornyl group and an adamantyl group.

The substituted or unsubstituted aralkyl group includes, but is not limited to, e.g., the following:

A benzyl group, a 2-phenylethyl group, a 2-phenylisopropyl group, a 1-naphthylmethyl group, a 2-naphthylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group and a 4-bromobenzyl group.

The substituted or unsubstituted phenyl group includes, but is not limited to, e.g., the following:

A phenyl group, a phenyl-d5 group, a 2-methylphenyl group, a 3-methylphenyl group, a 4-methylphenyl group, a 4-methoxyphenyl group, a 4-ethylphenyl group, a 2-fluorophenyl group, a 3-fluorophenyl group, a 4-fluorophenyl group, a 4-trifluoromethylphenyl group, a 3,5-dimethylphenyl group, a 2,6-dimethylphenyl group, a 2,6-diethylphenyl group, a mesityl group, a 3-iso-propylphenyl group, a 3-tert-butylphenyl group, a 4-iso-propylphenyl group, a 4-tert-butylphenyl group, a 4-cyanophenyl group, a 4-(di-p-tolylamino)phenyl group, a biphenyl group and a terphenyl group.

The substituted or unsubstituted condensed bicyclic aromatic group includes, but is not limited to, a naphthyl group, an azulene group and a heptalene group.

The substituted or unsubstituted heterocyclic group include, but is not limited to, e.g., the following:

A pyrrolyl group, a pyridyl group, a pyridyl-d5 group, a bipyridyl group, a methylpyridyl group, a pyrimidinyl group, a pyrazinyl group, a pyridazinyl group, a terpyrrolyl group, a thienyl group, a thienyl-d4 group, a terthienyl group, a propylthienyl group, a benzothienyl group, a dibenzothienyl group, a dibenzothienyl-d7 group, a furyl group, a furyl-d4 group, a benzofuryl group, a isobenzofuryl group, a dibenzofuryl group, a dibenzofuryl-d7 group, a quinolyl group, a quinolyl-d6 group, an isoquinolyl group, a quinoxalinyl group, a naphthyridinyl group, a quinazolinyl group, a phenanthridinyl group, an indolizinyl group, a phenazinyl group, a carbazolyl group, an oxazolyl group, an oxadiazolyl group, a thiazolyl group, a thiadiazolyl group, an acridinyl group and a phenazinyl group.

The halogen atom includes a fluorine atom, a chlorine atom, a bromine atom and an iodine atom.

A substituent(s) the above substituents may each further have include(s), but is (are) not limited to, e.g., the following:

Alkyl groups such as a methyl group, an ethyl group and a propyl group, aryl groups such as a phenyl group and a biphenyl group, heterocyclic groups such as a thienyl group, a pyrrolyl group and a pyridyl group, amino groups such as a dimethylamino group, a diethylamino group, a dibenzylamino group, a diphenylamino group, a ditolylamino group and a dianisolylamino group, and the substituted or unsubstituted alkyl groups listed above; substituted or unsubstituted alkoxyl groups, alkyloxyl groups having an aralkyl group, aralkyloxyl groups, substituted or unsubstituted aryl groups, and aryloxyl groups having a heterocyclic group, as exemplified by a methoxyl group, an ethoxyl group, a propoxyl group, a 2-ethyl-octyloxyl group, a phenoxyl group, a 4-tert-butylphenoxyl group, a benzyloxyl group and a thienyloxyl group; halogen atoms such as fluorine, chlorine, bromine and iodine; and a hydroxyl group, a cyano group, and a nitro group.

The benzo[k]fluoranthene compound used in the present invention specifically include, but is not limited to, those shown in the following tables. In the following tables, the benzo[k]fluoranthene compound used in the present invention is represented by A-B. In each of A and B, the position at which these are combined with each other is shown. More specifically, as to Exemplary Compound 101, the combination is expressed as follows:

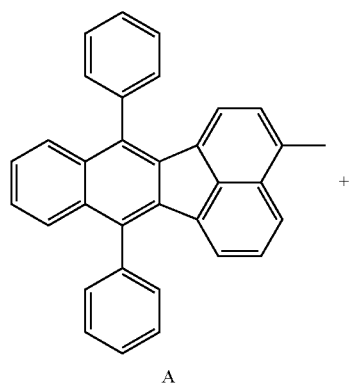

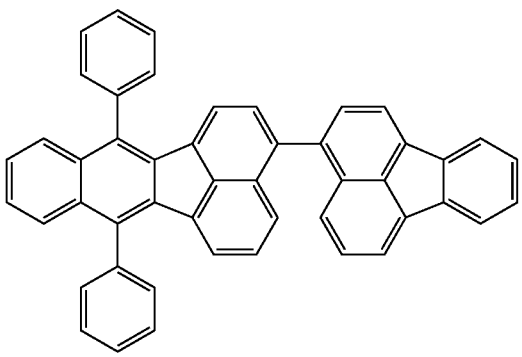

TABLE 1

| Compound No. | A | B |
|---|---|---|
| 101 | | |
| 102 | | |

TABLE 1-continued

| Compound No. | A | B |
|---|---|---|
| 103 | | |
| 104 | | |
| 105 | | |
| 106-1 | | |

TABLE 1-continued

| Compound No. | A | B |
| --- | --- | --- |
| 106-2 | | |

TABLE 2

| Compound No. | A | B |
| --- | --- | --- |
| 107 | | |
| 108 | | |

TABLE 2-continued
| Compound No. | A | B |
|---|---|---|
| 109 | 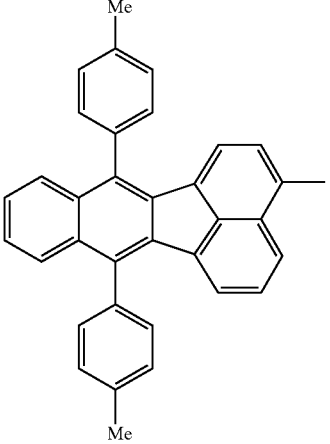 | 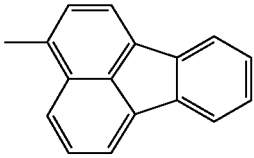 |
| 110 | 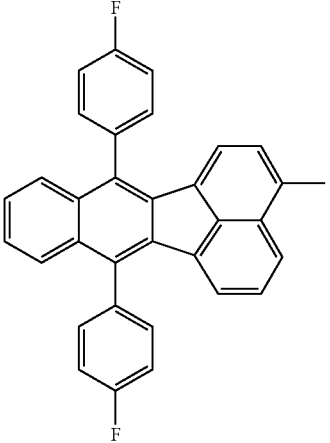 | 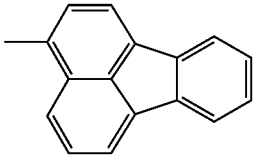 |
| 111 | 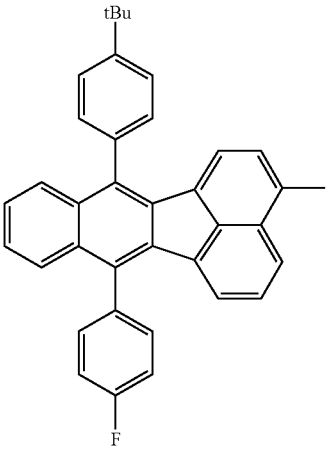 | 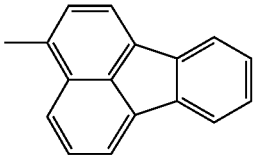 |

TABLE 3
| Compound No. | A | B |
|---|---|---|
| 112 | 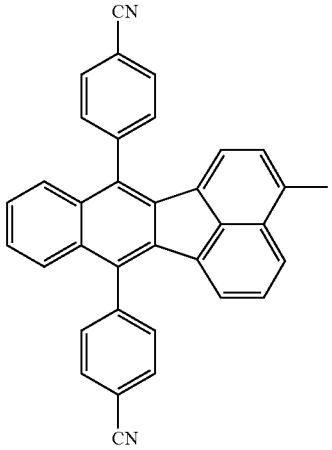 | 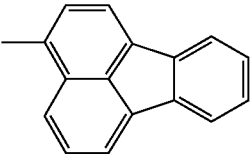 |
| 113 | 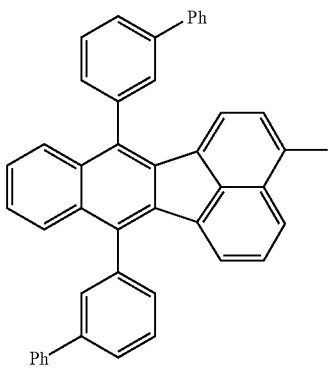 | 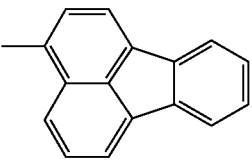 |
| 114 | 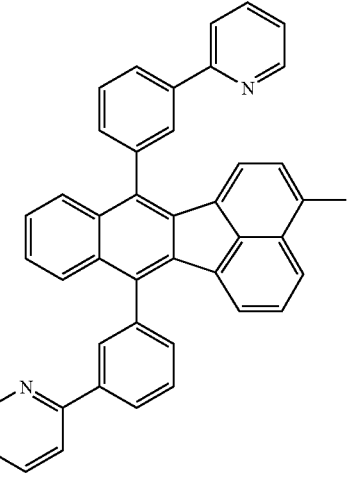 | 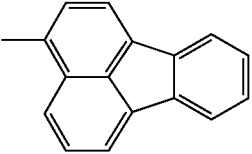 |

TABLE 3-continued

| Compound No. | A | B |
| --- | --- | --- |
| 115 | | |
| 116 | | |

TABLE 4

| Compound No. | A | B |
| --- | --- | --- |
| 117 | | |

TABLE 4-continued

| Compound No. | A | B |
| --- | --- | --- |
| 118 | | |
| 119 | | |
| 120 | | |
| 121-1 | | |

TABLE 4-continued

| Compound No. | A | B |
| --- | --- | --- |
| 121-2 | | |

TABLE 5

| Compound No. | A | B |
| --- | --- | --- |
| 122 | | |
| 123 | | |

TABLE 5-continued
| Compound No. | A | B |
|---|---|---|
| 124 | 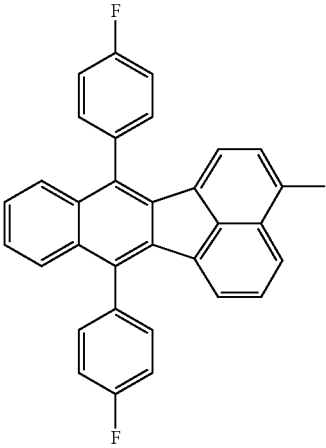 | 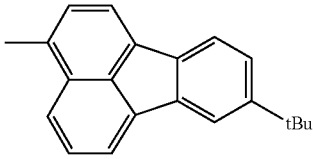 |
TABLE 6
| Compound No. | A | B |
|---|---|---|
| 125 | 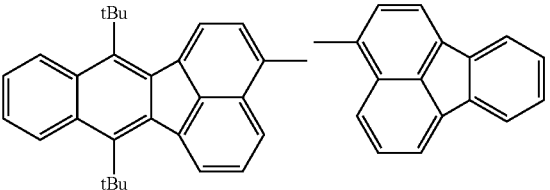 |  |
| 126 | 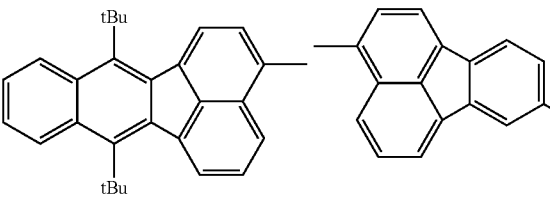 |  |
| 127 | 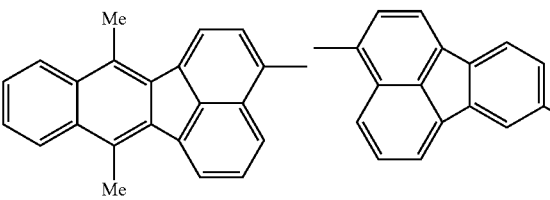 |  |
| 128 | 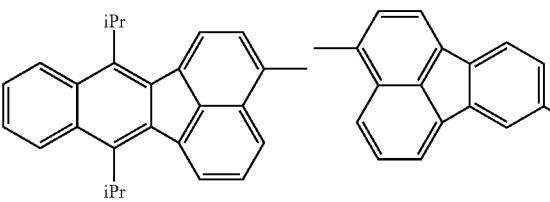 |  |
| 129 | 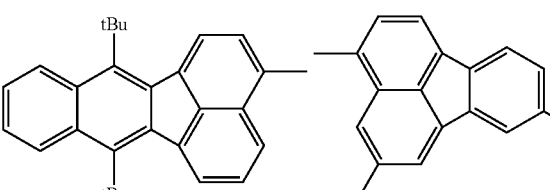 |  |

TABLE 7

| Compound No. | A | B |
|---|---|---|
| 130 | (structure with Me substituent) | (methylfluoranthene) |
| 131 | (structure with Ph substituent) | (methylfluoranthene) |
| 132 | (structure with F substituent) | (methylfluoranthene) |
| 133 | (structure with Ph substituent) | (methyl-tBu-fluoranthene) |

TABLE 7-continued

| Compound No. | A | B |
| --- | --- | --- |
| 134 | | |
| 135 | | |
| 136 | | |

TABLE 8
| Compound No. | A | B |
|---|---|---|
| 137 | 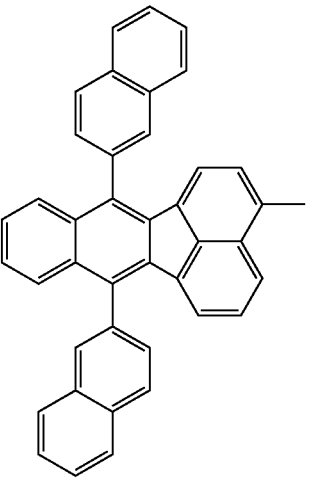 | 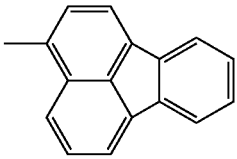 |
| 138 | 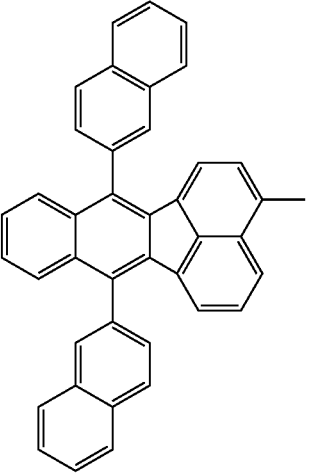 | 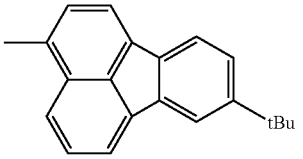 |
| 139 | 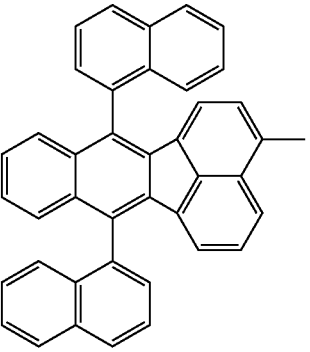 | 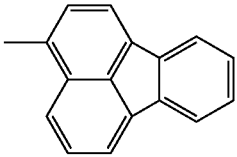 |

TABLE 8-continued

| Compound No. | A | B |
|---|---|---|
| 140 | (structure) | (structure) |
| 141 | (structure) | (structure) |

TABLE 9

| Compound No. | A | B |
|---|---|---|
| 201 | (structure) | (structure) |

TABLE 9-continued
| Compound No. | A | B |
|---|---|---|
| 202 | 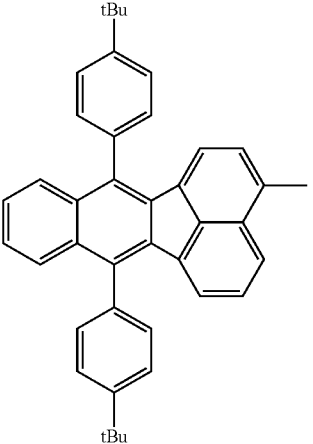 | 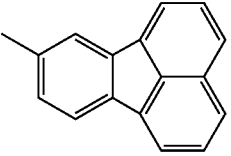 |
| 203 | 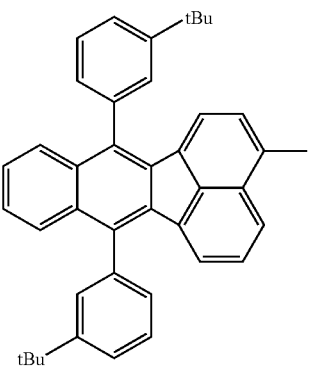 | 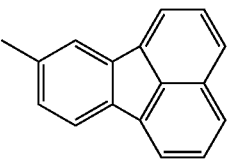 |
| 204 | 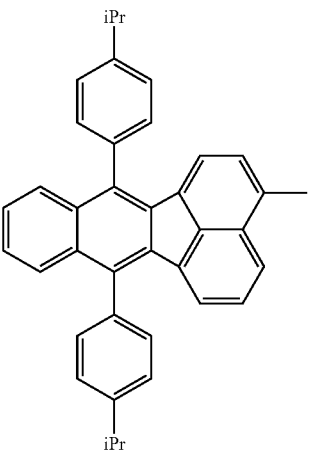 | 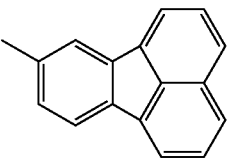 |

TABLE 9-continued
| Compound No. | A | B |
|---|---|---|
| 205 | 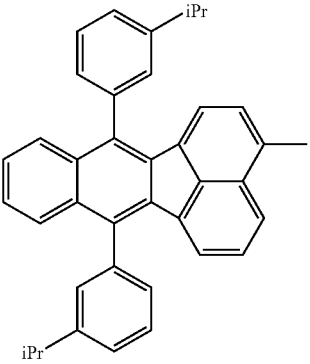 | 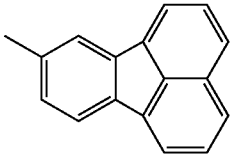 |
| 206-1 | 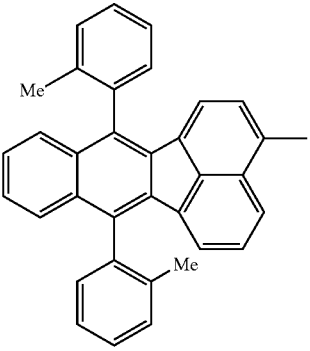 | 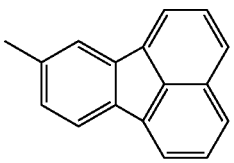 |
| 206-2 | 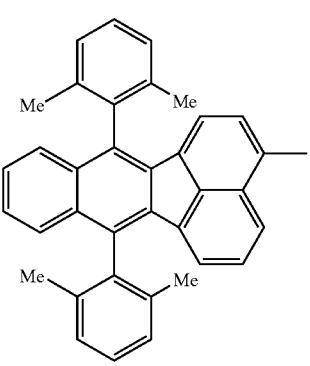 | 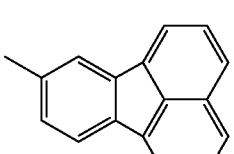 |

TABLE 10
| Compound No. | A | B |
|---|---|---|
| 207 | 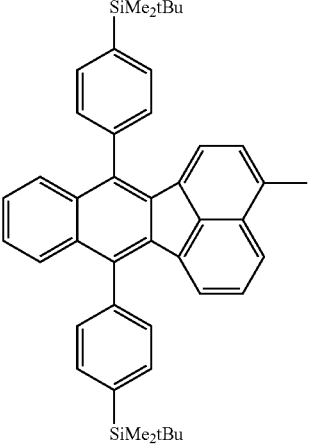 | 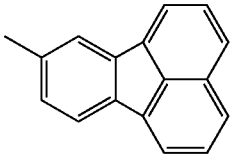 |
| 208 | 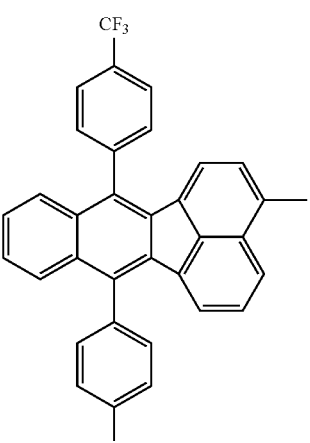 | 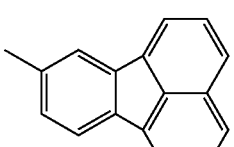 |
| 209 | 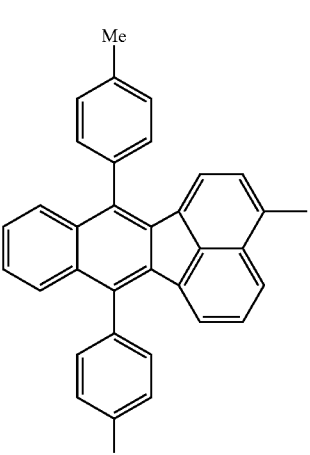 | 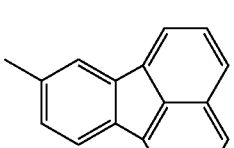 |

TABLE 10-continued

| Compound No. | A | B |
| --- | --- | --- |
| 210 | (structure with two 4-fluorophenyl groups on fluoranthene-type core with methyl) | (methyl-fluoranthene) |
| 211 | (structure with 4-tBu-phenyl and 4-fluorophenyl groups on fluoranthene-type core with methyl) | (methyl-fluoranthene) |
| 212 | (structure with two 4-cyanophenyl groups on fluoranthene-type core with methyl) | (methyl-fluoranthene) |

TABLE 11

| Compound No. | A | B |
|---|---|---|
| 213 | | |
| 214 | | |
| 215 | | |
| 216 | | |

TABLE 11-continued
| Compound No. | A | B |
|---|---|---|
| 217 | 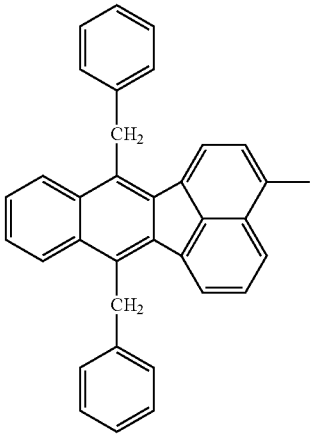 | 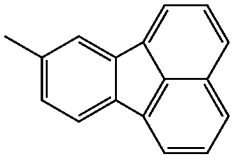 |
| 218 | 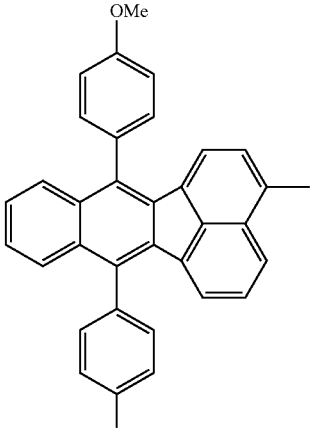 | 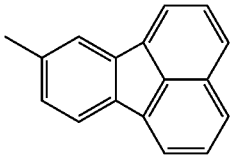 |
TABLE 12
| Compound No. | A | B |
|---|---|---|
| 219 | 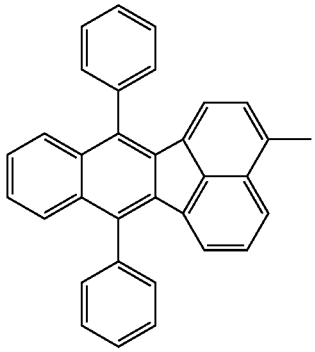 | 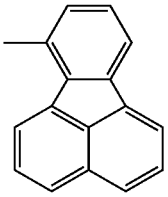 |

TABLE 12-continued
| Compound No. | A | B |
|---|---|---|
| 220 | 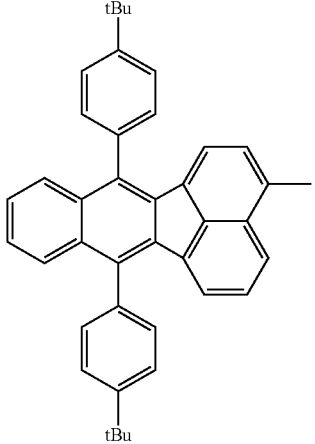 | 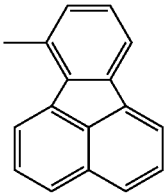 |
| 221-1 | 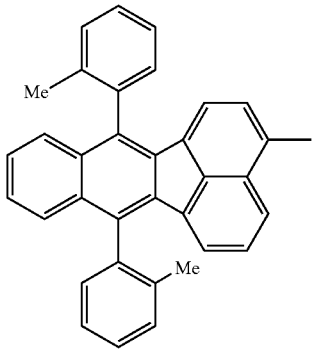 | 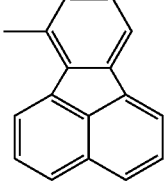 |
| 221-2 | 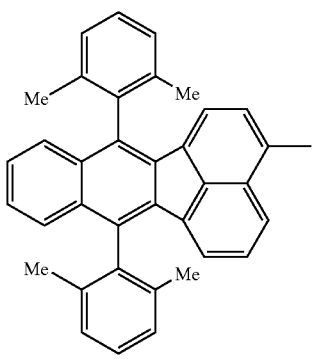 | 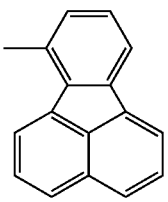 |

TABLE 12-continued
| Compound No. | A | B |
|---|---|---|
| 222 | 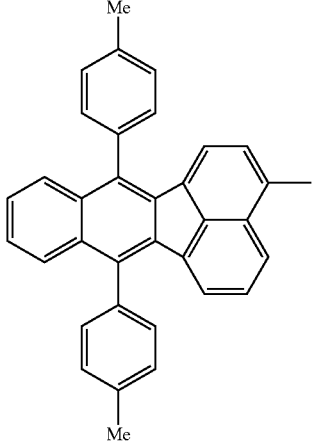 | 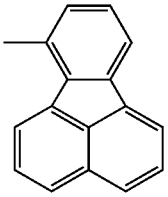 |
| 223 | 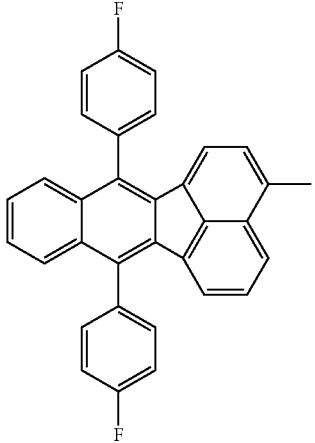 | 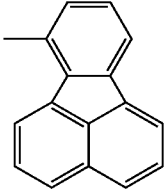 |
TABLE 13
| Compound No. | A | B |
|---|---|---|
| 223-2 | 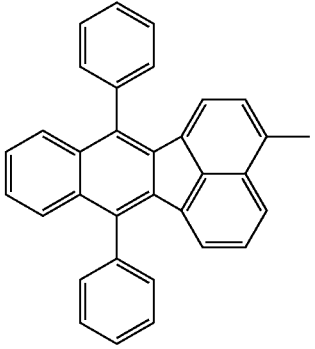 | 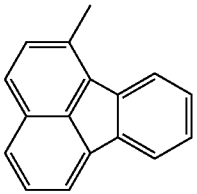 |

TABLE 13-continued
| Compound No. | A | B |
| --- | --- | --- |
| 224 | 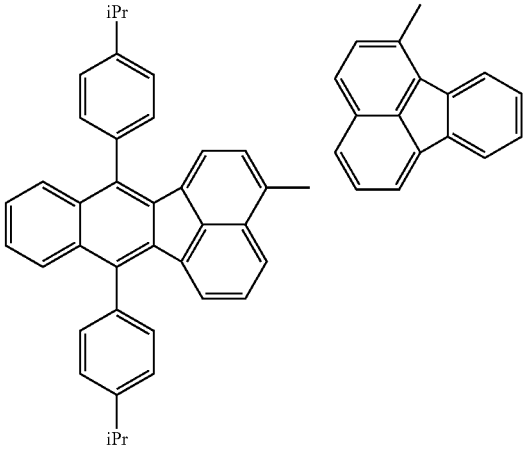 | 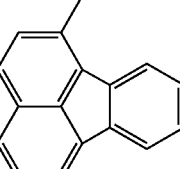 |
| 225 | 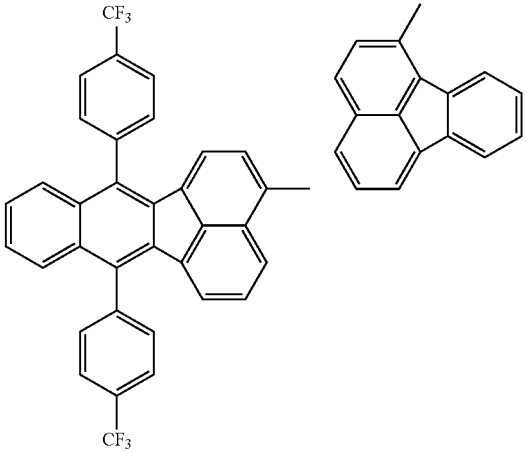 | 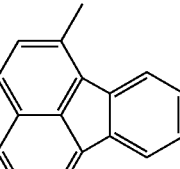 |
| 226 | 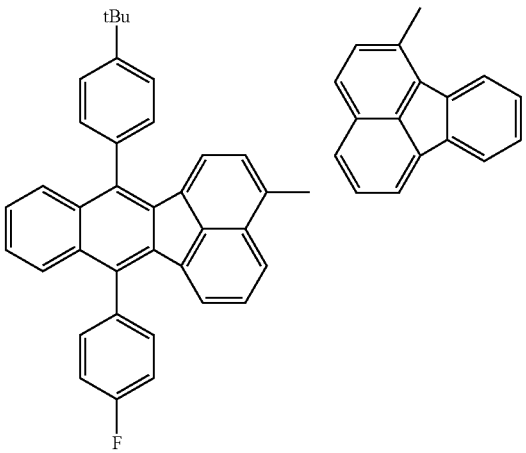 | 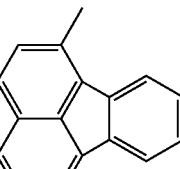 |

TABLE 13-continued

| Compound No. | A | B |
|---|---|---|
| 227 | (structure with Ph substituents) | (fluoranthene structure) |
| 228 | (structure with F substituents) | (fluoranthene structure) |

TABLE 14

| Compound No. | A | B |
|---|---|---|
| 229 | (structure with phenyl substituents) | (fluoranthene structure) |
| 230 | (structure with iPr substituents) | (fluoranthene structure) |

TABLE 14-continued
| Compound No. | A | B |
|---|---|---|
| 231 | 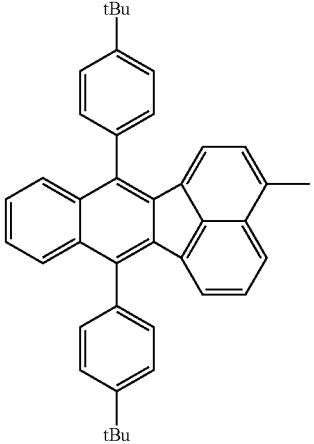 | 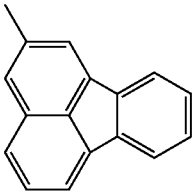 |
| 232 | 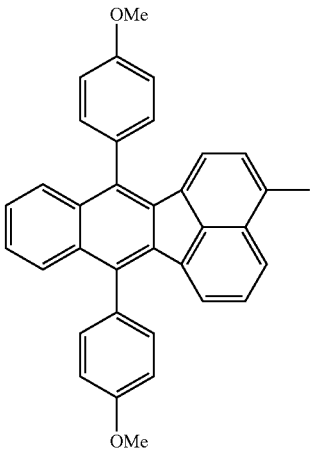 | 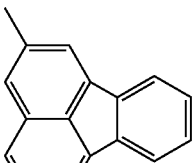 |
TABLE 15
| Compound No. | A | B |
|---|---|---|
| 233 | 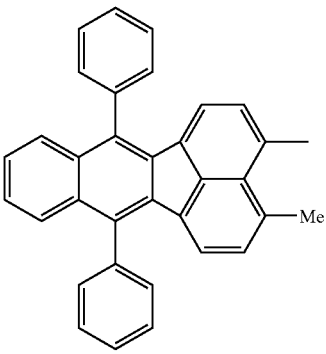 | 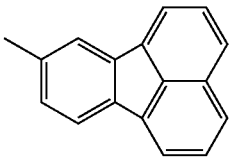 |

TABLE 15-continued

| Compound No. | A | B |
| --- | --- | --- |
| 234 | | |
| 235 | | |
| 236 | | |
| 237 | | |

TABLE 15-continued

| Compound No. | A | B |
| --- | --- | --- |
| 238 | | |

TABLE 16

| Compound No. | A | B |
| --- | --- | --- |
| 239 | | |
| 240 | | |
| 241 | | |

TABLE 16-continued
| Compound No. | A | B |
|---|---|---|
| 242 | 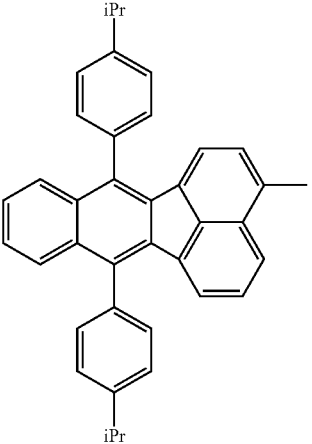 | 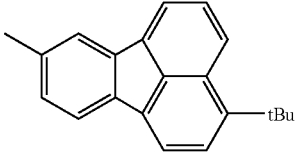 |
| 243 | 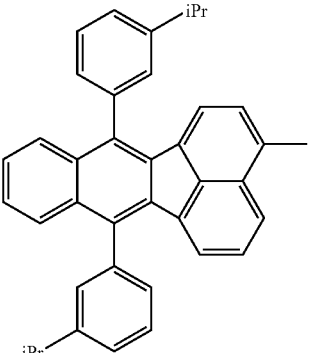 | 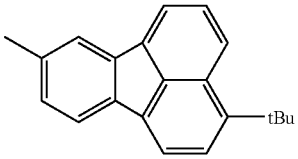 |
| 244-1 | 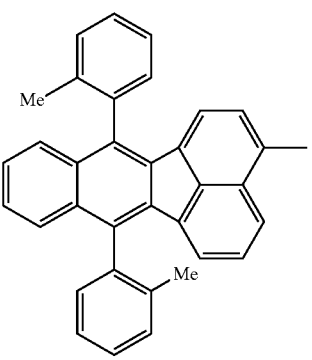 | 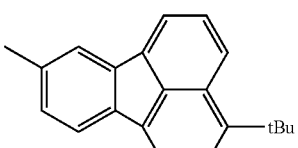 |
| 244-2 | 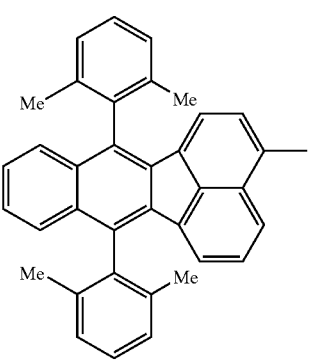 | 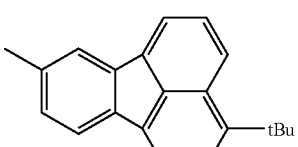 |

TABLE 17
| Compound No. | A | B |
|---|---|---|
| 245 | 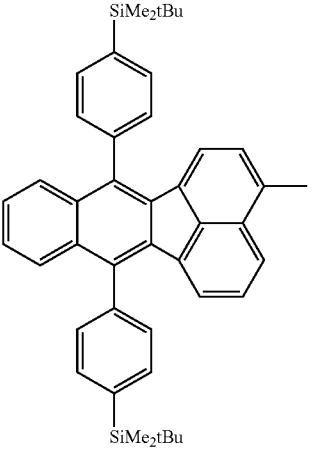 | 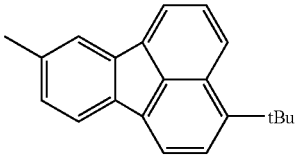 |
| 246 | 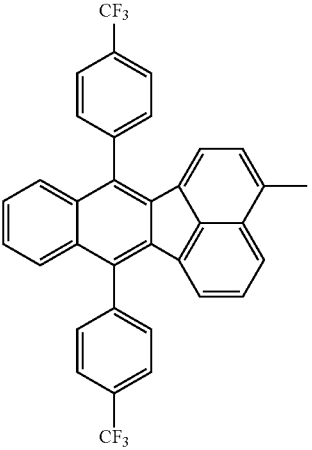 | 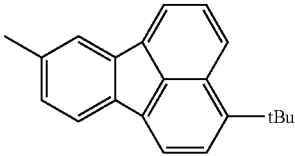 |
| 247 | 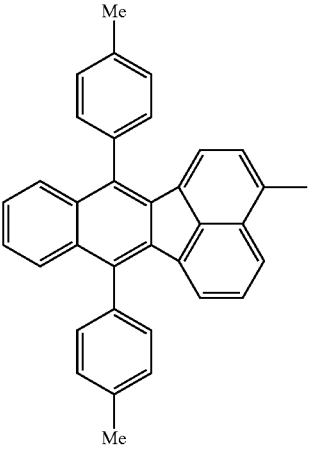 | 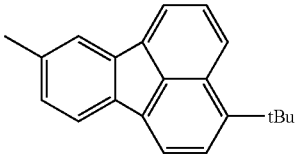 |

TABLE 17-continued
| Compound No. | A | B |
| --- | --- | --- |
| 248 | 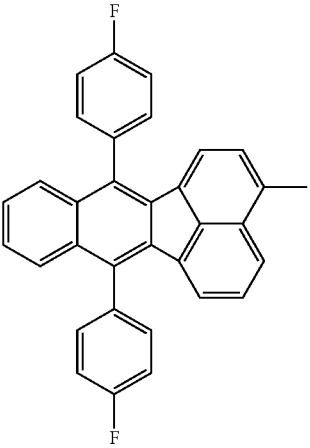 | 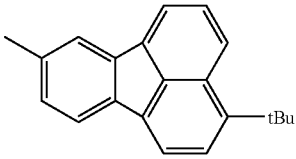 |
| 249 | 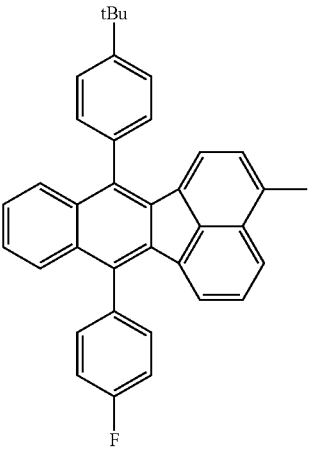 | 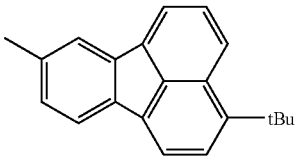 |
TABLE 18
| Compound No. | A | B |
| --- | --- | --- |
| 250 | 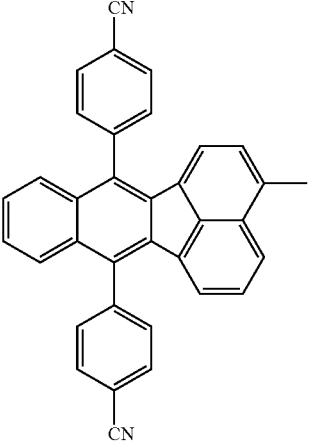 | 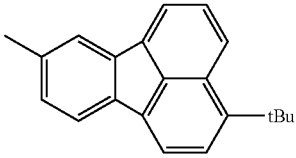 |

TABLE 18-continued

| Compound No. | A | B |
| --- | --- | --- |
| 251 | | |
| 252 | | |
| 253 | | |
| 254 | | |

TABLE 18-continued

| Compound No. | A | B |
|---|---|---|
| 255 | (structure) | (structure) |

TABLE 19

| Compound No. | A | B |
|---|---|---|
| 256 | (structure) | (structure) |
| 257 | (structure) | (structure) |
| 258 | (structure) | (structure) |
| 259 | (structure) | (structure) |
| 260 | (structure) | (structure) |

TABLE 20

| Compound No. | A | B |
|---|---|---|
| 261 | [2-naphthyl, 2-naphthyl-substituted benzo[k]fluoranthene core structure] | [methyl-substituted fluoranthene] |
| 262 | [2-pyridyl, 2-pyridyl-substituted benzo[k]fluoranthene core structure] | [methyl-substituted fluoranthene] |
| 263 | [3-quinolinyl, 3-quinolinyl-substituted benzo[k]fluoranthene core structure] | [methyl-substituted fluoranthene] |

As to the benzo[k]fluoranthene compound, synthesis methods therefor are disclosed from old times. For example, a document "J. Am. Chem. Soc., 74, 1075 (1952)" may be cited. This document discloses synthesis of 7,12-diphenyl-benzo[k]fluoranthene by the Diels-Alder reaction of diphenylisobenzofuran with acenaphthylene.

3-Bromobenzo[k]fluoranthene, which is a precursor material of the benzo[k]fluoranthene compound used in the present invention, can be synthesized by using a bromine compound of acenaphthylene. The bromine compound of acenaphthylene can be synthesized by oxidation reaction of 5-bromoacenaphthene as disclosed in, e.g., a document "Can. J. Chem., 70, 1015 (1992)". Similarly, 5,6-dibromoacenaphthene may be synthesized from 5,6-dibromoacenaphthylene.

The benzo[k]fluoranthene compound used in the present invention may be synthesized by, e.g., Suzuki-Miyaura coupling reaction of a bromine compound of corresponding benzo[k]fluoranthene with a pinacol borane compound derived from bromofluoranthene. It may similarly be synthesized by reacting a pinacol borane compound of benzofluoranthene with a bromine compound of fluoranthene. In place of the pinacol borane compound, boric acid may be used.

Pinacol borane may be formed by reacting a halogen compound with 4,4,5,5-tetramethyl-[1,3,2]dioxabororane in, e.g., a toluene solvent and in the presence of triethylamine and a catalyst Ni(dppp)Cl.

A tert-butyl group-substituted fluoranthene unit can be synthesized by Friedel-Crafts alkylation of bromofluoranthene.

All the above methods are similarly applicable to synthesis of a second compound described later.

The organic luminescent device of the present invention is described below in detail.

The organic luminescent device of the present invention has at least a pair of electrodes consisting of an anode and a cathode at least one of which is transparent or semitransparent, and one or two or more layers containing an organic compound, held between the pair of electrodes. In this case, at least one of the layer(s) containing an organic compound, preferably at least one layer having a luminescent region, and more preferably a luminescent layer, contains at least one benzo[k]fluoranthene compound of the present invention, described above.

The layer containing the benzo[k]fluoranthene compound may contain a second compound (a host material). The host material is preferably a compound having a larger energy gap than the benzo[k]fluoranthene compound.

The second compound includes, but is not limited to, e.g., such materials having a pyrene skeleton as shown below.

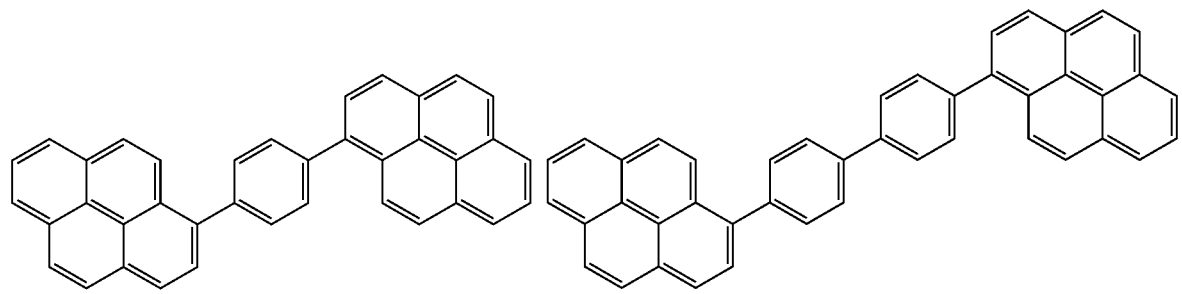

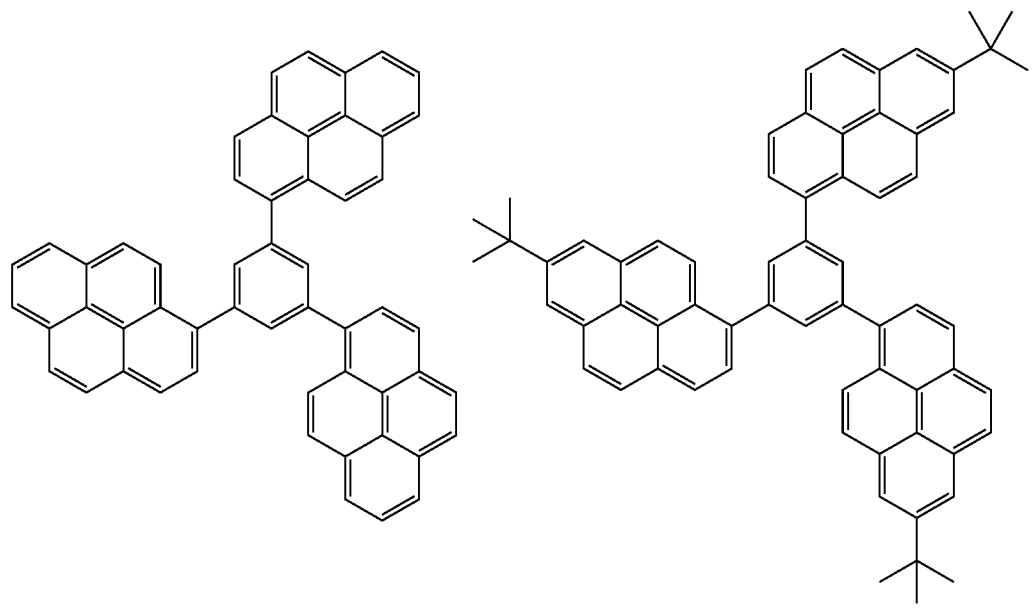

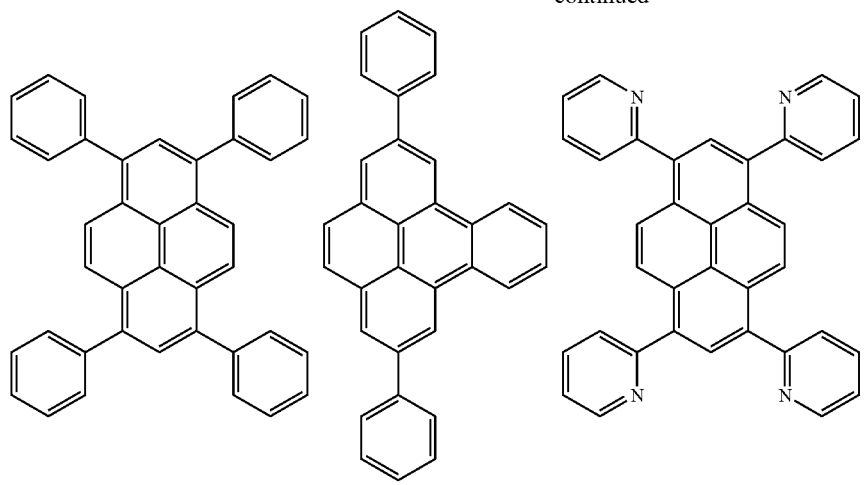

-continued
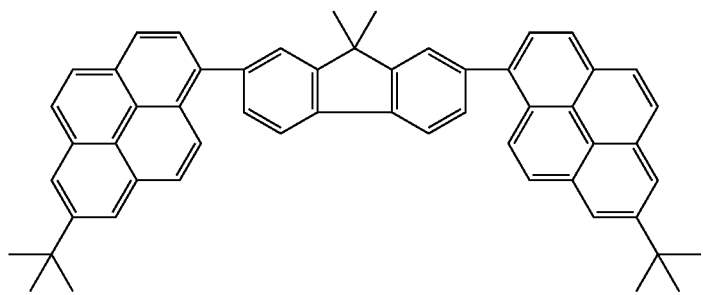
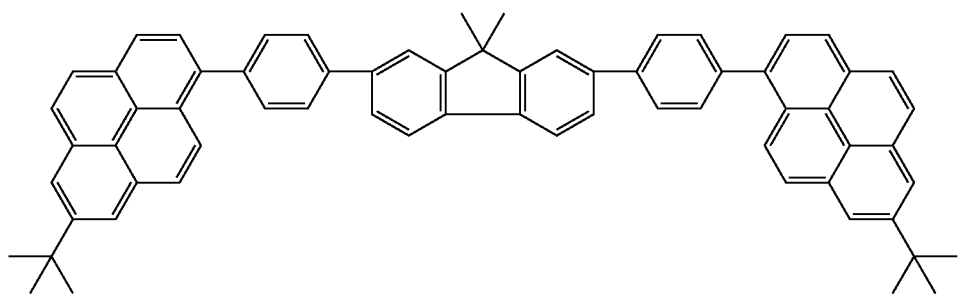
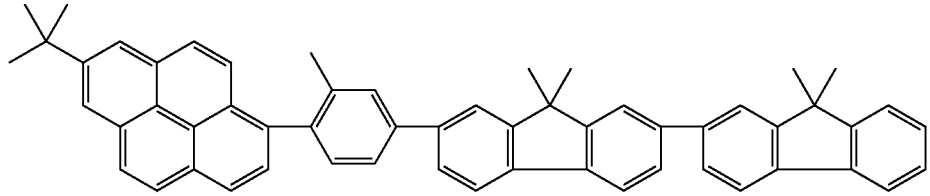
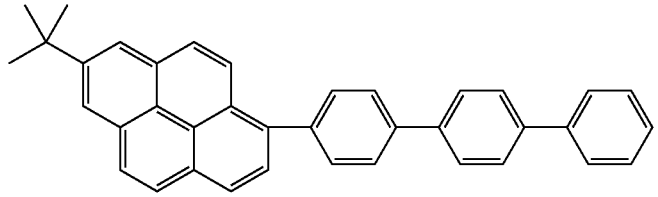
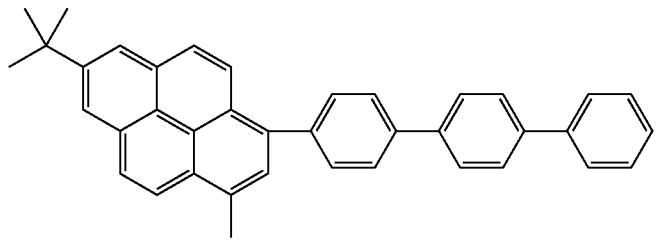
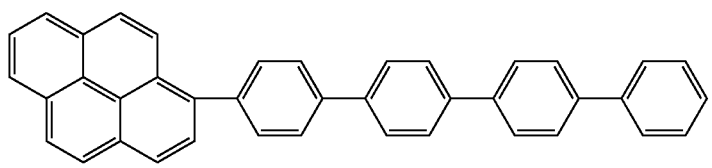
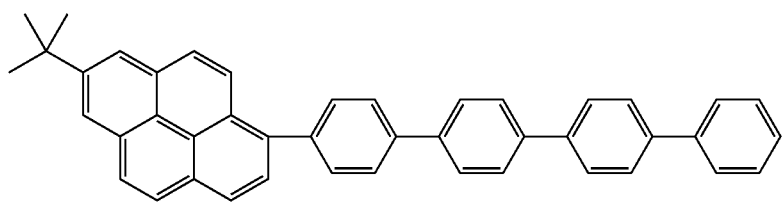

-continued
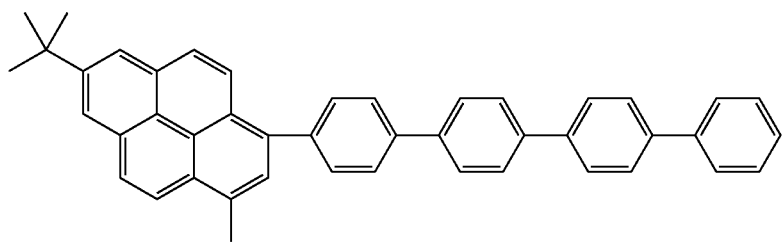
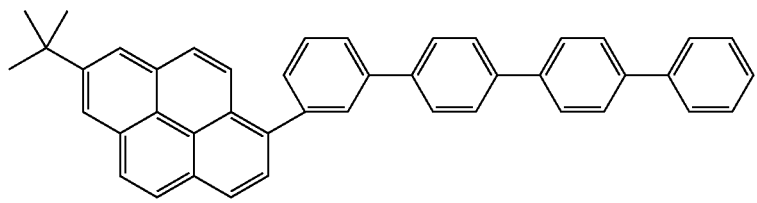
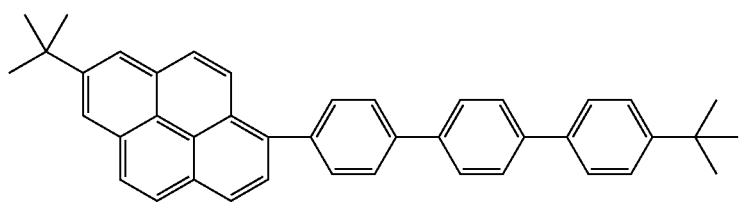
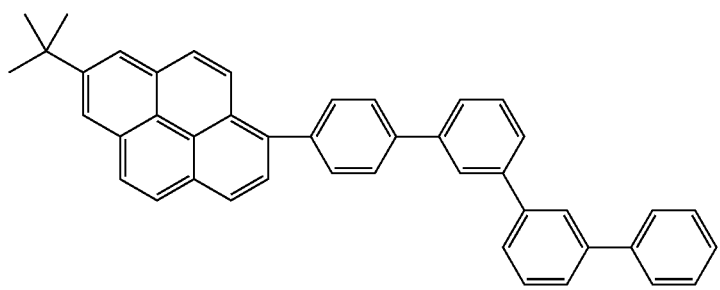
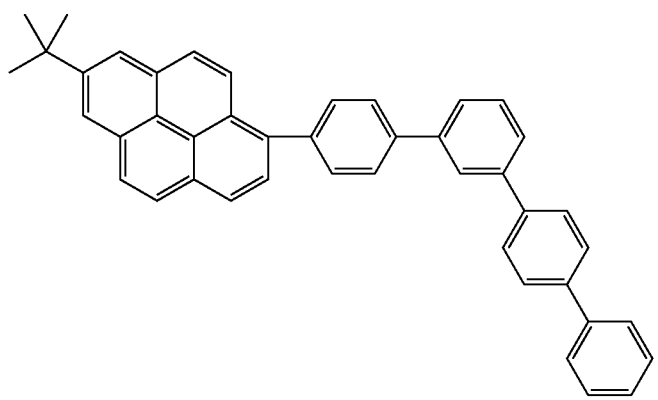
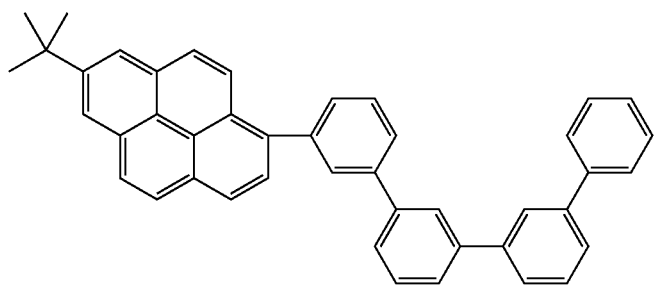

-continued
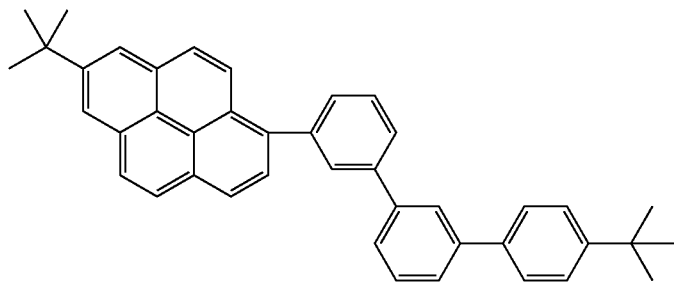
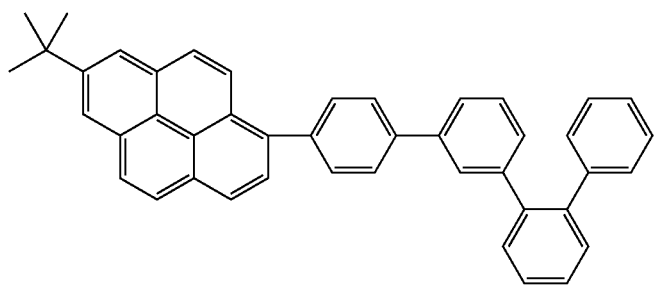
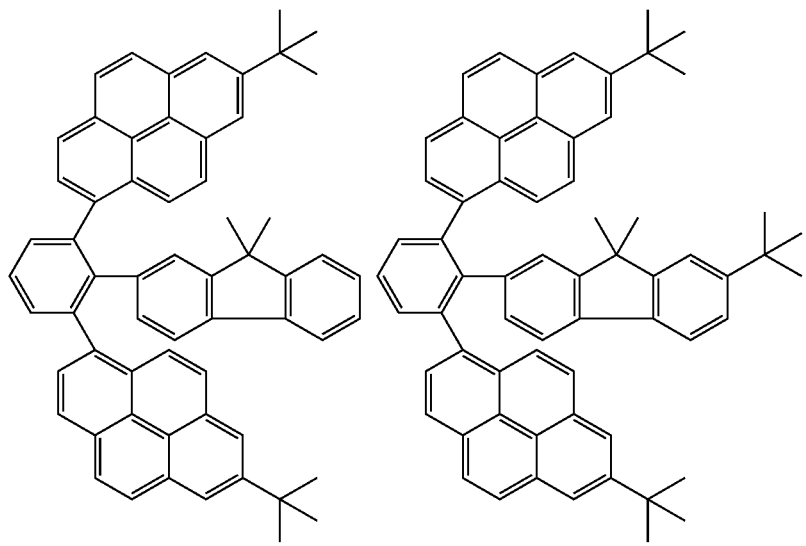
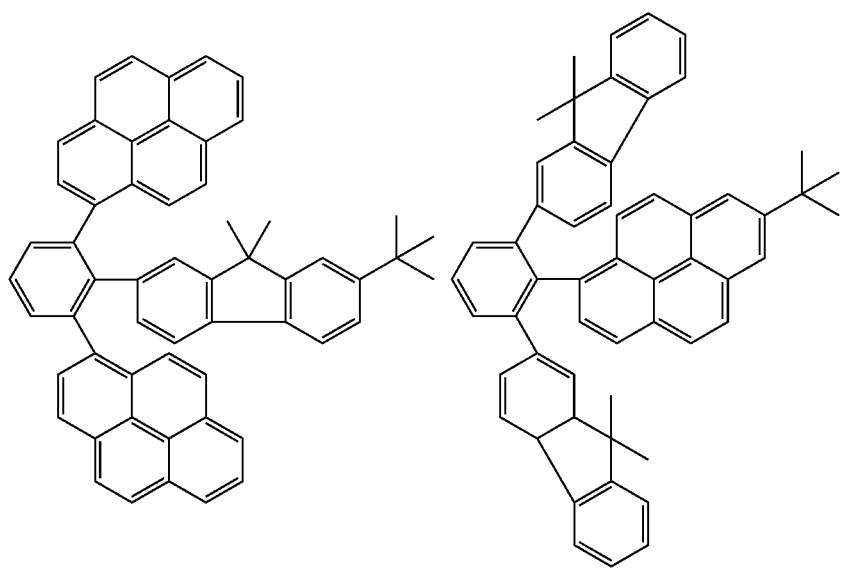

The second compound further includes, but is not limited to, e.g., such materials having a condensed-ring aromatic group as shown below.

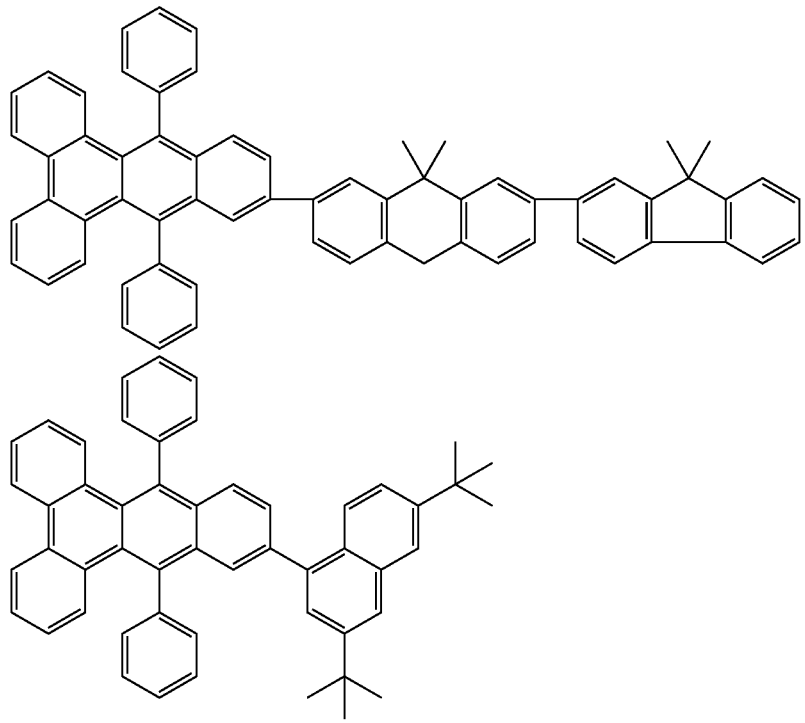

In particular, a compound represented by the following general formula (4), preferably a compound wherein $Y_1$ and $Y_2$ of the general formula (4) are each independently represented by the following general formula (5), (6) or (7), and more preferably a compound represented by the following general formula (8) or further by the following general formula (9) or (10), may be used as the second compound, whereby the continuation of good light emission can be achieved with high luminous efficiency and reduced deterioration in luminance.

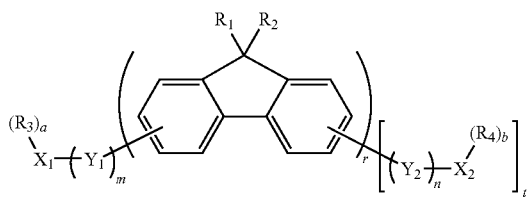

[4]

In the general formula (4), $R_1$ and $R_2$ are each independently a group selected from the group consisting of a hydrogen atom, a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic group, $R_1$'s may be the same or different, and $R_2$'s may be the same or different;

$R_3$ and $R_4$ are each independently a group selected from the group consisting of a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic group, $R_3$'s may be the same or different, and $R_4$'s may be the same or different;

$X_1$ and $X_2$ are each independently a substituted or unsubstituted aryl group or a substituted or unsubstituted heterocyclic ring group;

a and b are each independently an integer of 0 to 3;

$Y_1$ and $Y_2$ are each independently a substituted or unsubstituted phenylene group, $Y_1$'s may be the same or different, and $Y_2$'s may be the same or different;

m and n are each independently an integer of 1 to 3;

t is 0 or 1, and, when t is 0, the terminal fluorenyl group may be substituted, at its position where it is substituted with $Y_2$, with a group selected from the group consisting of a halogen atom, a substituted or unsubstituted alkyl group, a substituted or unsubstituted aralkyl group, a substituted or unsubstituted alkoxyl group and a substituted or unsubstituted phenyl group; and r is an integer of 1 to 5.

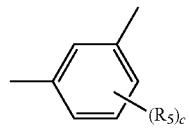

[5]

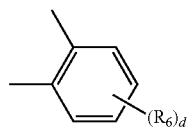

[6]

In the general formulas (5) and (6), $R_5$ and $R_6$ are each independently a group selected from the group consisting of a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic group, $R_5$'s may be the same or different, and $R_6$'s may be the same or different; and c and d are each independently an integer of 0 to 4.

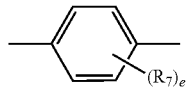

[7]

In the general formula (7), $R_7$ is a group selected from the group consisting of a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic ring group, $R_7$'s may be the same or different; and e is an integer of 0 to 4.

In the general formula (8), $R_1$ to $R_4$, $Y_1$, $Y_2$, a, b, m, n, r and t, and, in the general formulas (9) and (10), $R_1$ to $R_5$, a, b, c and t are as defined in the general formulas (4) and (5).

In the above general formulas (4) to (10), the hydrogen substituents may be heavy hydrogen. Specific examples of the substituted or unsubstituted alkyl group, aralkyl group and heterocyclic group and the halogen atom may include those listed in regard to the above general formulas (1) to (3) and (11) to (13).

Besides, the substituted or unsubstituted alkoxyl group may include alkyloxyl groups having an alkyl group or an aralkyl group, aralkyloxyl groups, the substituted or unsubstituted aryl group described in regard to the above general formulas (1) to (3) and (11) to (13), and alkoxyl groups having a heterocyclic group. The substituted or unsubstituted alkoxyl group more specifically includes, but is not limited to, a methoxyl group, an ethoxyl group, a propoxyl group, a 2-ethyl-octyloxyl group, a phenoxyl group, a 4-tert-butylphenoxyl group, a benzyloxyl group and a thienyloxyl group.

The substituted or unsubstituted aryl group includes the phenyl group and condensed bicyclic aromatic group described previously, and besides a substituted or unsubstituted tricyclic or higher condensed-ring aromatic group. The substituted or unsubstituted, condensed tri or more cyclic

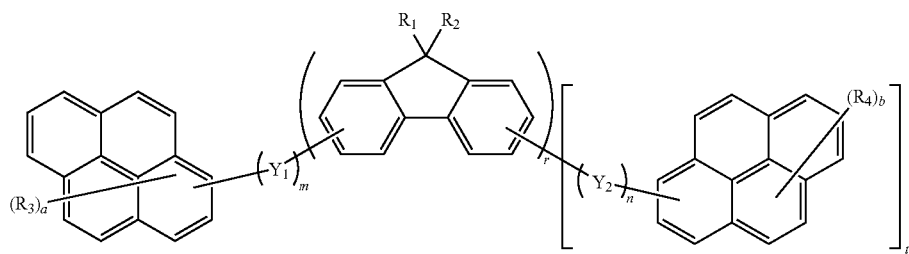

[8]

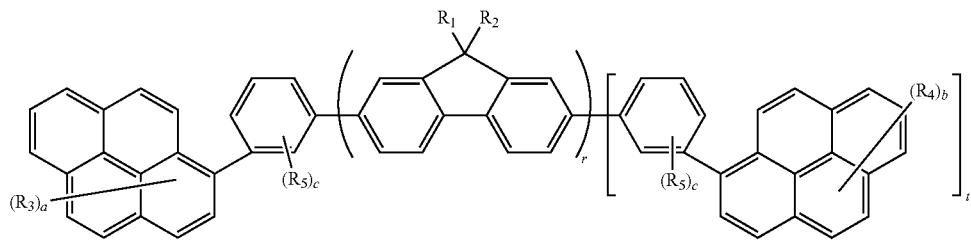

[9]

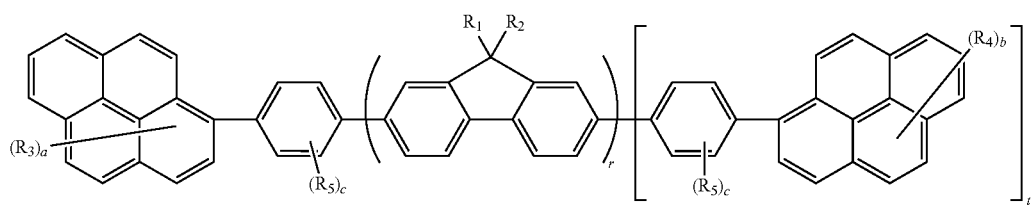

[10]

aromatic group includes, but is not limited to, an acenaphthylenyl group, an anthryl group, a phenanthryl group, a pyrenyl group, a fluoranthenyl group, a benzofluoranthenyl group, an acephenanthrylenyl group, an aceanthrylenyl group, a chrysenyl group, a dibenzochrysenyl group, a benzoanthryl group, a naphthacenyl group, a picenyl group, a fluorenyl group and a triphenylenyl group.

Of the compound represented by the general formula (4), the compound wherein $Y_1$ and $Y_2$ are each independently a group selected from the groups represented by the general formulas (5) and (6) and at least one of $X_1$ and $X_2$ is a substituted or unsubstituted pyrene ring includes, but is not limited to, e.g., the following materials.

H1

H1-1
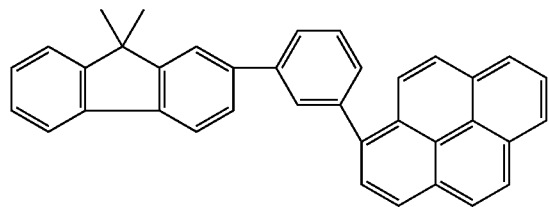

H1-2
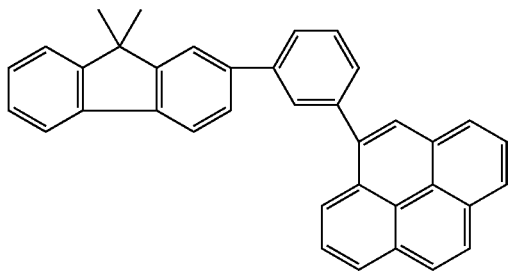

H1-3
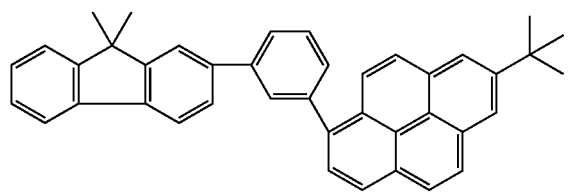

H1-4
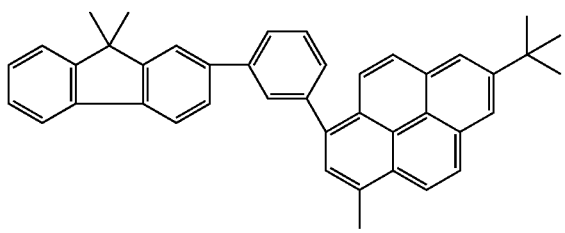

H1-5
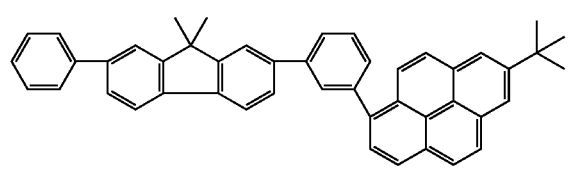

H1-6
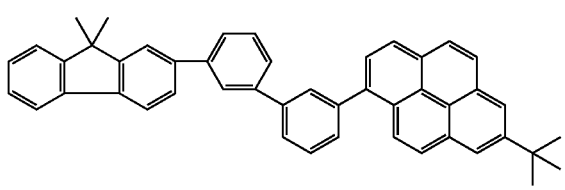

H1-7
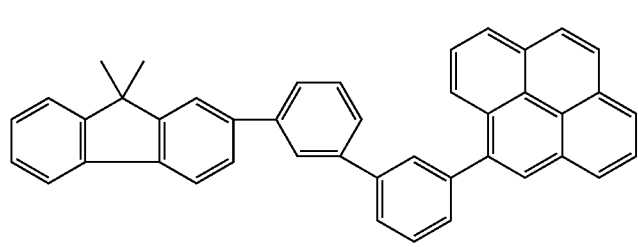

H1-8
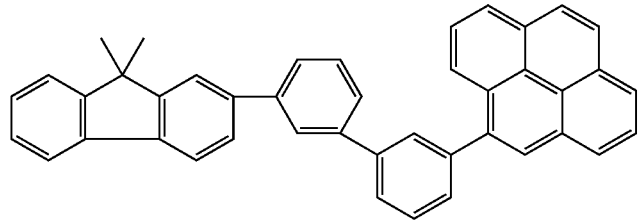

H1-9
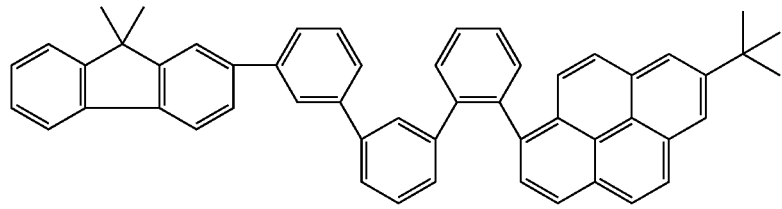

H1-10
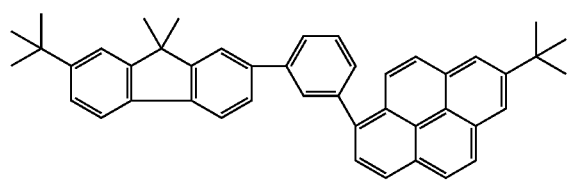
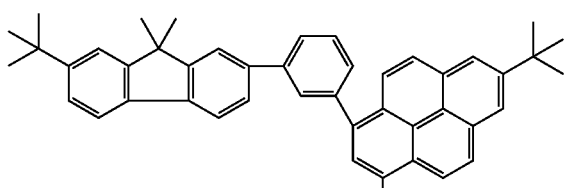

-continued
H2
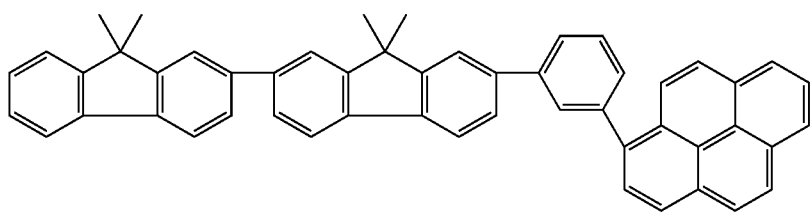
H2-1
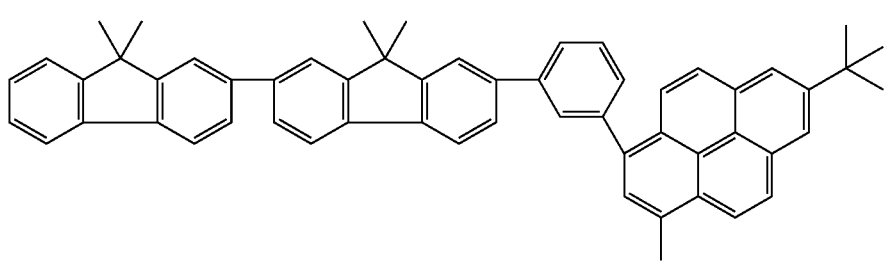
H2-2
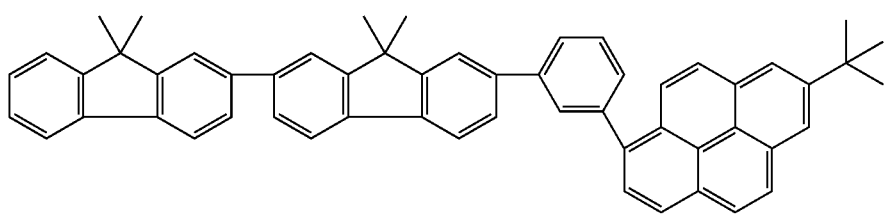
H2-3
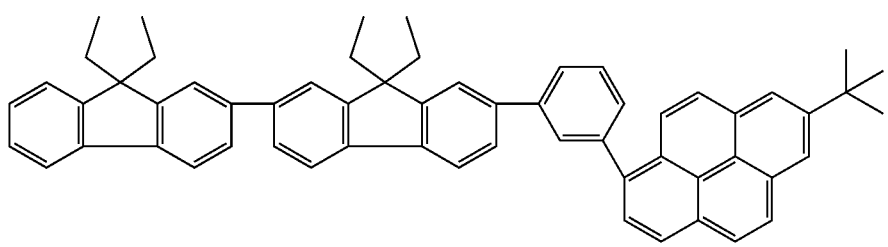
H2-4
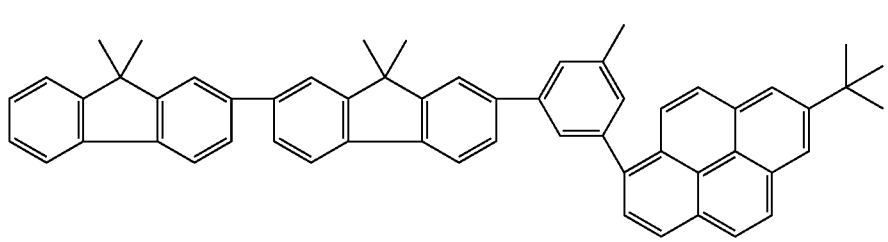
H2-5
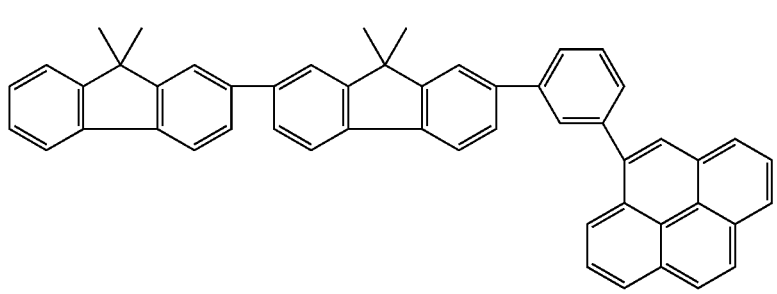
H2-6

-continued
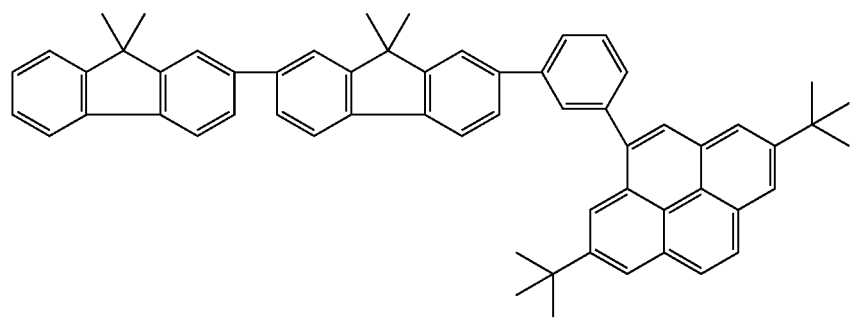
H2-7
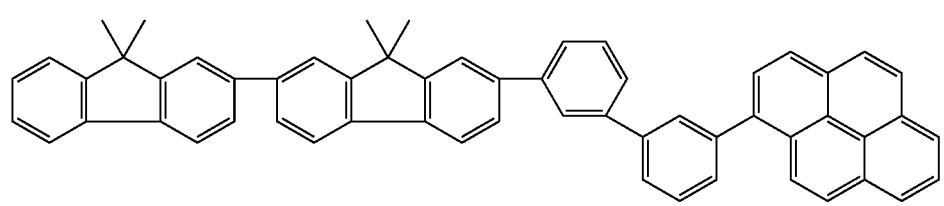
H2-8
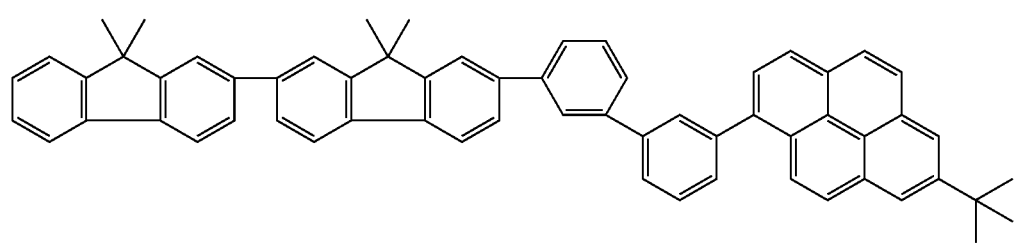
H2-9
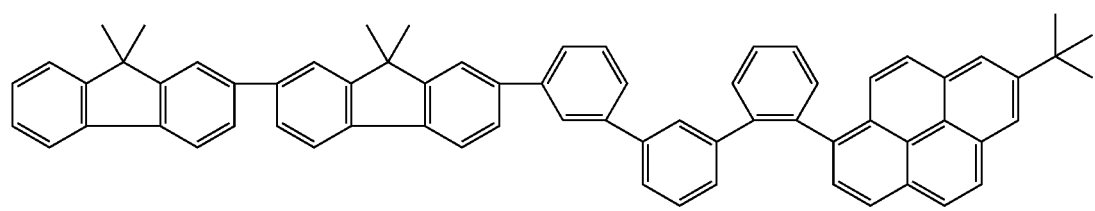
H2-10
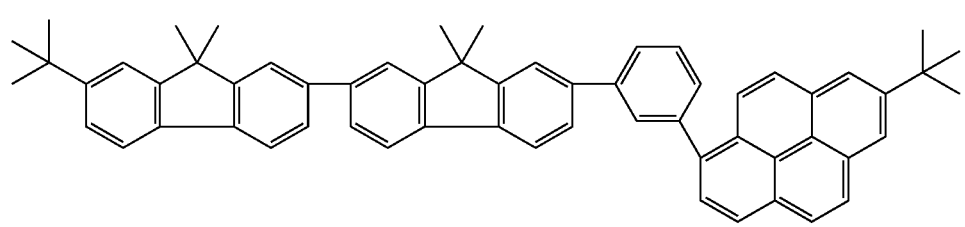
H2-11
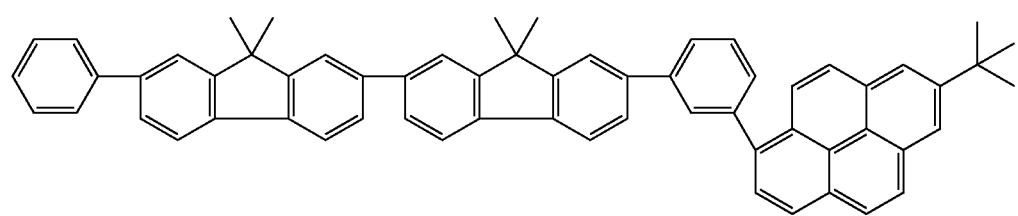
H2-12
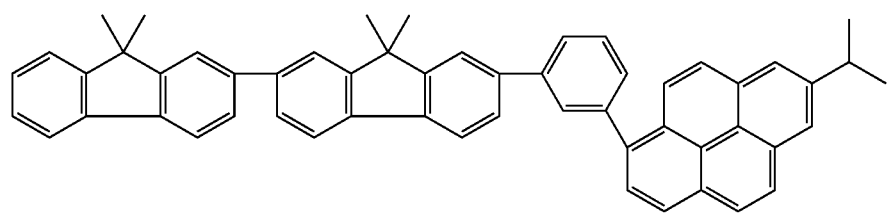
H2-13

H2-14
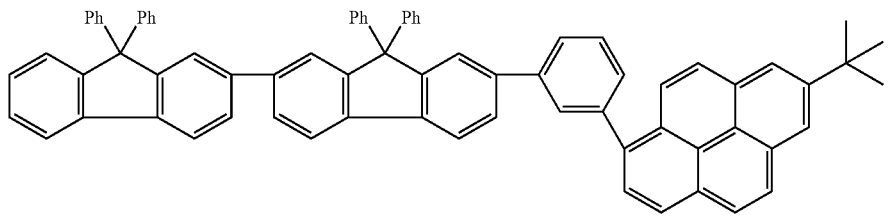
H3
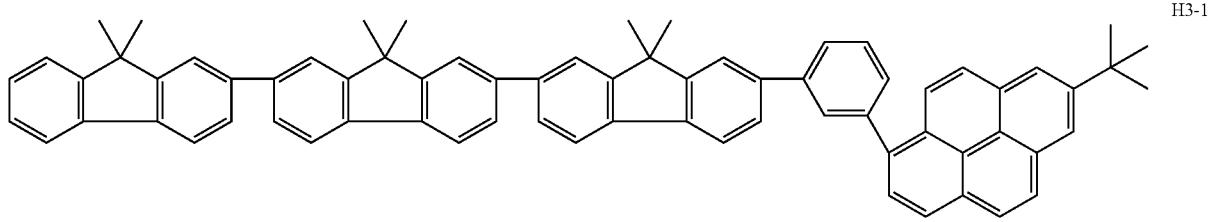
H3-1
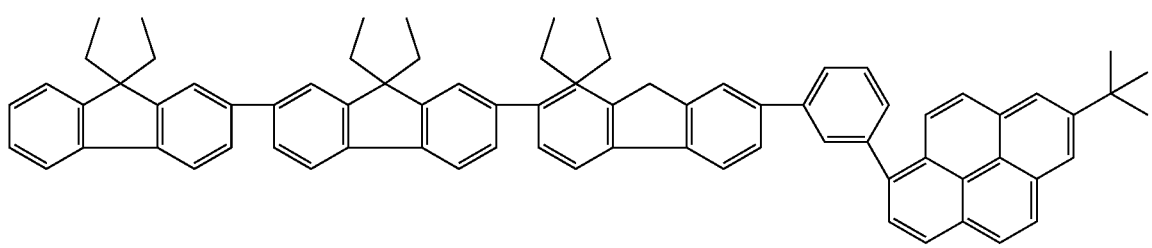
H3-2
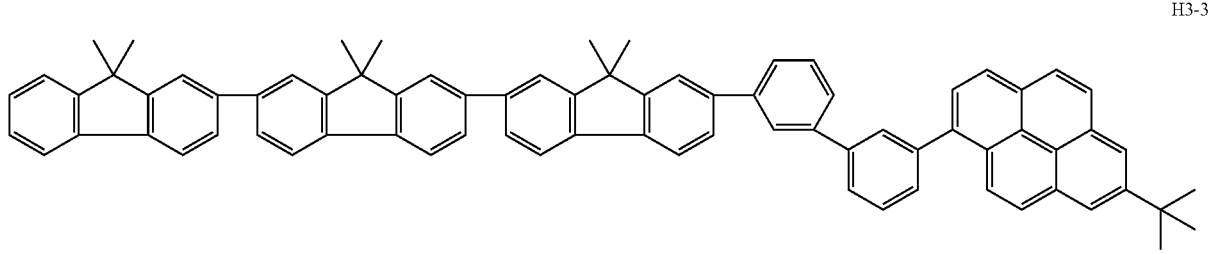
H3-3
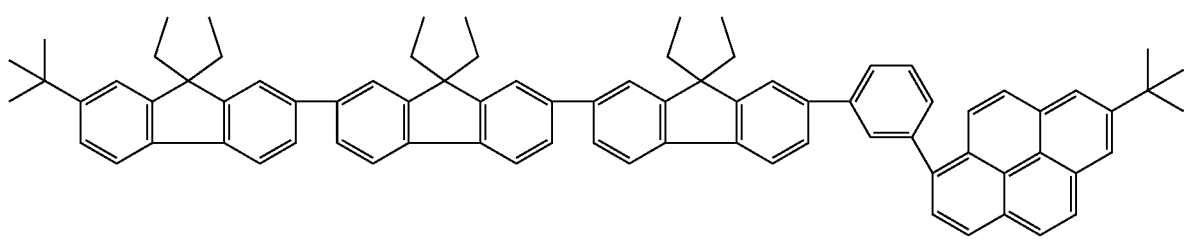
H3-4
H4
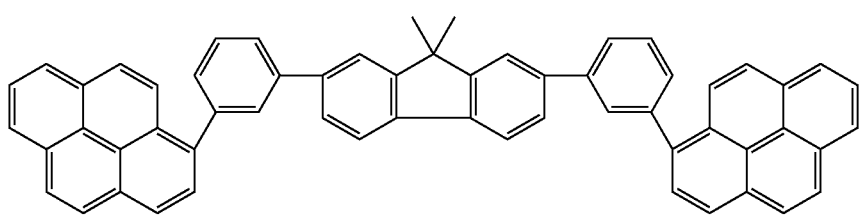
H4-1

-continued
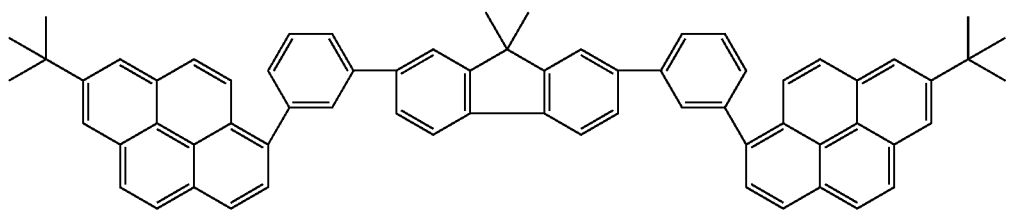
H4-2
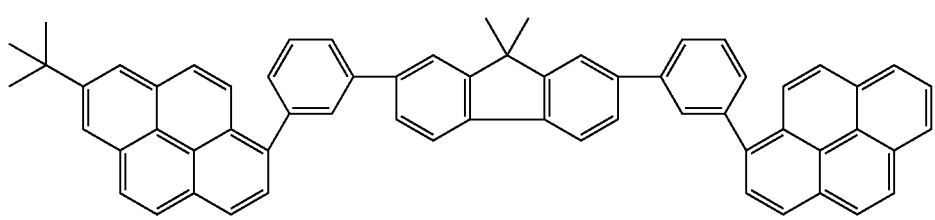
H4-3
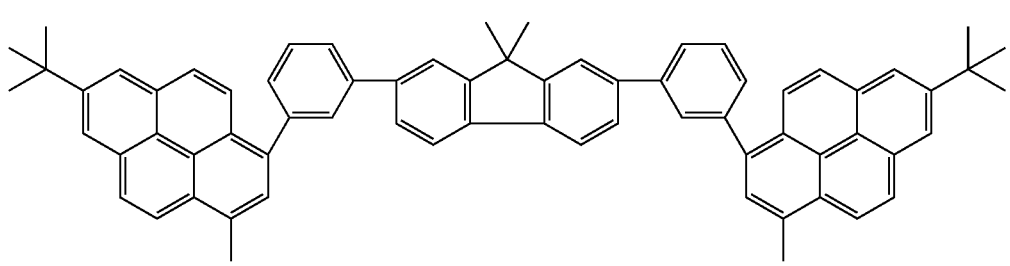
H4-4
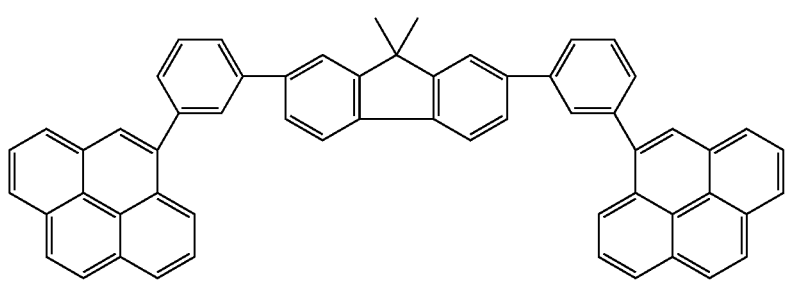
H4-5
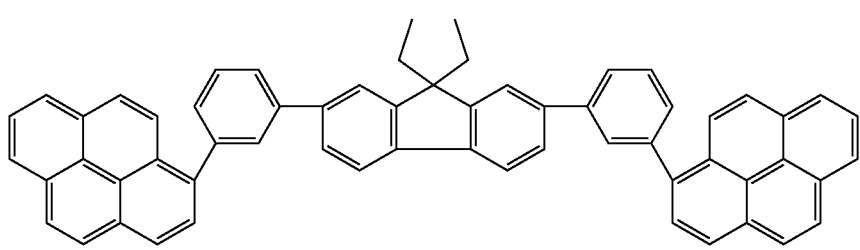
H4-6
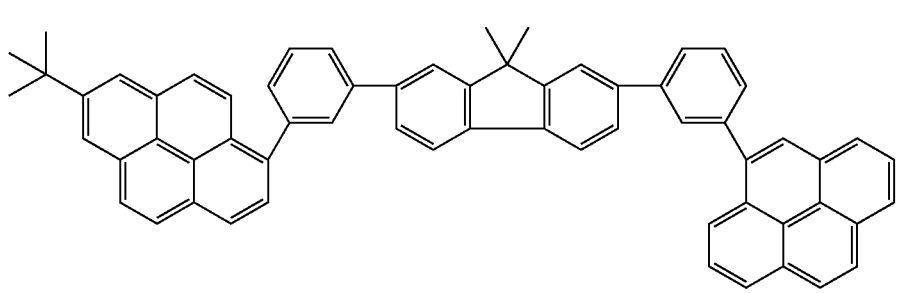
H4-7

-continued
H4-8
H4-9
H5
H5-1
H5-2
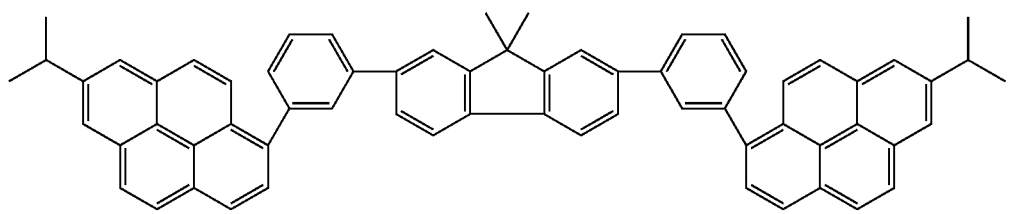

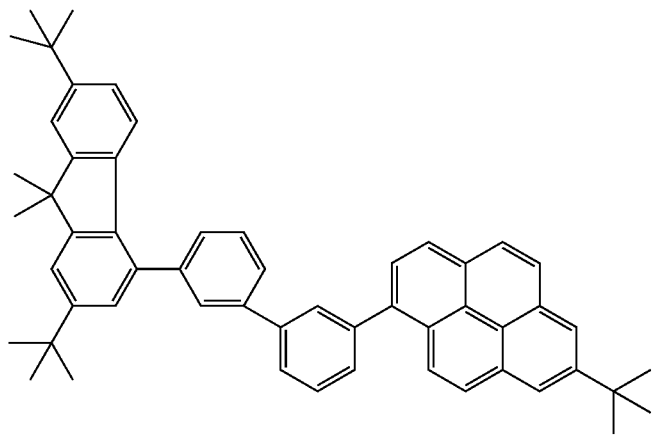
H5-3
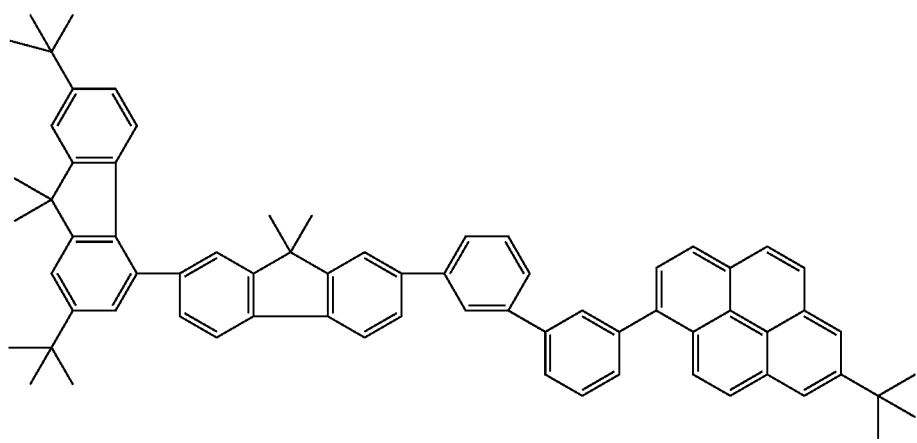
H5-4
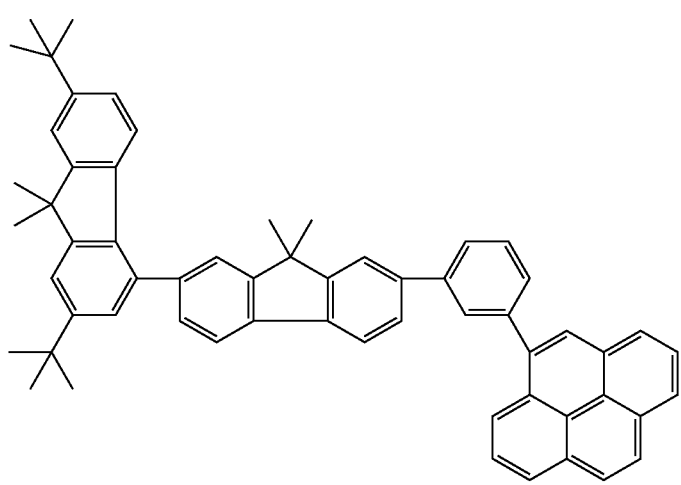
H5-5

H6
H6-1
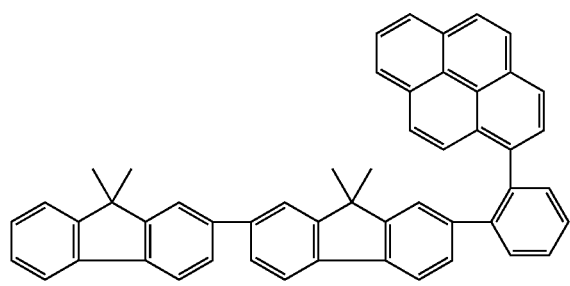
H6-2
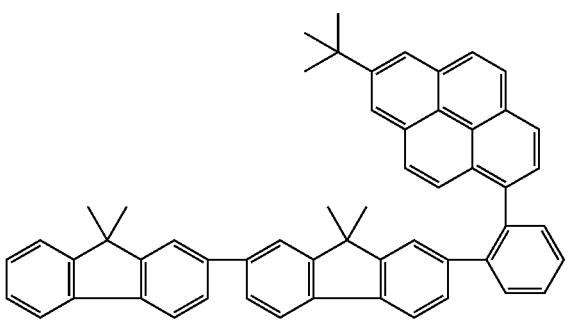
H6-3
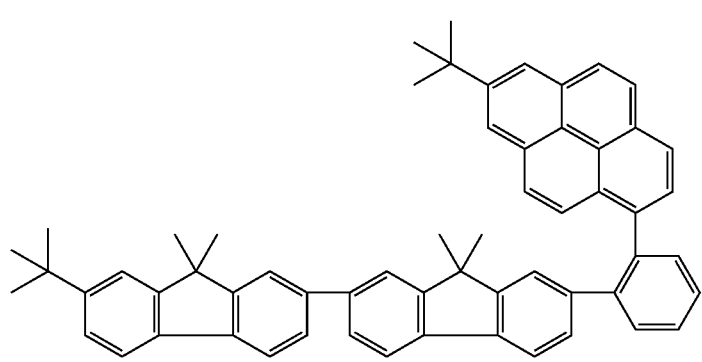
H6-4
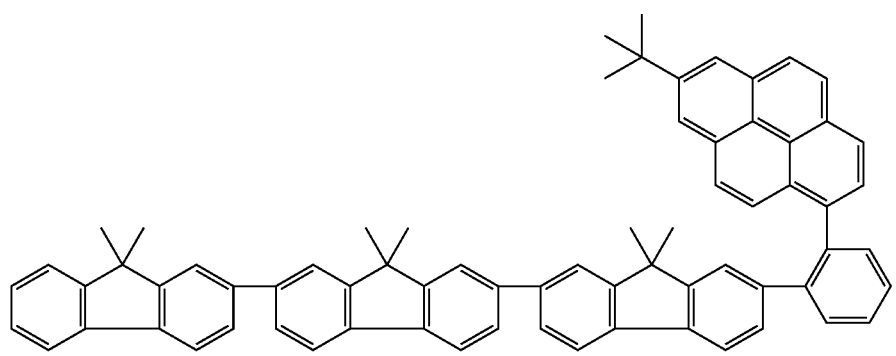
H6-5
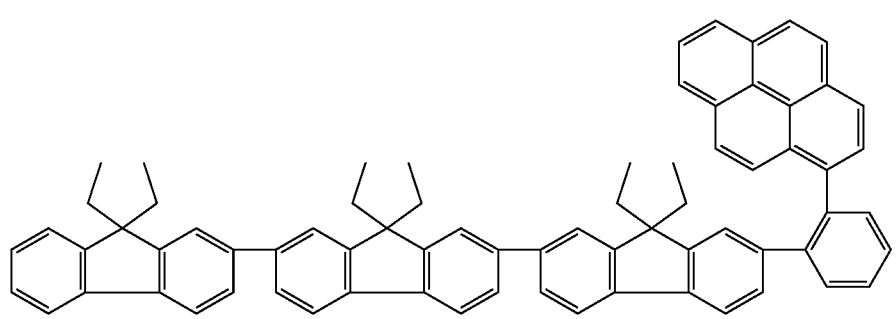

-continued
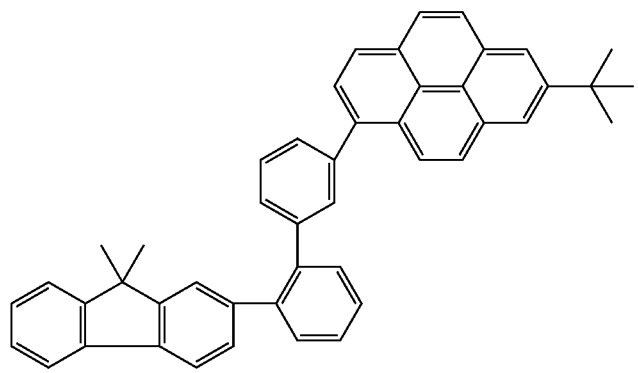
H6-6
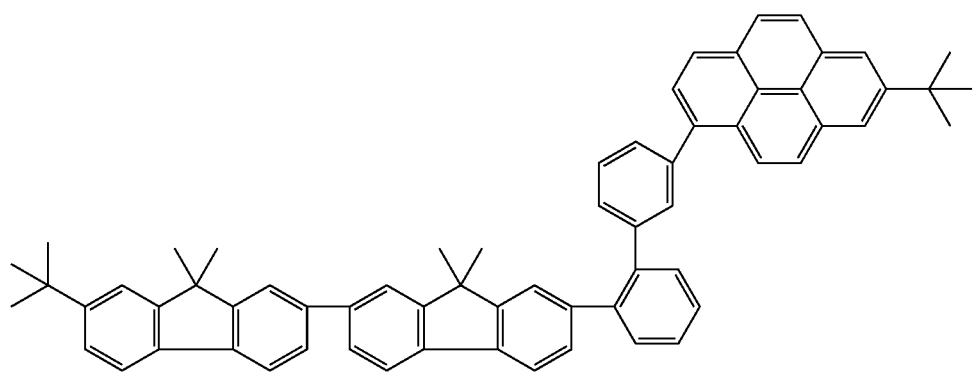
H6-7
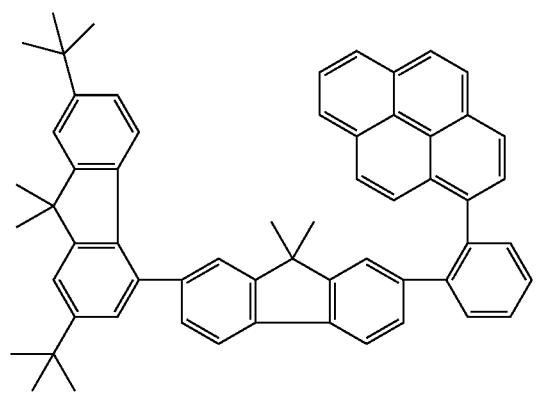
H6-8
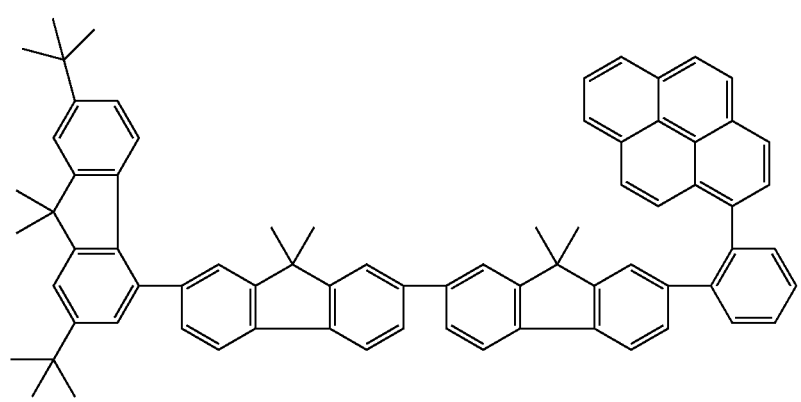
H6-9

-continued
H7
H7-1
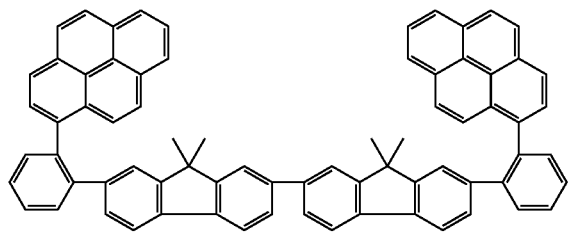
H7-2
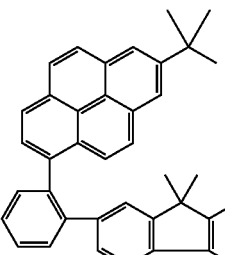 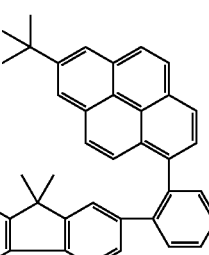
H7-3
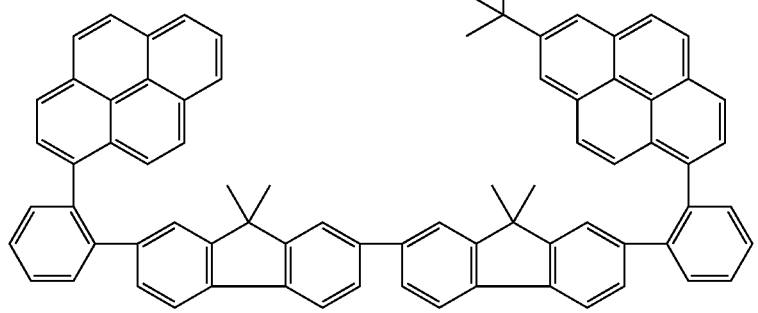
H7-4
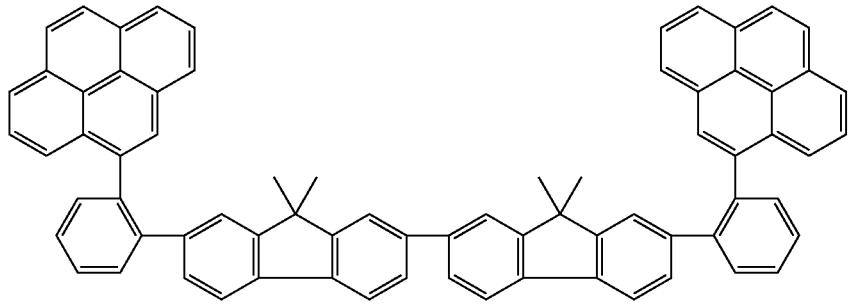
H7-5
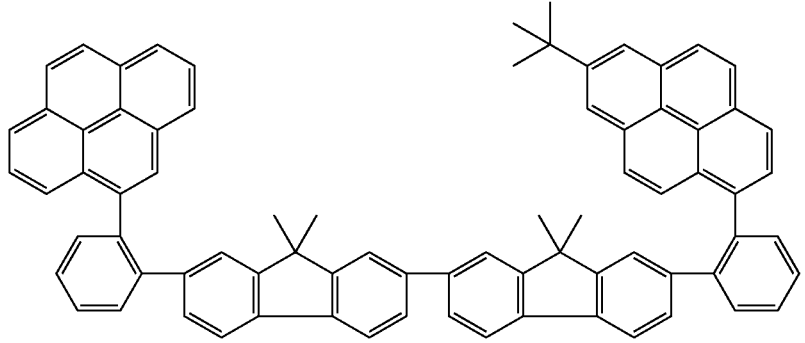
H7-6
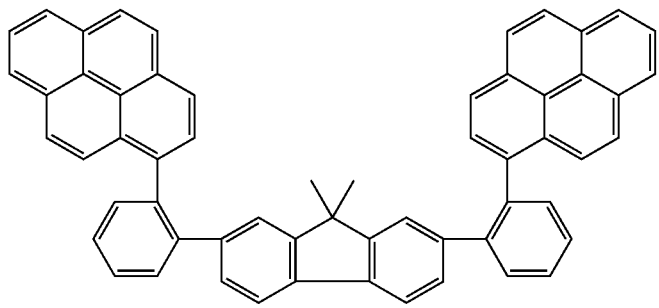

H7-7
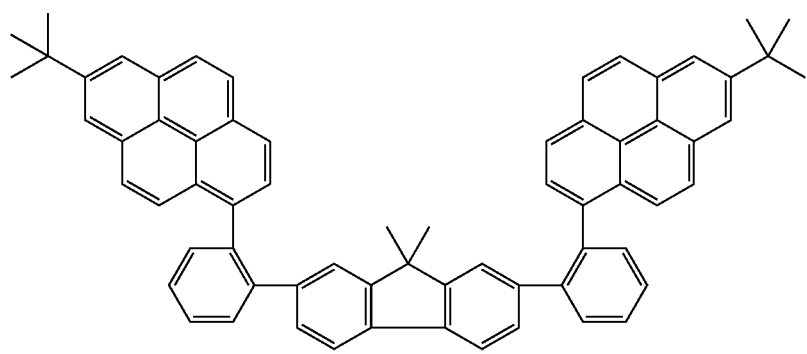
H7-8
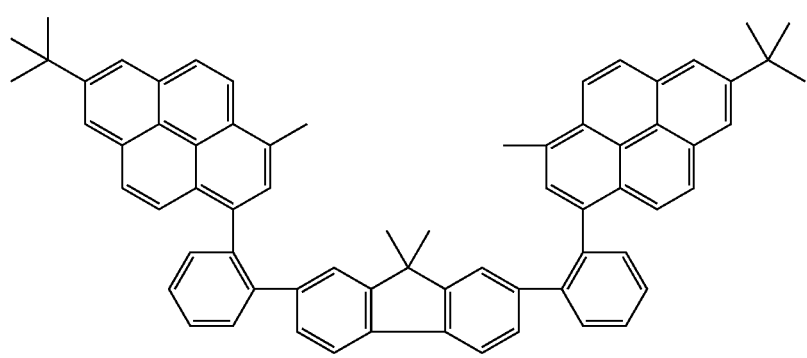
H7-9 H7-10
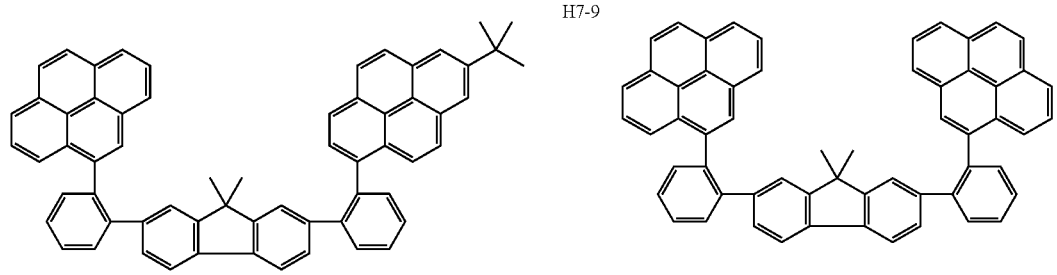
H8
H8-1
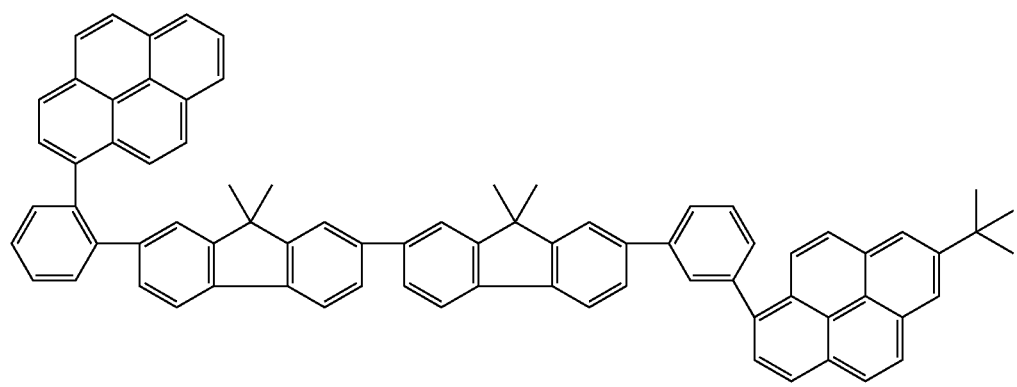

-continued
H8-2
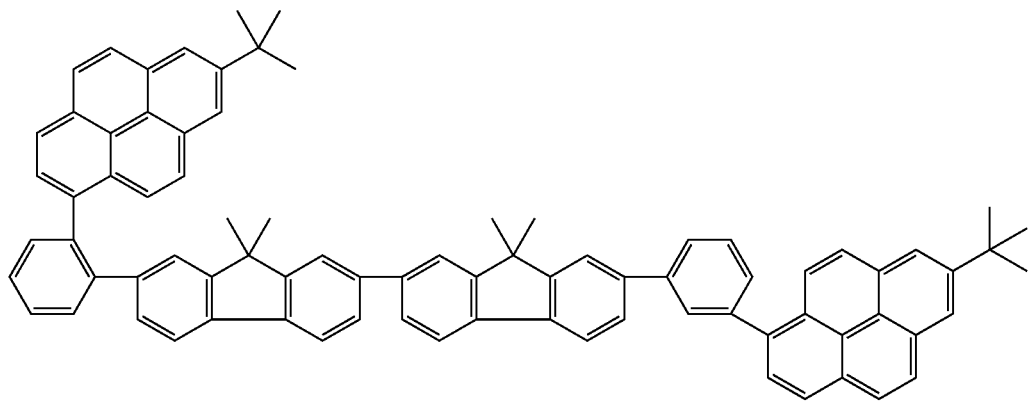
H8-3
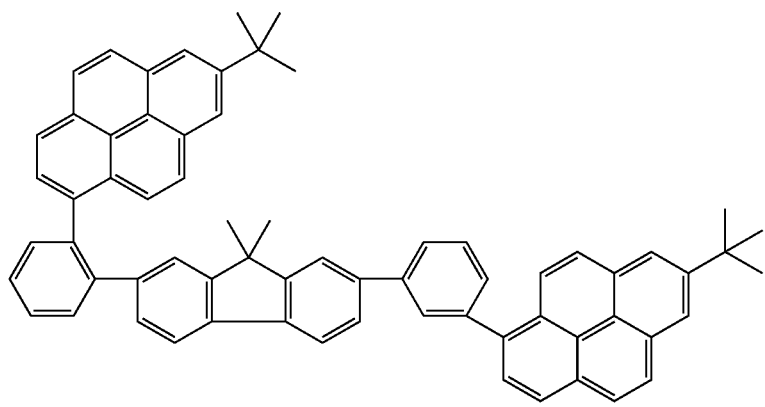
H8-4
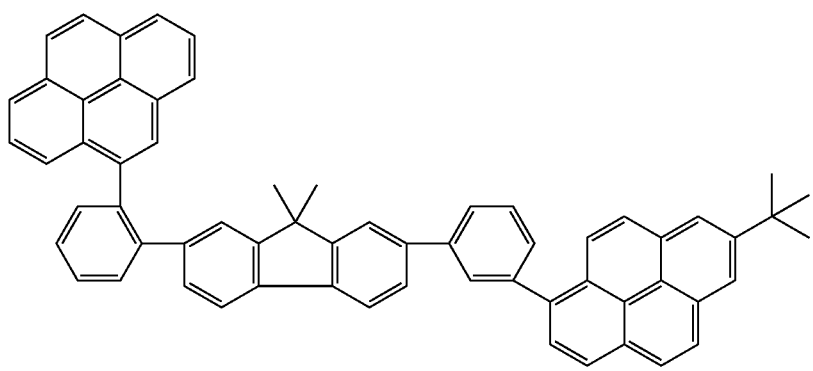
H9
H9-1
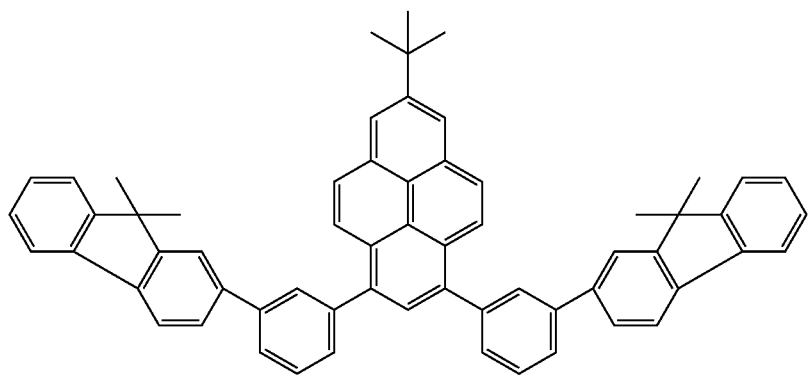

-continued
H9-2
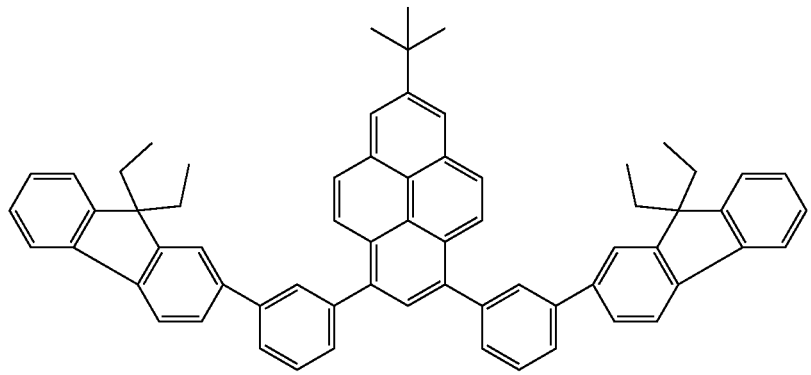
H9-3
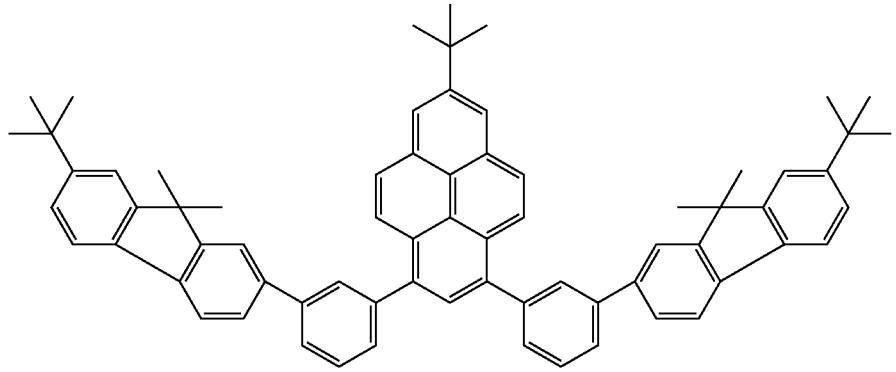
H9-4
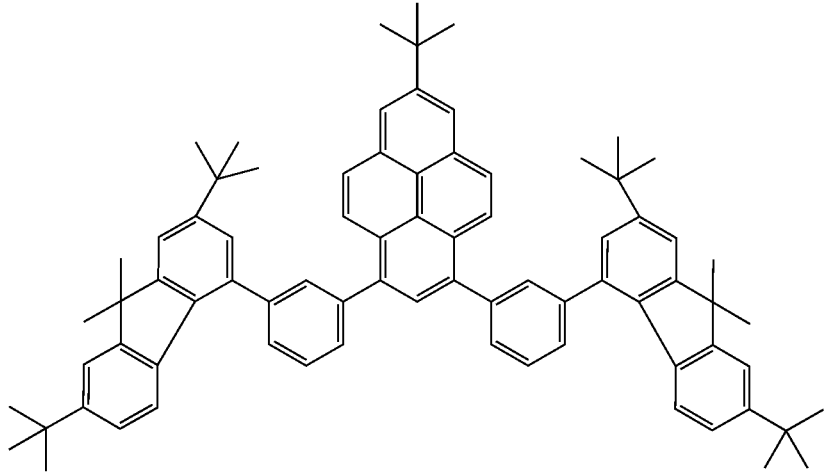
H9-5
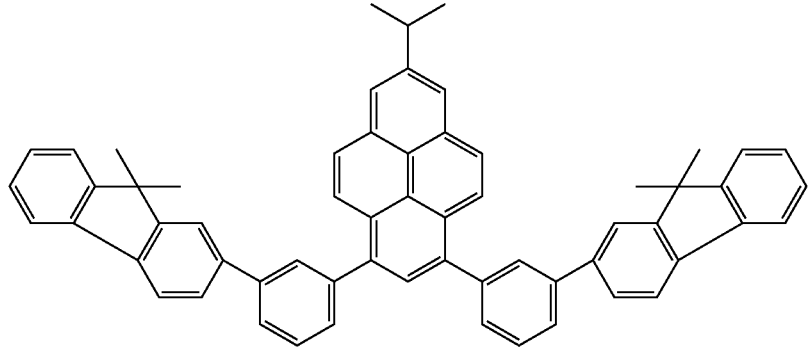

-continued
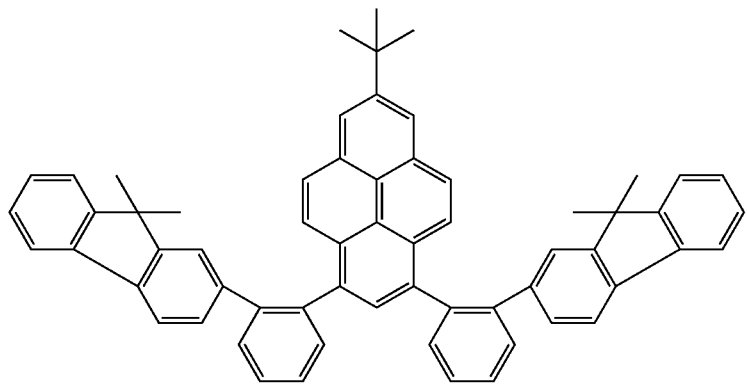
H9-6
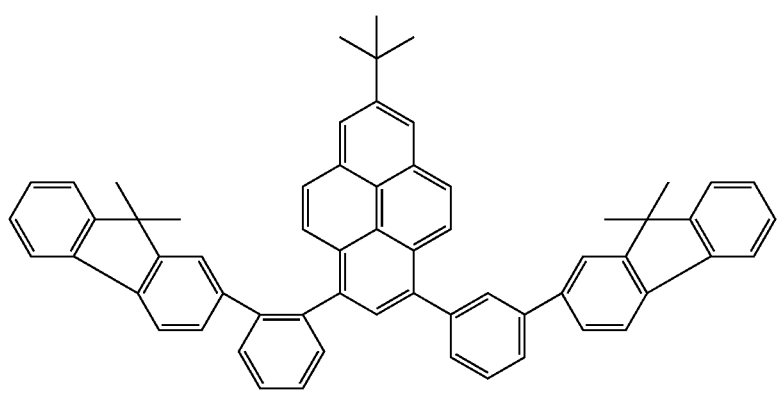
H9-7
Further, of the compound represented by the general formula (4), the compound wherein $Y_1$ and $Y_2$ are each independently a group selected from the groups represented by the general formulas (5) and (6) and at least one of $X_1$ and $X_2$ is a group other than the pyrene ring includes, but is not limited to, e.g., the following materials.
H10
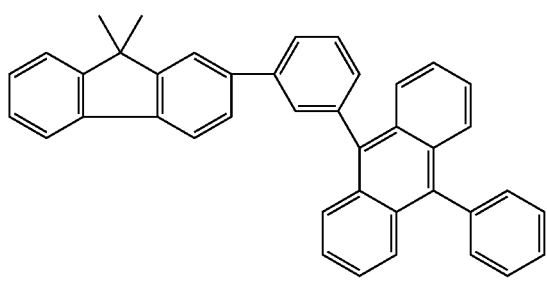
H10-1
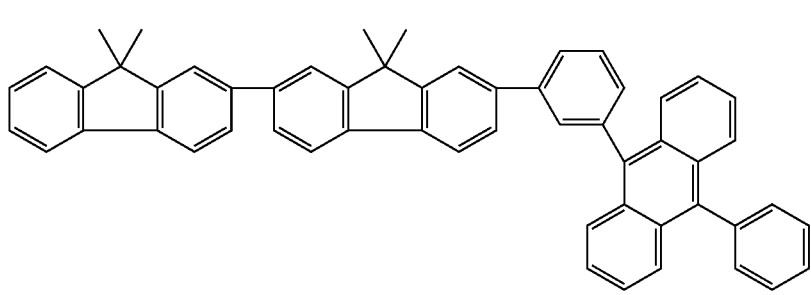
H10-2

-continued
H10-3
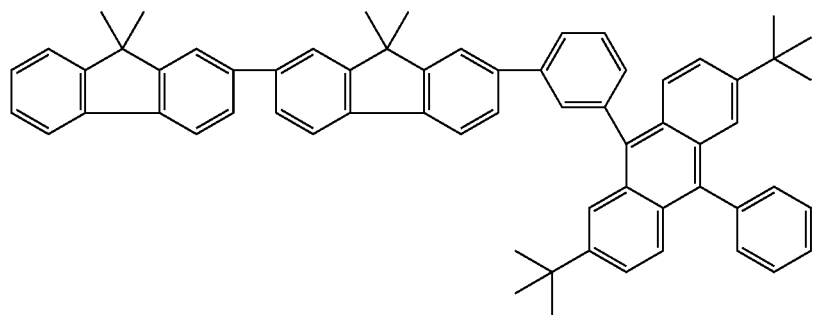
H10-4
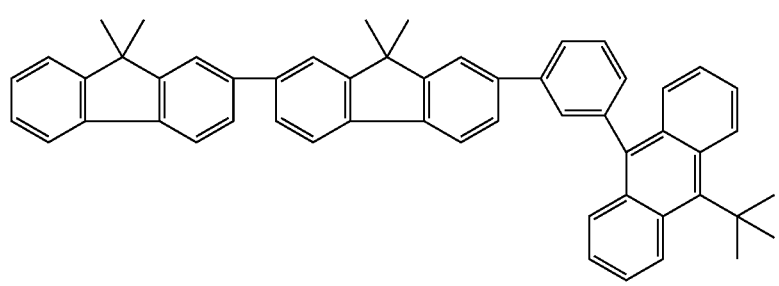
H10-5 H10-6
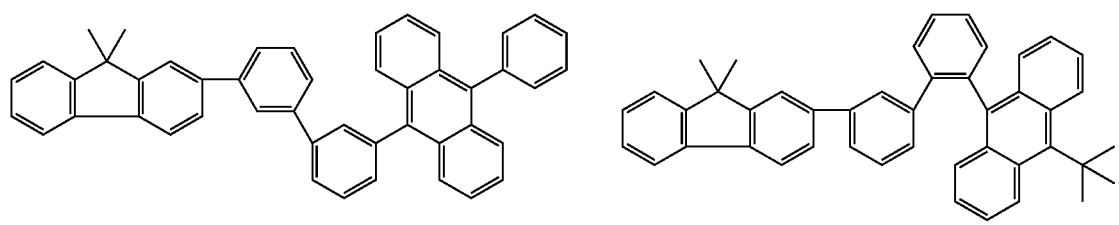
H10-7
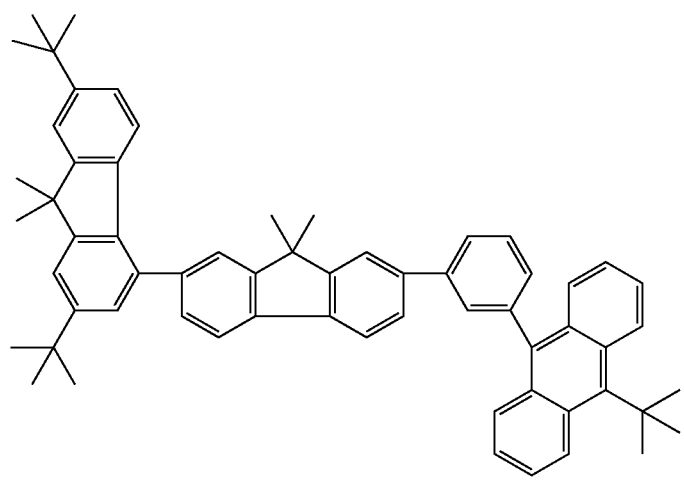
H10-8
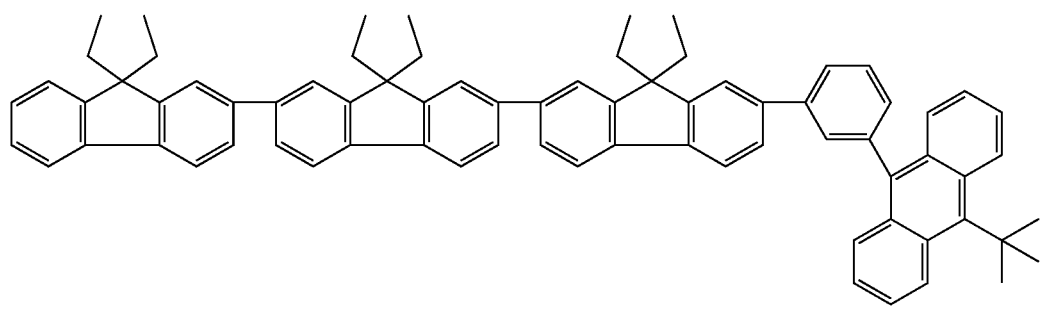

-continued
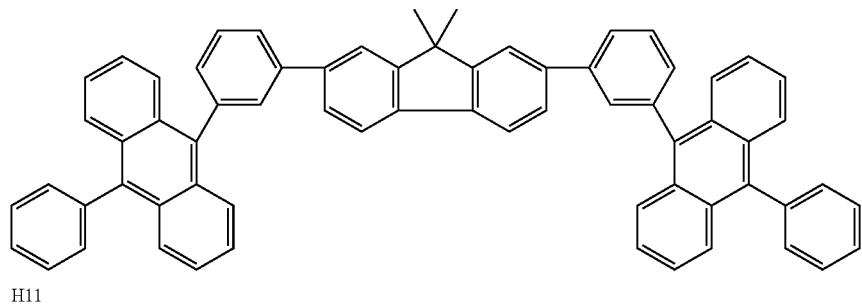
H11
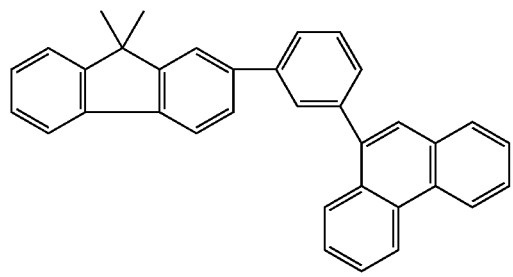
H11-1
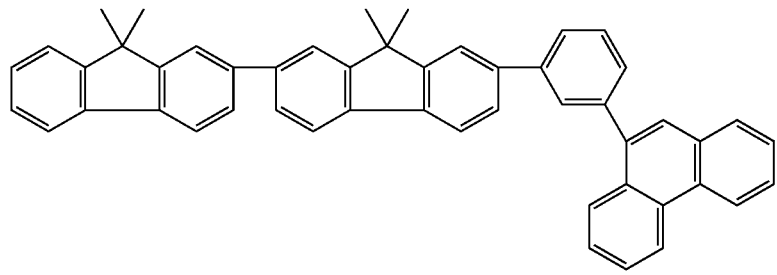
H11-2
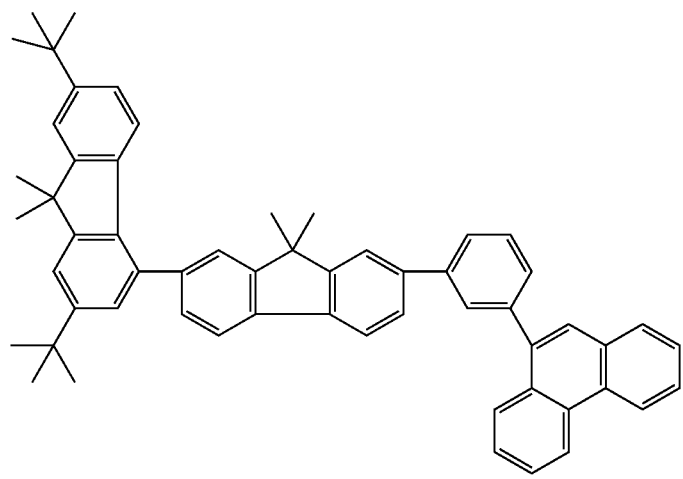
H11-3
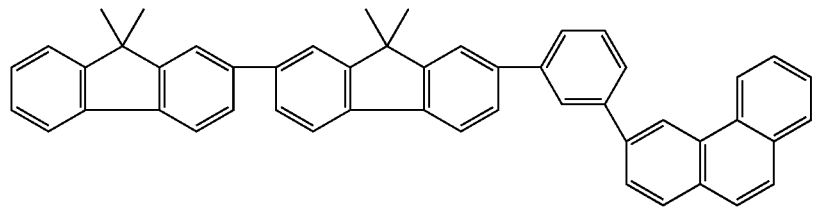
H11-4
H10-9

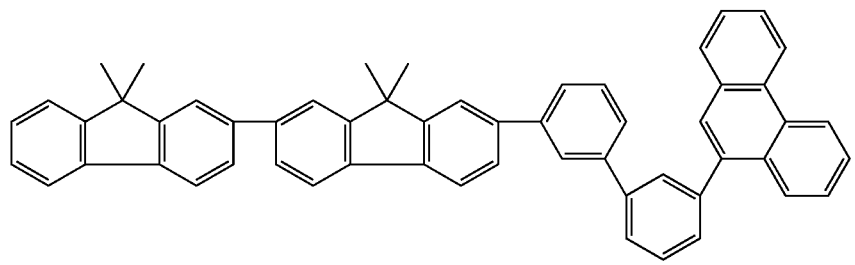
H11-5
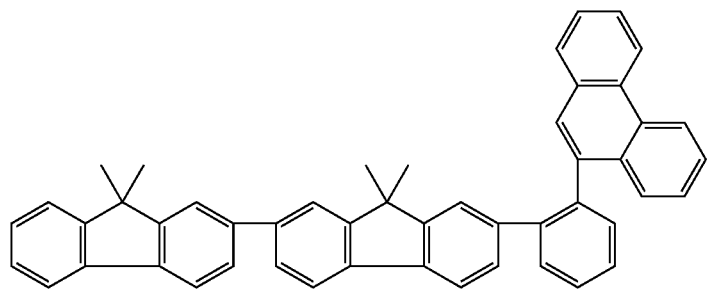
H11-6
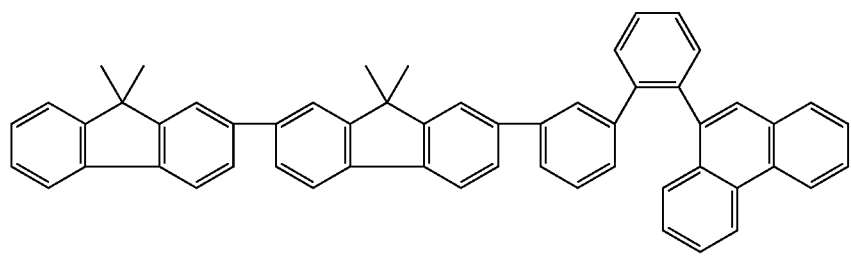
H11-7
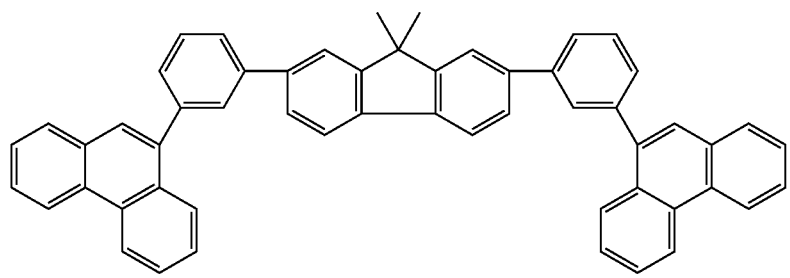
H11-8
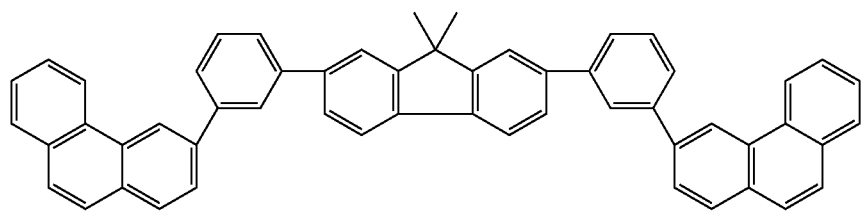
H11-9
H12
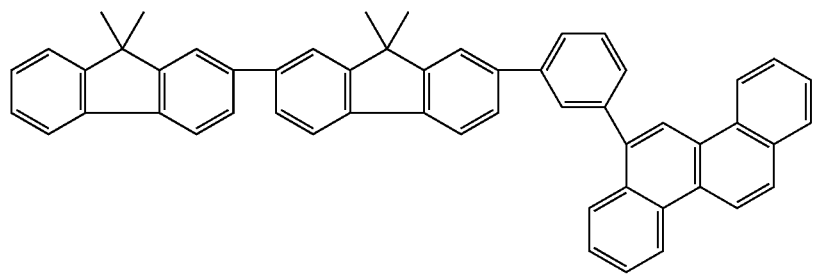
H12-1

-continued
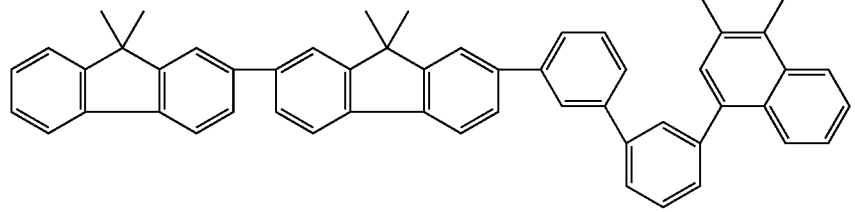
H12-2
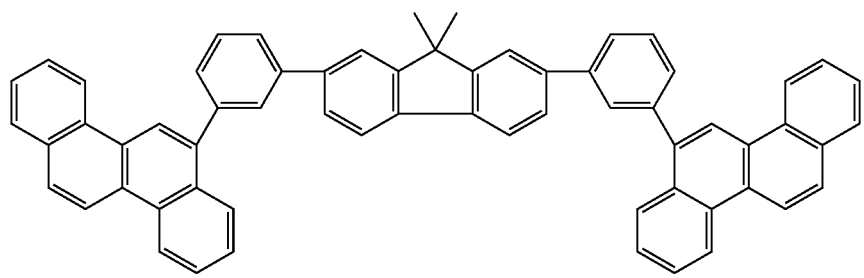
H12-3
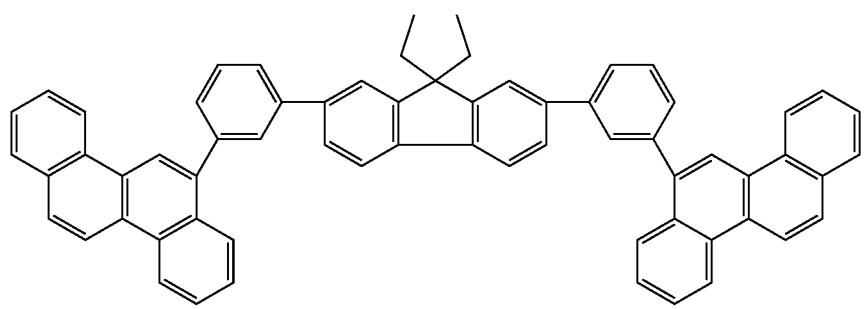
H12-4
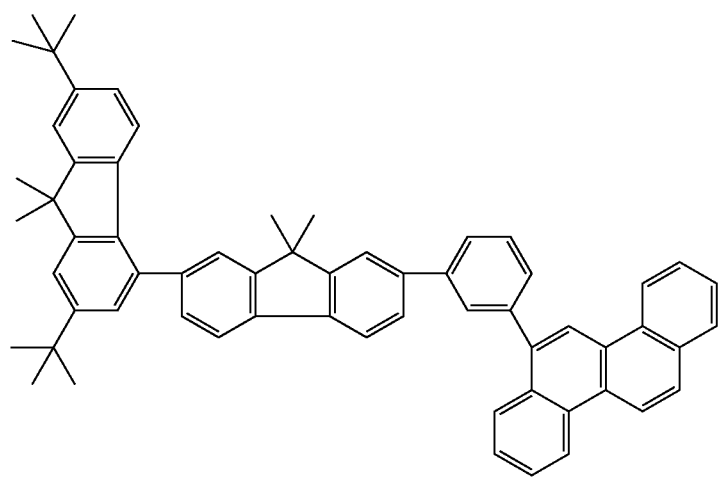
H12-5
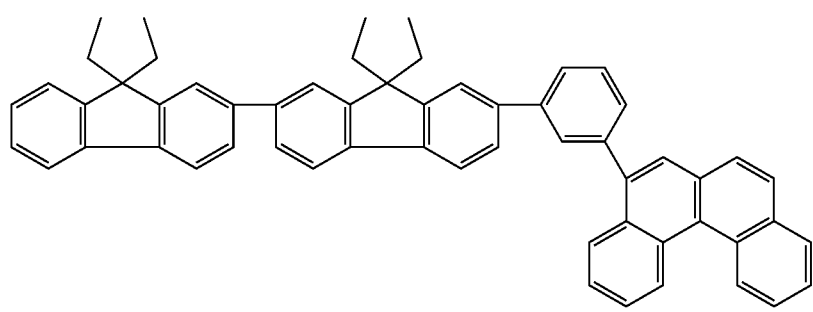
H12-6

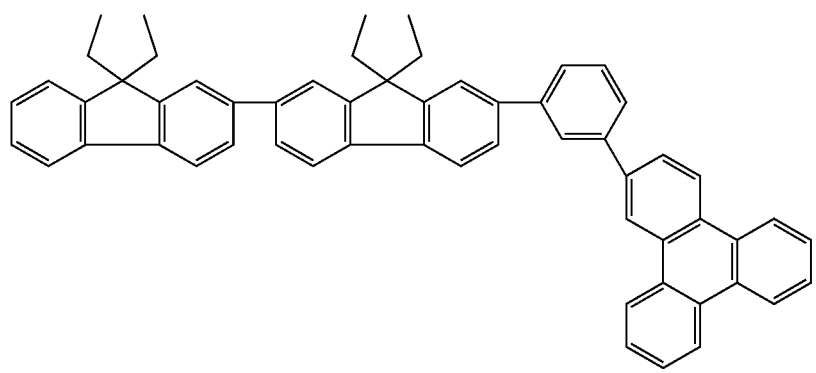
H12-7
Still further, of the compound represented by the general formula (4), the compound wherein one of $X_1$ and $X_2$ is a substituted or unsubstituted pyrene ring and the other is a condensed-ring hydrocarbon skeleton other than the pyrene ring includes, but is not limited to, e.g., the following materials.
H13
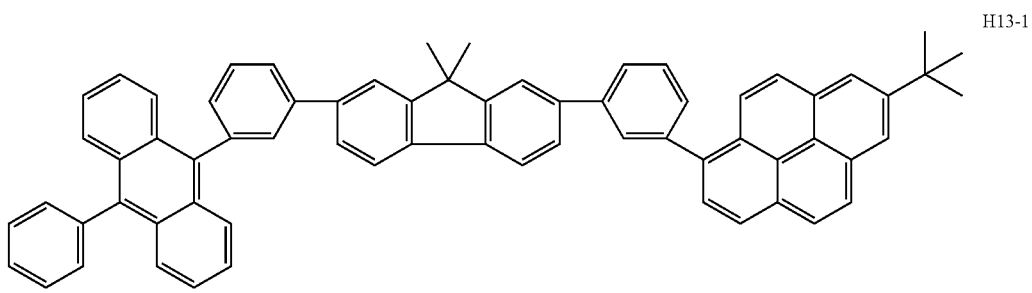
H13-1
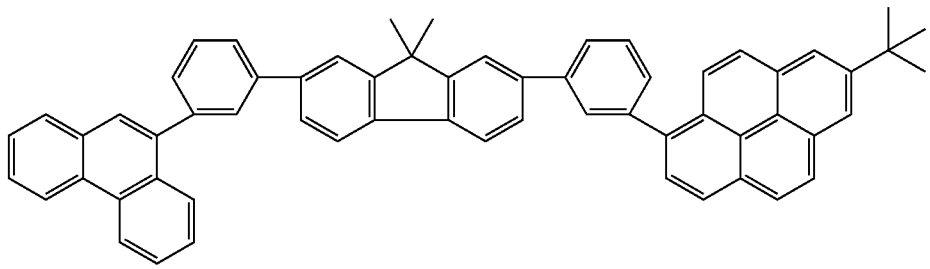
H13-2
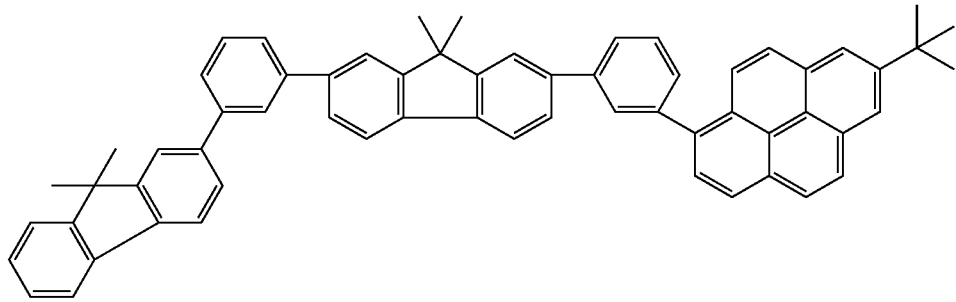
H13-3

-continued
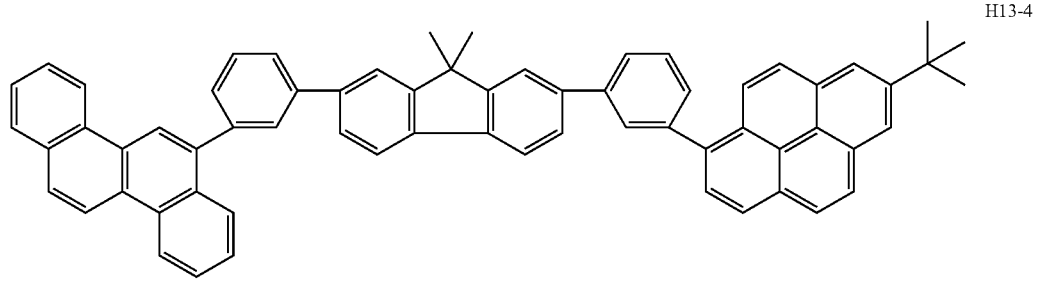
H13-4
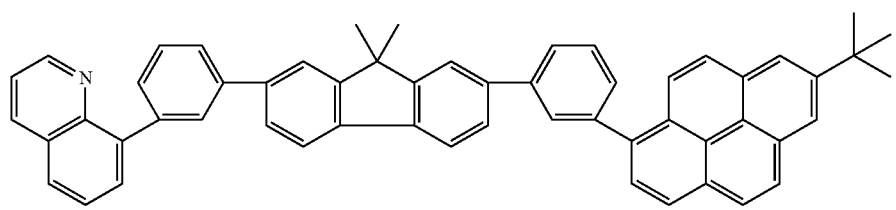
H13-5
Of the compound represented by the general formula (4), the compound wherein $Y_1$ and $Y_2$ are each independently a group selected from the groups represented by the general formula (7) and at least one of $X_1$ and $X_2$ is a substituted or unsubstituted pyrene ring includes, but is not limited to, e.g., the following materials.
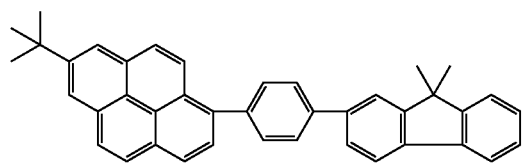
H14-1
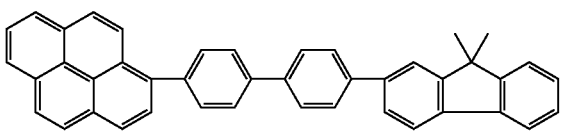
H14-2
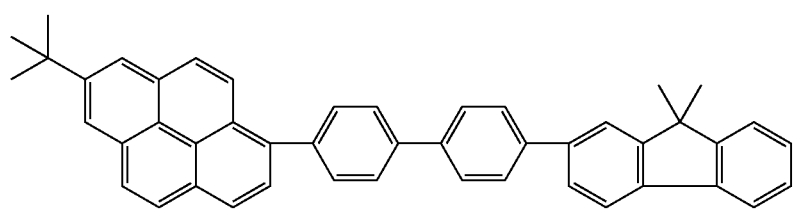
H14-3
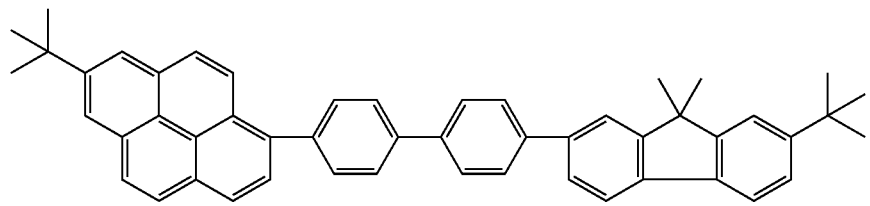
H14-4
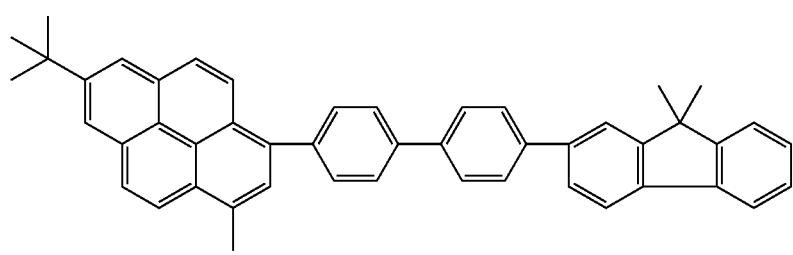
H14-5

H14-6
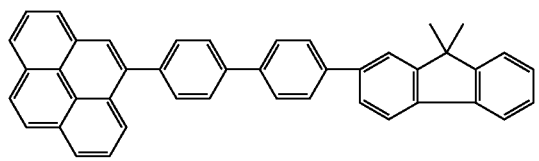
H14-7
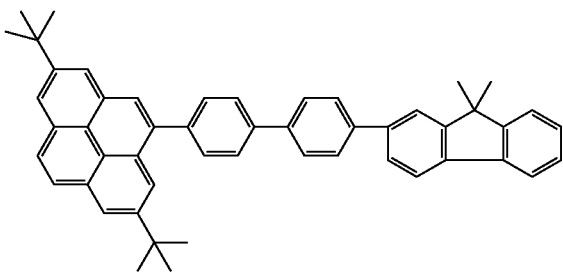
H14-8
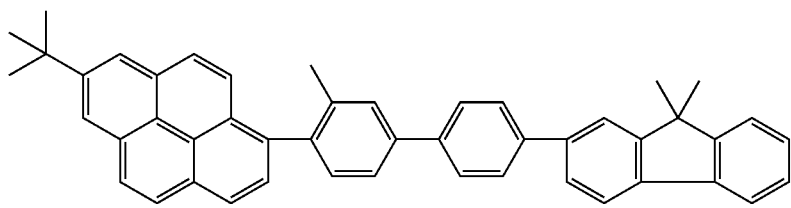
H14-9
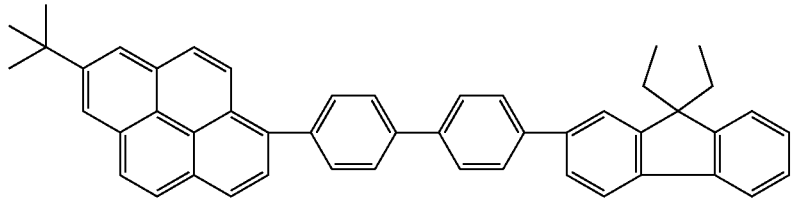
H14-10
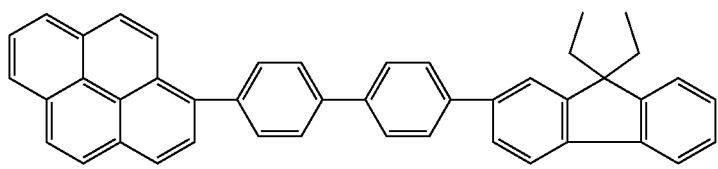
H14-11
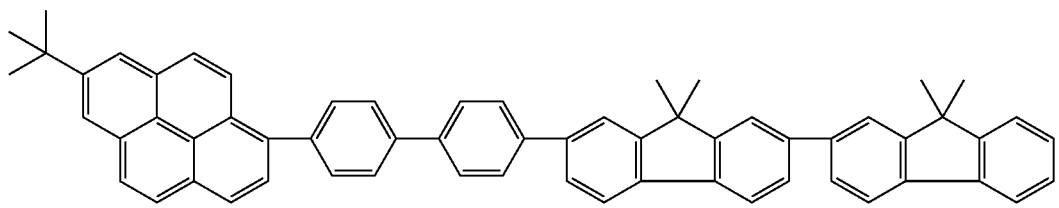
H14-12
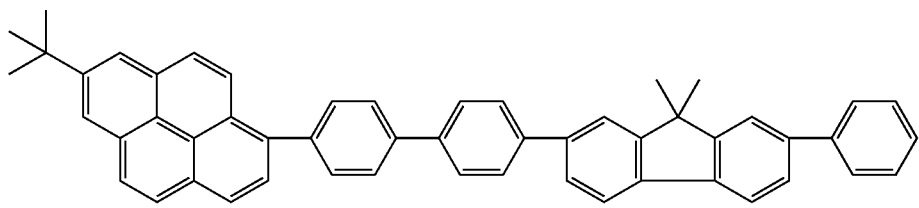
H14-13
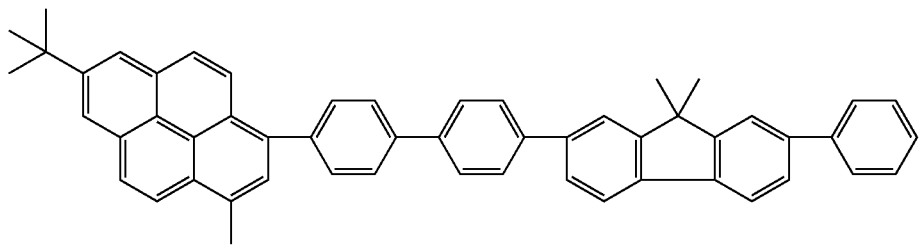

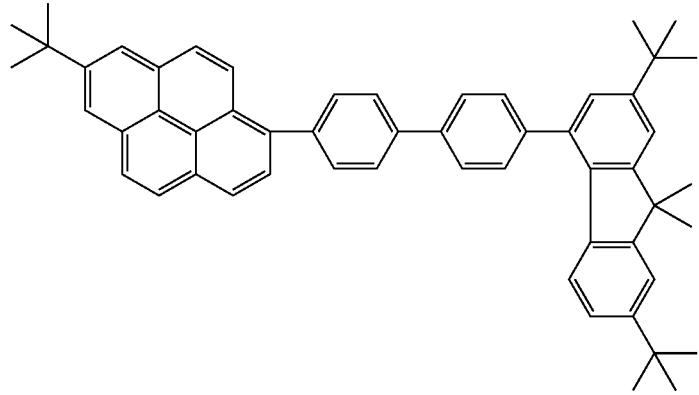
H14-14
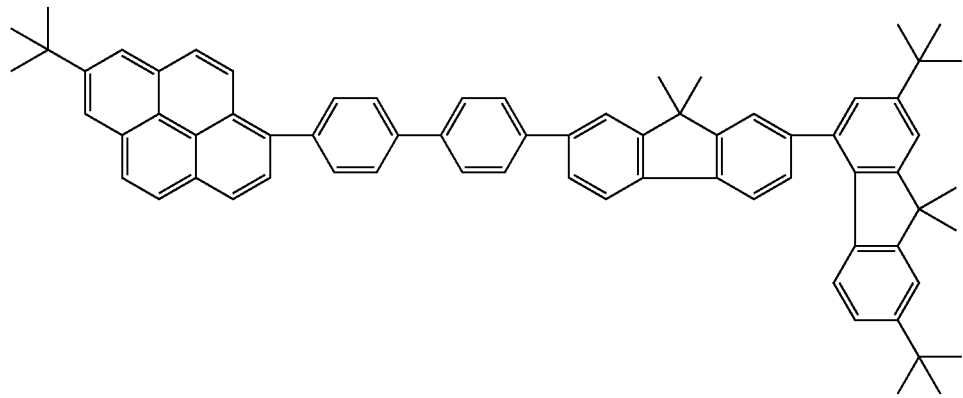
H14-15
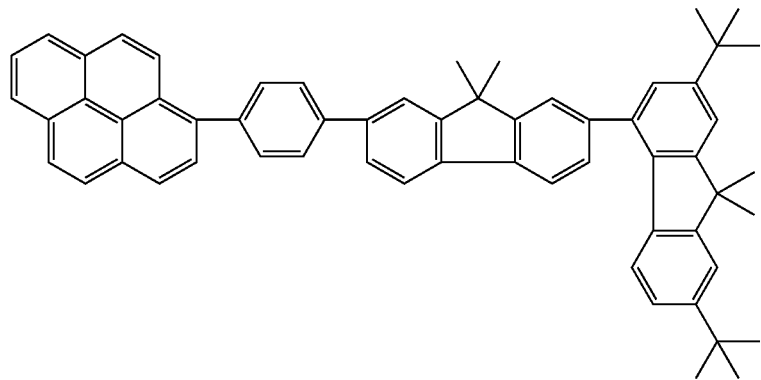
H14-16
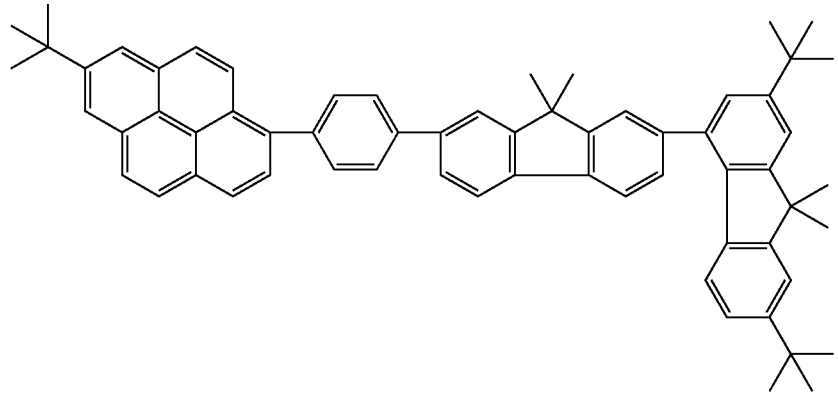
H14-17

H14-18
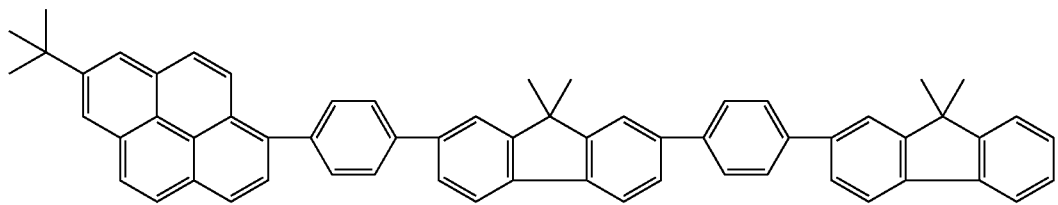
H14-19
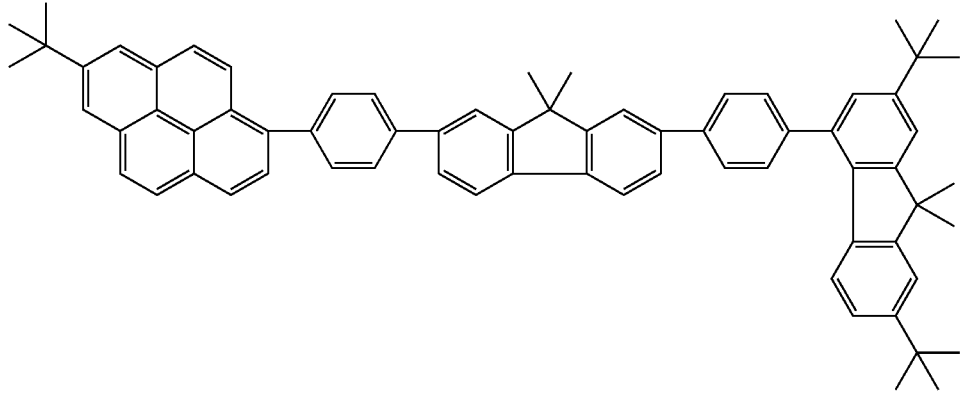
Further, of the compound represented by the general formula (4), the compound wherein $Y_1$ and $Y_2$ are each independently a group selected from the groups represented by the general formulas (5) to (7) and at least one of $X_1$ and $X_2$ is a pyrene ring includes, but is not limited to, e.g., the following materials.
H15-1
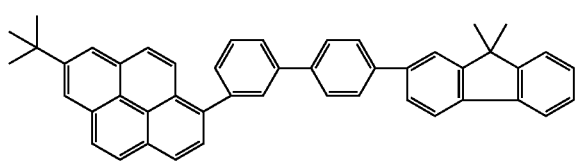
H15-2
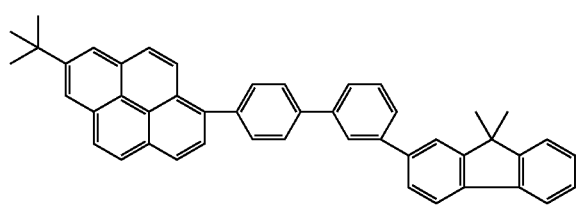
H15-3
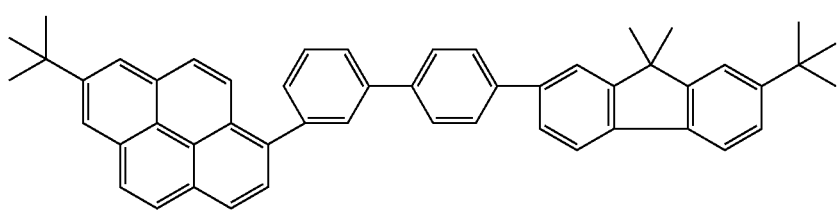
H15-4
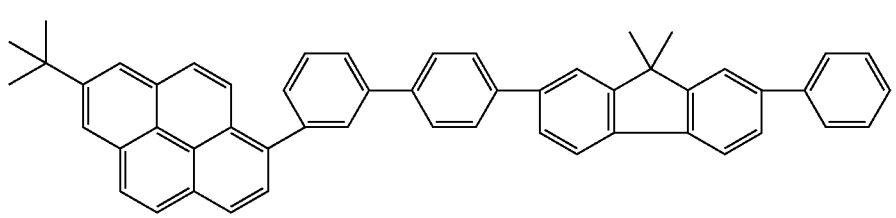

H15-5
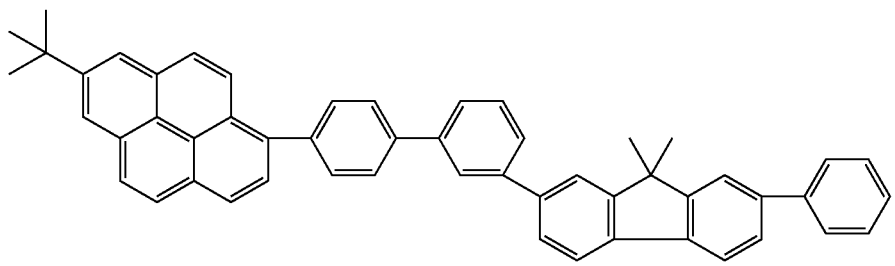
H15-6
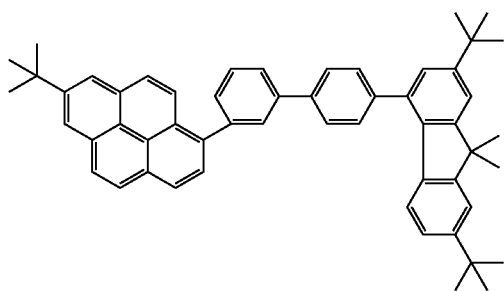
H15-7
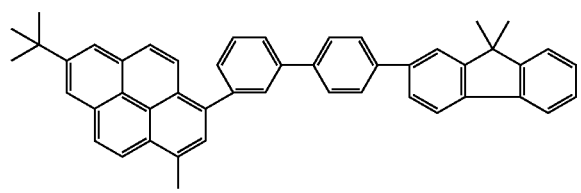
H15-8
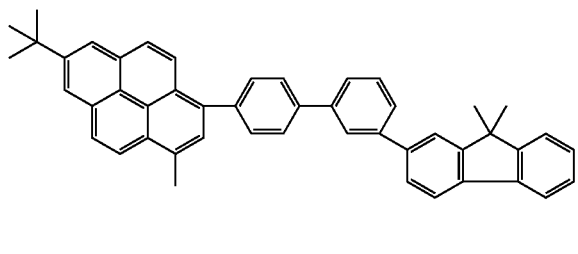
H15-9
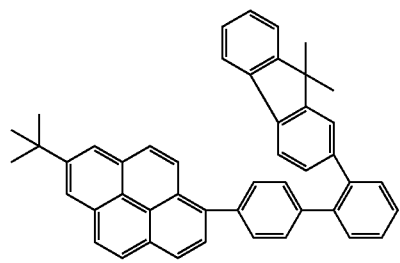
Still further, of the compound represented by the general formula (4), the compound wherein Y₁ and Y₂ are each independently a group selected from the groups represented by the general formula (7) and at least one of X₁ and X₂ is a group other than a pyrene ring includes, but is not limited to, e.g., the following materials.
H16-1
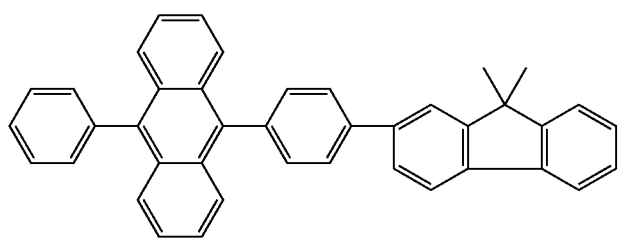
H16-2
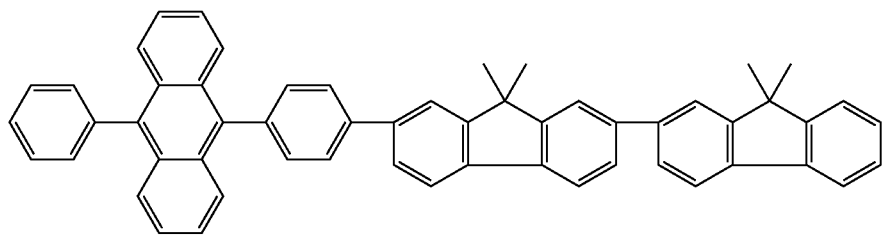

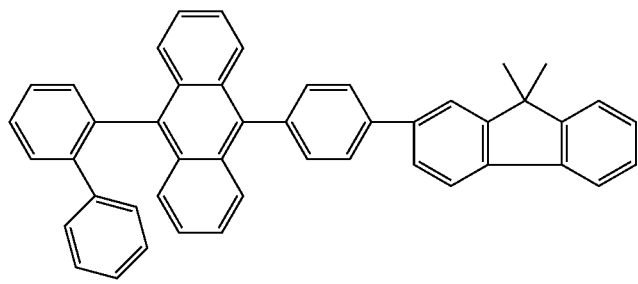
H16-3
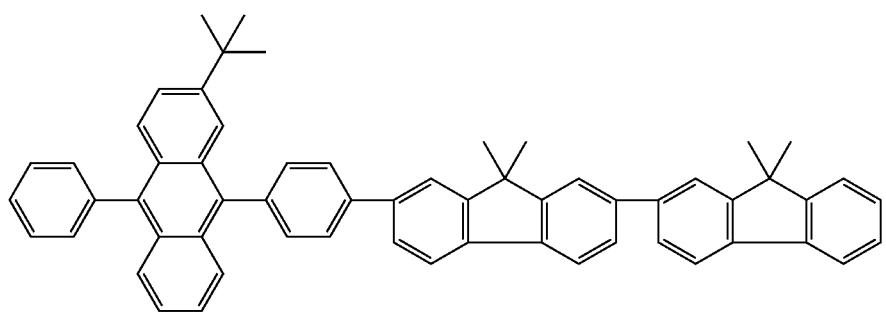
H16-4
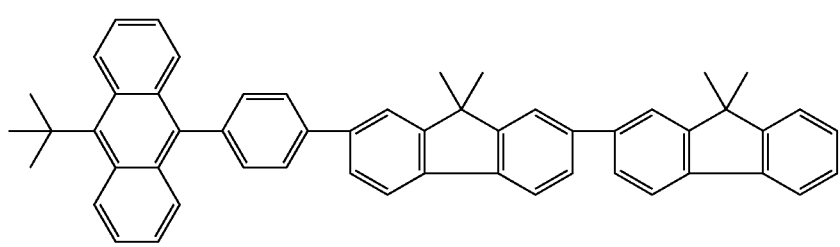
H16-5
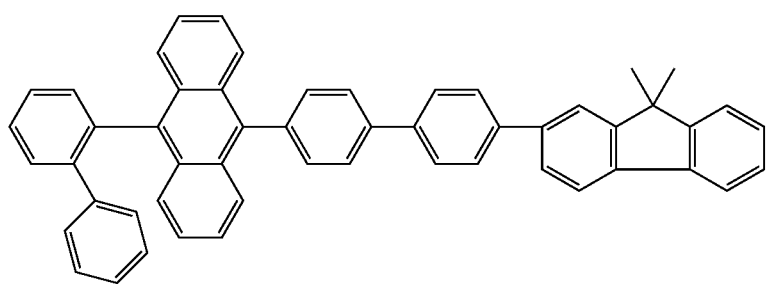
H16-6
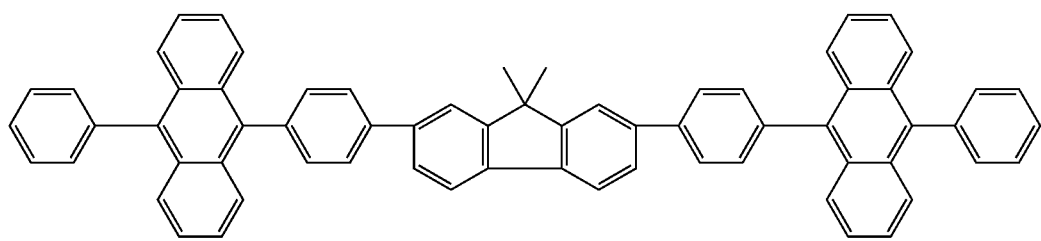
H16-7
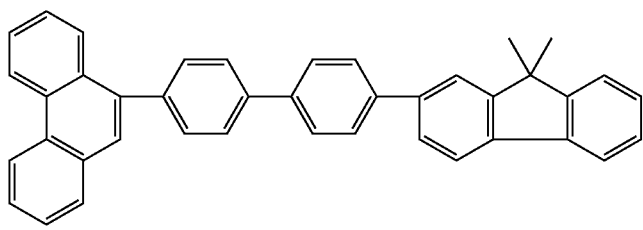
H16-8

-continued
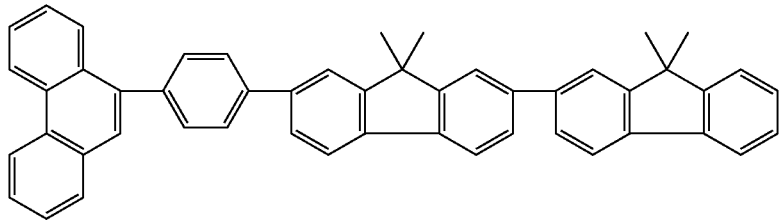
H16-9
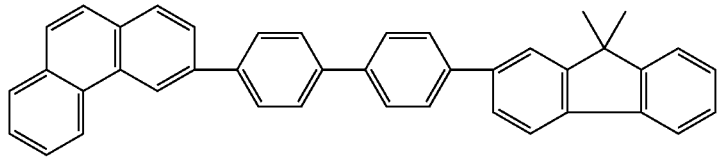
H16-10
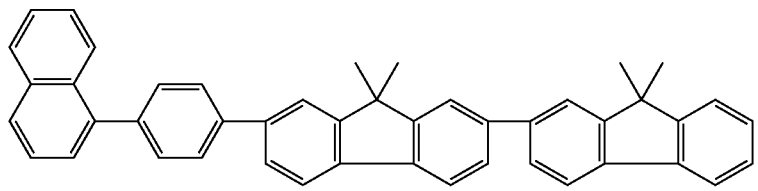
H16-11
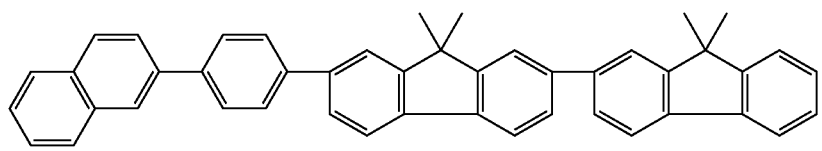
H16-12
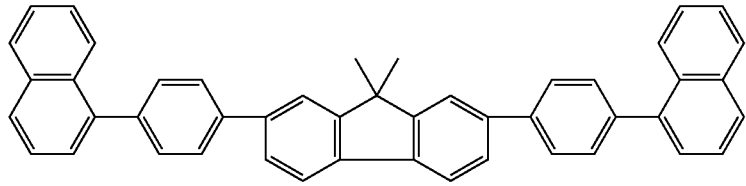
H16-13
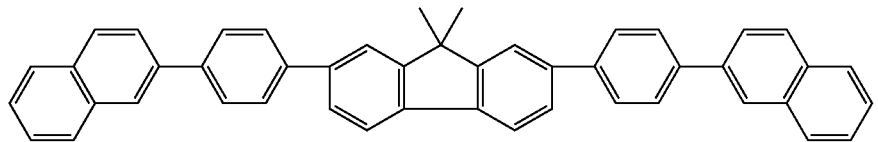
H16-14
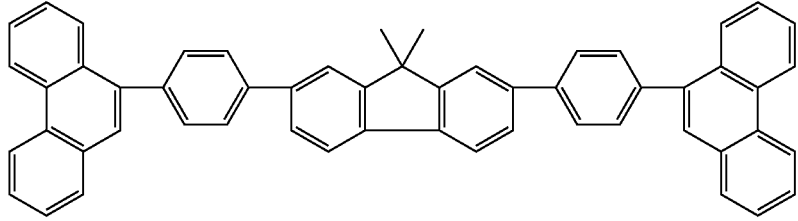
H16-15
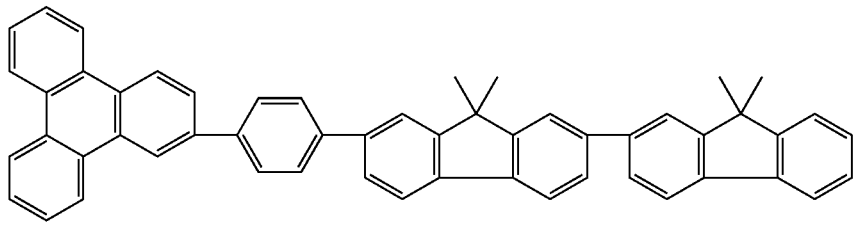
H16-16

-continued
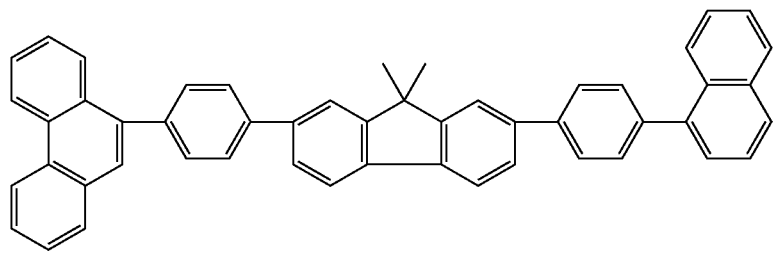
H16-17
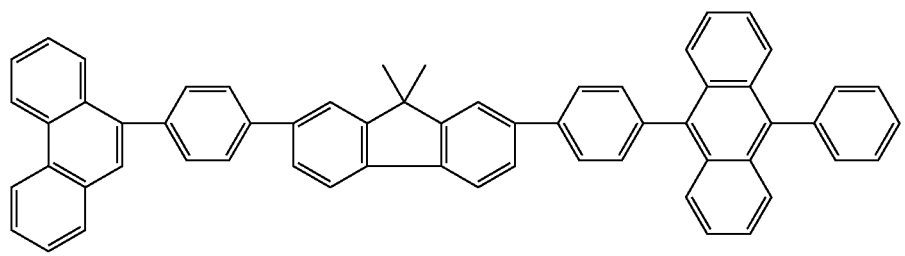
H16-18
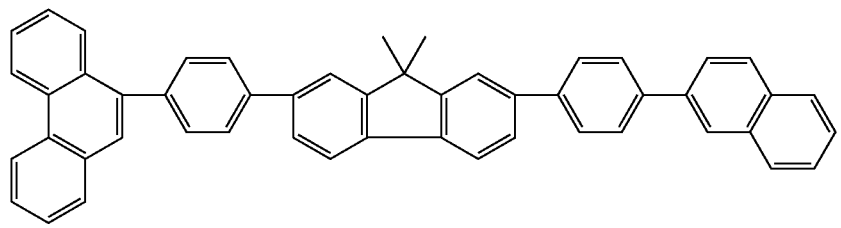
H16-19
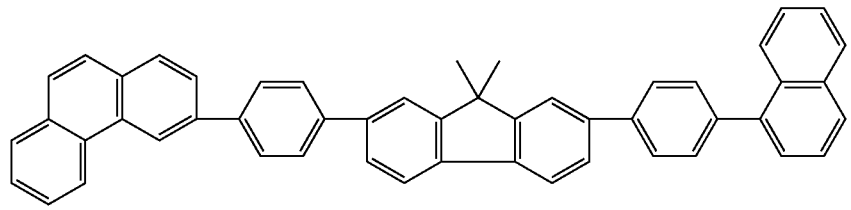
H16-20
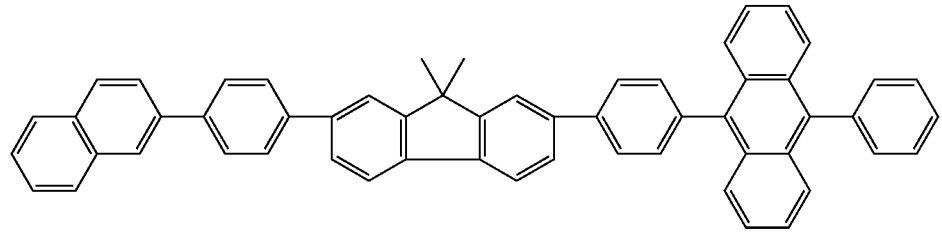
H16-21
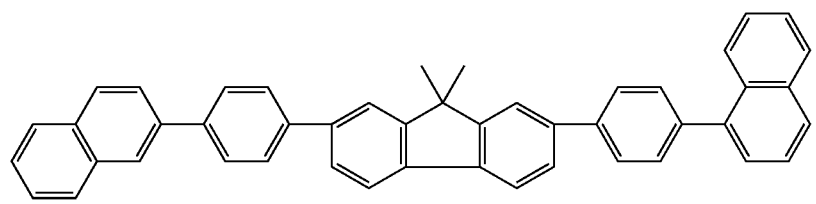
H16-22

Still further, of the compound represented by the general formula (4), the compound wherein $Y_1$ and $Y_2$ are each independently a group selected from the groups represented by the general formula (7) and one of $X_1$ and $X_2$ is a substituted or unsubstituted pyrene ring and the other is a condensed-ring hydrocarbon skeleton other than a pyrene ring may include, but is not limited to, e.g., the following materials.

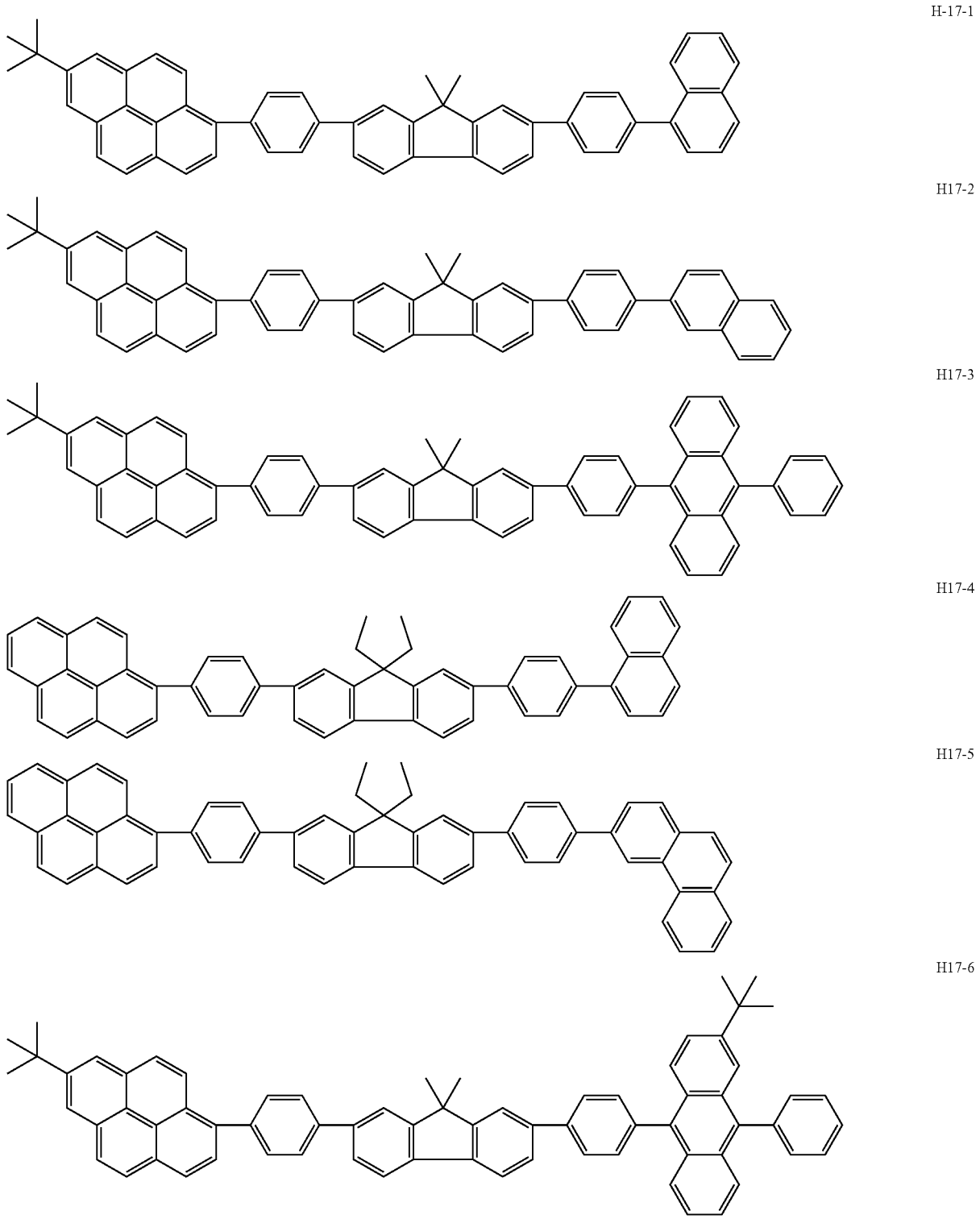

Where the benzo[k]fluoranthene compound of the present invention is used as a dopant material, the dopant concentration is 0.01% by mass or more and 80% by mass or less, and preferably 1% by mass or more and 40% by mass or less, based on the mass of the host material. The dopant material may be contained uniformly, or with a concentration gradient, in the whole layer formed of the host material, or may partially be contained in some regions to form regions of a host material layer containing no dopant material.

Figure 1:
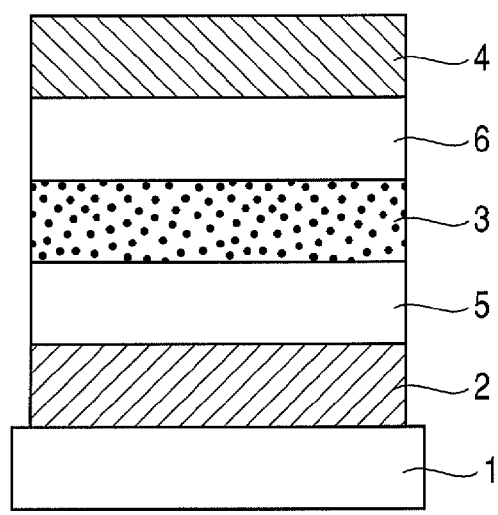
FIG. 1 is a sectional view showing an example of the organic luminescent device in the present invention.

FIG. 1 illustrates a preferred example of the organic luminescent device of the present invention.

Reference characters shown in the drawings denote: 1, a substrate; 2, an anode; 3, a luminescent layer; 4, a cathode; 5, a hole transport layer; and 6, an electron transport layer.

FIG. 1 is a sectional view showing an example of the organic luminescent device of the present invention, which is constituted of a substrate 1, and an anode 2, a hole transport layer 5, a luminescent layer 3, an electron transport layer 6 and a cathode 4 in this order provided on the substrate. This device is one in which the functions of carrier transport and luminescence are separated, and is used in appropriate combination with a compound having each of a hole transport property, an electron transport property and a luminescence property. The degree of freedom of material selection is increased and various compounds different in luminescence wavelength can be used, and Hence, a variety of luminescence hues can be achieve. In addition, carriers or excitons can be effectively confined in the central luminescent layer 3 to achieve an improvement in luminous efficiency.

As an example other than what is shown in FIG. 1, a device may be cited which is constituted of a substrate 1, and an anode 2, a luminescent layer 3 and a cathode 4 in this order provided on the substrate. The luminescent device used in this case is useful where the device itself has hole transportability, electron transportability and luminescence performance, or where compounds having the respective properties are used in the form of a mixture.

In the case of what is constituted of a substrate 1, and an anode 2, a hole transport layer 5, an electron transport layer 6 and a cathode 4 in this order provided on the substrate, a material having either of hole transport function or electron transport function or both of them is used as a luminescent material in any one of the layers. This device is useful where such a material is used in combination with a mere hole transporting material or electron transporting material having no luminescent property. Also in this case, the luminescent layer consists of either of the hole transport layer 5 or the electron transport layer 6.

Besides, what is shown in FIG. 1 may be so constituted as to be provided with a hole injection layer inserted on the anode 2 side. This is effective in improving adherence between the anode 2 and the hole transport layer 5 and improving hole injection, and is effective in low-voltage luminescence.

Further, what is shown in FIG. 1 may be so constituted as to be provided with a layer (hole/exciton blocking layer) which is inserted between the luminescent layer 3 and the electron transport layer 6 to prevent holes or excitons from passing through toward the cathode 4 side. A compound having a very high ionization potential may be used in the hole/exciton blocking layer to provide a constitution very effective in improving luminous efficiency.

The device constitution given in FIG. 1 and the foregoing show very basic constitutions, and the constitution of the organic luminescent device using the compound of the present invention is by no means limited thereto. For example, the device may have various constitutions such that an insulating layer is provided at the interface between an electrode and an organic layer, an adhesive layer or an interference layer is provided, and the hole transport layer is constituted of two layers different in ionization potential.

The organic luminescent device of the present invention may be used in any forms of the device constitution given in FIG. 1 and the foregoing.

In particular, an organic layer using the benzo[k]fluoranthene compound of the present invention is useful as the luminescent layer, the electron transport layer or the hole transport layer. A layer formed by vacuum deposition (vacuum evaporation) or solution coating can not easily be crystallized and has a superior stability over time.

In the present invention, the above benzo[k]fluoranthene compound is used as a constituent of, in particular, the luminescent layer, and may optionally be used together with a hole transporting compound, a luminescent compound and/or an electron transporting compound which are/is of a low molecular type or polymer type hitherto known in the art.

Examples of such compounds are given below.

It is preferable that a hole injecting and transporting material facilitates the injection of holes from the anode and has mobility good enough to transport the injected holes to the luminescent layer. Low-molecular and high-molecular materials having hole injection and transport functions include, but is not limited to, the following:

Triarylamine derivatives, phenylenediamine derivatives, triazole derivatives, oxadiazole derivatives, imidazole derivatives pyrazoline derivatives, pyrazolone derivatives, oxazole derivatives, fluorenone derivatives, hydrazone derivatives, stilbene derivatives, phthalocyanine derivatives, porphyrin derivatives, poly(vinylcarbazole), poly(silylene), poly(thiophene), and other conductive high-molecular materials.

Materials concerned chiefly in a luminescence function which are usable besides the compounds used in the organic luminescent device of the present invention includes, but are not limited to, the following:

High-molecular derivatives such as polycyclic condensation aromatic compounds (e.g., naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, and rubrene), quinacridone derivatives, acridone derivatives, coumarine derivatives, pyrane derivatives, Nile Red, pyrazine derivatives, benzoimidazole derivatives, benzothiazole derivatives, benzoxazole derivatives, stilbene derivatives, organometallic complexes (e.g., organoaluminum complexes such as tris(8-quinolinolato)aluminum, and organoberyllium complexes), poly(phenylenevinylene) derivatives, poly(fluorene) derivatives, poly(phenylene) derivatives, poly(thienylenevinylene) derivatives, and poly(acetylene) derivatives.

An electron injecting and transporting material may be selected from materials which facilitate the injection of electrons from the cathode and have a function to transport injected electrons to the luminescent layer, taking into account, e.g., a balance with the carrier mobility of the hole transporting material. Materials having electron injection and transport functions include, but is not limited to, the following:

Oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organometallic complexes.

In the organic luminescent device of the present invention, the layer containing the benzo[k]fluoranthene compound of the present invention and the layers formed of other organic compounds are formed by any of methods shown below. The layers are commonly formed by forming thin films by means of vacuum deposition, ionization deposition, sputtering, plasma deposition or known application (e.g., spin coating, dipping, casting, the LB (Langmuir Blodgett) process, or ink-jet printing) of a coating material prepared by dissolving a material in a suitable solvent. Especially when the films are formed by coating, they may be formed using materials in combination with a suitable binder resin.

The binder resin may be selected from extensive binding resins, and includes, but is not limited to, the following:

Polyvinyl carbazole resins, polycarbonate resins, polyester resins, polyarylate resins, polystyrene resins, ABS resins, polybutadiene resins, polyurethane resins, acrylic resins, methacrylic resins, butyral resins, polyvinyl acetal resins, polyamide resins, polyimide resins, polyethylene resins, polyether sulfone resins, diallyl phthalate resins, phenol resins, epoxy resins, silicone resins, polysulfone resins, and urea resins.

These may be used alone or in the form of a mixture of two or more types as copolymers. Additives such as known plasticizers, antioxidants and ultraviolet absorbers may optionally be used in combination.

Materials for the anode having a work function as large as possible are favorable. For example, the following is usable: metal simple substances such as gold, platinum, silver, copper, nickel, palladium, cobalt, selenium, vanadium and tungsten, or alloys of any of these; and metal oxides such as tin oxide, zinc oxide, indium oxide, indium-tin oxide (ITO), and indium-zinc oxide. Also, it is possible to use conductive polymers such as polyaniline, polypyrrole, polythiophene, and polyphenylene sulfide. Any of these electrode materials may be used alone or in a combination of two or more types. The anode may be constituted of a single layer or a multiple layer.

Materials for the cathode having a small work function are favorable. For example, the following are usable: metal simple substances such as lithium, sodium, potassium, calcium, magnesium, aluminum, indium, ruthenium, titanium, manganese, yttrium, silver, lead, tin, and chromium; or alloys of two or more of these, such as lithium-indium, sodium-potassium, magnesium-silver, aluminum-lithium, aluminum-magnesium, and magnesium-indium. Metal oxides such as indium-tin oxide (ITO) may also be used. Any of these electrode materials may be used alone or in a combination of two or more types. The cathode may be constituted of a single layer or a multiple layer.

As for the substrate used in the present invention, there are no particular limitations thereon. It is possible to use opaque substrates made of, for example, metal or ceramics, and transparent substrates made of, for example, glass, quartz and plastic sheets. A color filter film, a fluorescent color conversion filter film, or a dielectric reflecting film may also be used as the substrate to control luminescence light.

On the device produced, a protective layer or a sealing layer may be provided in order to prevent contact with oxygen or moisture. The protective layer may include diamond thin films; films of inorganic materials such as metal oxides and metal nitrides; films of high-molecular materials such as fluorine resins, polyparaxylene, polyethylene, silicone resins and polystyrene resins; and photocurable resins. The device may be covered with glass, a gas-impermeable film or metal, and packaged with a suitable sealing resin.

The organic luminescent device of the present invention may be so produced as to be connected with thin-film transistors (TFTs) fabricated on the substrate.

In regard to the direction in which light is taken out, the device may be of either bottom emission (a constitution in which light is taken out from the substrate side) or top emission (a constitution in which light is taken out from the opposite side of the substrate.)

EXAMPLES

The present invention is further described in greater detail by way of working examples. The present invention is by no means limited to these working examples.

Production Example 1

Production of Exemplary Compound No. 101

Exemplary Compound No. 101 of the present invention can be produced by, e.g., a process described below.

(1) Synthesis of 4-bromo-7,12-diphenylbenzo[k]fluoranthene 200 ml of xylene was added to a mixture of 5-bromoacenaphthylene (14.5 g, 62.8 mmol) and diphenylisobenzofuran (17.1 g, 63.3 mmol), and stirred for 5 hours under reflux of xylene. The mixture obtained was cooled to room temperature, and thereafter the solvent was distilled off, and 26 ml of trifluoroacetic anhydride and 260 ml of chloroform were added thereto and stirred for 1 hour under reflux. The mixture obtained was cooled to room temperature, and thereafter the solvent was distilled off, and then the resultant residue was purified by silica gel column chromatography (mobile phase; toluene:heptane=1:3) to produce as a yellow solid 16 g of 4-bromo-7,12-diphenylbenzo[k]fluoranthene.

(2) Synthesis of Exemplary Compound No. 101

In an atmosphere of nitrogen, the following compounds were dissolved in a mixed solvent of toluene (100 ml) and ethanol (50 ml). To the solution formed, an aqueous solution prepared by dissolving 0.95 g (2.90 mmol) of cesium carbonate in 15 ml of distilled water was added, and stirred at 50° C. for 30 minutes.

4-Bromo-7,12-diphenylbenzo[k]fluoranthene (0.7 g, 1.45 mmol)

2-(Fluoranthen-3-yl)-4,4,5,5-tetramethyl-[1,3,2]dioxabororane (0.48 g, 1.45 mmol).

To the mixture obtained, tetrakis(triphenylphos-phine)palladium (0.17 g, 1.45 mmol) was added, and heated and stirred for 5 hours on a silicone oil bath heated to 90° C. The mixture obtained was cooled to room temperature, followed by addition of water, toluene and ethyl acetate to separate an organic layer. The aqueous layer was further extracted (twice) with the mixed solvent of toluene and ethyl acetate, and the extract obtained was added to the organic layer solution having been separated first. This organic layer was washed with saturated brine, followed by drying with sodium sulfate. The solvent was distilled off, and then the resultant residue was purified by silica gel column chromatography (mobile phase; toluene:

heptane=1:3). The purified product was dried in vacuo at 120° C. to obtain as a pale-yellow solid 0.6 g of Exemplary Compound No. 101.

MALDI-TOF MS (matrix-assisted laser desorption/ionization time-of-flight mass spectrometry) ascertained 668.3 which was M+ of this compound.

Further, $^1$H-NMR measurement ascertained the structure of this compound (see FIG. 2).

The PL (photoluminescence) spectrum (excitation wavelength: 420 nm) of a toluene solution containing Exemplary Compound No. 101 in a concentration of $1\times10^{-5}$ mol/l was measured. A blue light emission spectrum was observed (see FIG. 3).

Production Examples 2 to 7

Production of Exemplary Compounds Nos. 102, 106-1, 110, 125, 130 & 131

The following Exemplary Compounds can be synthesized in the same manner as in Production Example 1 except that the following compounds are used, respectively, in place of the 4-bromo-7,12-diphenylbenzo[k]fluoranthene used in Production Example 1.

In Production Example 2, Exemplary Compound No. 102: 4-bromo-7,12-di(4-tert-butylphenyl)benzo[k]fluo-ranthene.

In Production Example 3, Exemplary Compound No. 106-1: 4-bromo-7,12-di(2-methylphenyl)benzo[k]fluo-ranthene.

In Production Example 4, Exemplary Compound No. 110: 4-bromo-7,12-di(4-fluorophenyl)benzo[k]fluo-ranthene.

In Production Example 5, Exemplary Compound No. 125: 4-bromo-7,12-di-tert-butylbenzo[k]fluoranthene.

In Production Example 6, Exemplary Compound No. 130: 4-bromo-7,12-diphenyl-3-methylbenzo[k]fluoranthene.

In Production Example 7, Exemplary Compound No. 131: 4-bromo-7,12-diphenyl-3-phenylbenzo[k]fluoranthene.

Production Example 8

Production of Exemplary Compound No. 118

Exemplary Compound No. 118 can be synthesized in the same manner as in Production Example 1 except that the following compound is used in place of the 2-(fluoranthen-3-yl)-4,4,5,5-tetramethyl-[1,3,2]dioxabororane used in Production Example 1. 2-(5,8-di-tertbutylfluoranthen-3-yl)-4,4,5,5-tetramethyl-[1,3,2]dioxabororane.

Production Examples 9 to 12

Production of Exemplary Compounds Nos. 201, 219, 223-2 & 229

The following Exemplary Compounds can be synthesized in the same manner as in Production Example 1 except that the following compounds are used, respectively, in place of the 2-(fluoranthen-3-yl)-4,4,5,5-tetramethyl-[1,3,2]dioxabororane used in Production Example 1.

In Production Example 9, Exemplary Compound No. 201: 2-(fluoranthen-8-yl)-4,4,5,5-tetramethyl-[1,3,2]dioxabororane.

In Production Example 10, Exemplary Compound No. 219: 2-(fluoranthen-7-yl)-4,4,5,5-tetramethyl-[1,3,2]dioxabororane.

In Production Example 11, Exemplary Compound No. 223-2: 2-(fluoranthen-1-yl)-4,4,5,5-tetramethyl-[1,3,2]dioxabororane.

In Production Example 12, Exemplary Compound No. 229: 2-(fluoranthen-2-yl)-4,4,5,5-tetramethyl-[1,3,2]dioxabororane.

Production Example 13

Production of Exemplary Compound No. H2-3

Exemplary Compound No. H2-3 of the present invention can be produced by, e.g., a process described below.

(1) Synthesis of intermediate (II):

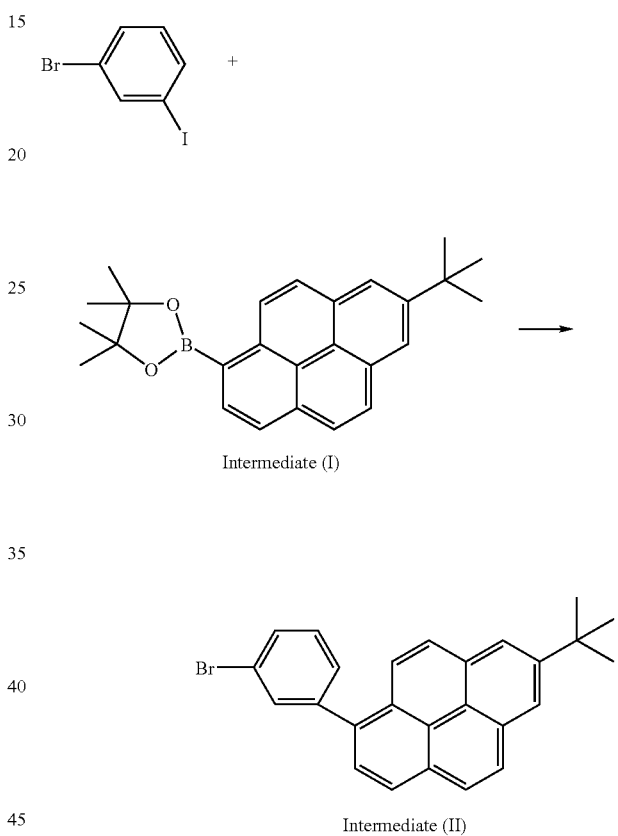

Intermediate (I)

Intermediate (II)

In an atmosphere of nitrogen, 2.58 g (9.11 mmol) of 1-bromo-3-iodobenzene and 3.5 g (9.11 mmol) of an intermediate (I) shown above were dissolved in a mixed solvent of toluene (100 ml) and ethanol (50 ml). To the solution formed, an aqueous solution prepared by dissolving 1.84 g (18.2 mmol) of sodium carbonate in 15 ml of distilled water was added, and stirred at 50° C. for 30 minutes. To the mixture obtained, tetrakis(triphenylphosphine)palladium (1.05 g, 0.911 mmol) was added, and heated and stirred for 4 hours on a silicone oil bath heated to 70° C. The mixture obtained was cooled to room temperature, followed by adding water, toluene and ethyl acetate to separate an organic layer. The aqueous layer was further extracted (twice) with the mixed solvent of toluene and ethyl acetate, and the extract obtained was added to the organic layer solution having been separated first. This organic layer was washed with saturated brine, followed by drying with sodium sulfate. The solvent was distilled off, and then the resultant residue was purified by silica gel column chromatography (mobile phase; toluene:heptane=1:4) to produce 2.9 g of an intermediate (II).

(2) Synthesis of Exemplary Compound H2-3:

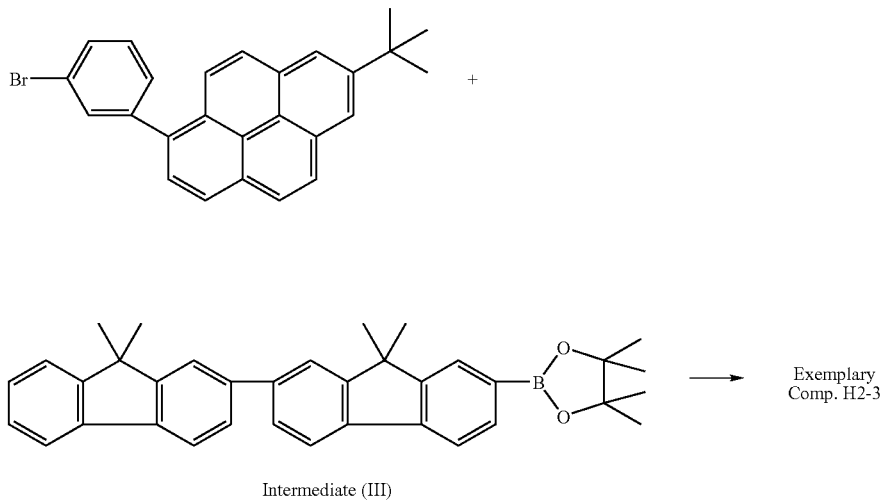

Intermediate (III)

In an atmosphere of nitrogen, 1.6 g (3.74 mmol) of the intermediate (II) and 1.91 g (3.74 mmol) of an intermediate (III) shown above were dissolved in a mixed solvent of toluene (100 ml) and ethanol (50 ml). To the solution formed, an aqueous solution prepared by dissolving 2.44 g (7.48 mmol) of cesium carbonate in 15 ml of distilled water was added, and stirred at 50° C. for 30 minutes. To the mixture obtained, tetrakis(triphenylphosphine)palladium (432 mg, 0.374 mmol) was added, and heated and stirred for 5 hours on a silicone oil bath heated to 90° C. The mixture obtained was cooled to room temperature, followed by adding water, toluene and ethyl acetate to separate an organic layer. The aqueous layer was further extracted (twice) with the mixed solvent of toluene and ethyl acetate, and the extract obtained was added to the organic layer solution having been separated first. This organic layer was washed with saturated brine, followed by drying with sodium sulfate. The solvent was distilled off, and then the resultant residue was purified by silica gel column chromatography (mobile phase; toluene: heptane=1:3) to obtain 2.1 g of Exemplary Compound H2-3.

MALDI-TOF MS (matrix-assisted laser desorption/ionization time-of-flight mass spectrometry) ascertained 718.4 which was $M^+$ of this compound.

Further, $^1$H-NMR measurement ascertained the structure of this compound (see FIG. 4).

Glass transition temperature of the compound in a glass state was measured with a DSC (differential scanning calorimeter) PYRIS 1, manufactured by Perkin-Elmer Corporation, at a heating rate of 10° C./min from room temperature and found to be 155° C.

Production Examples 14 to 20

Production of Exemplary Compounds Nos. H2-1, H2-2, H2-6, H2-13, H10-2, H11-2 & H12-1)

The following Exemplary Compounds can be synthesized in the same manner as in Production Example 13 except that the following compounds are used, respectively, in place of the intermediate (I) used in Production Example 13.

In Production Example 14, Exemplary Compound No. H2-1: 2-(pyren-1-yl)-4,4,5,5-tetramethyl-[1,3,2]dioxabororane.

In Production Example 15, Exemplary Compound No. H2-2: 2-(7-tert-butyl-3-methylpyren-1-yl)-4,4,5,5-tetramethyl-[1,3,2]dioxabororane.

In Production Example 16, Exemplary Compound No. H2-6: 2-(pyren-4-yl)-4,4,5,5-tetramethyl-[1,3,2]dioxabororane.

In Production Example 17, Exemplary Compound No. H2-13: 2-(7-iso-propylpyren-1-yl)-4,4,5,5-tetramethyl-[1,3,2]dioxabororane.

In Production Example 18, Exemplary Compound No. H10-2: 2-(10-phenylanthracen-9-yl)-4,4,5,5-tetramethyl-[1,3,2]dioxabororane.

In Production Example 19, Exemplary Compound No. H11-2: 2-(phenanthren-9-yl)-4,4,5,5-tetramethyl-[1,3,2]dioxabororane.

In Production Example 20, Exemplary Compound No. H12-1: 2-(chrysen-6-yl)-4,4,5,5-tetramethyl-[1,3,2]dioxabororane.

Production Example 21

Production of Exemplary Compounds No. H2-4

Exemplary Compound No. H2-4 can be synthesized in the same manner as in Production Example 13 except that 2-[2-(9',9'-diethylfluoren-2'-yl)-9,9-diethylfluoren-7-yl-4,4,5,5-tetramethyl-[1,3,2]dioxabororane is used in place of the intermediate (III) used in Production Example 13.

Production Example 22

Production of Exemplary Compounds No. H6-2

Exemplary Compound No. H6-2 can be synthesized in the same manner as in Production Example 13 except that 1-bromo-2-iodobenzene is used in place of the 1-bromo-3-iodobenzene) used in Production Example 13.

Production Example 23

Production of Exemplary Compound No. H4-2

Exemplary Compound No. H4-2 of the present invention can be produced by, e.g., a process described below.

Intermediate +
(III)

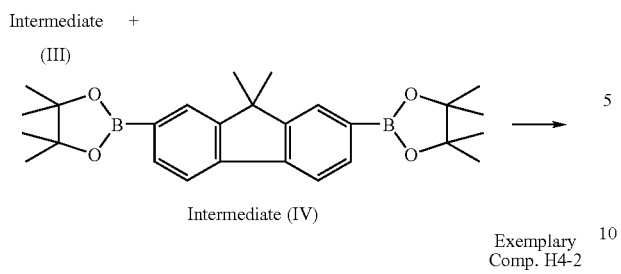

Intermediate (IV)

→ Exemplary Comp. H4-2

In an atmosphere of nitrogen, 2.28 g (5.52 mmol) of the intermediate (III) and 1.12 g (2.51 mol) of an intermediate (IV) shown above were dissolved in a mixed solvent of toluene (120 ml) and ethanol (60 ml). To the solution formed, an aqueous solution prepared by dissolving 3.6 g (11.0 mmol) of cesium carbonate in 15 ml of distilled water was added, and stirred at 50° C. for 30 minutes. To the mixture obtained, tetrakis(triphenylphosphine)palladium (580 mg, 0.502 mmol) was added, and heated and stirred for 5 hours on a silicone oil bath heated to 90° C. The mixture obtained was cooled to room temperature, followed by adding water, toluene and ethyl acetate to separate an organic layer. The aqueous layer was further extracted (twice) with the mixed solvent of toluene and ethyl acetate, and the extract obtained was added to the organic layer solution having been separated first. This organic layer was washed with saturated brine, followed by drying with sodium sulfate. The solvent was distilled off, and then the resultant residue was purified by silica gel column chromatography (mobile phase; toluene: heptane=1:3) to produce 1.4 g of Exemplary Compound H4-2.

MALDI-TOF MS (matrix-assisted laser desorption/ionization time-of-flight mass spectrometry) ascertained 858.4 which was $M^+$ of this compound.

Further, $^1$H-NMR measurement ascertained the structure of this compound (see FIG. 5).

Glass transition temperature of the compound in a glass state was measured with a DSC (differential scanning calorimeter) PYRIS 1, manufactured by Perkin-Elmer Corporation, at a heating rate of 10° C./min from room temperature and found to be 182° C.

Production Examples 24 to 30

Production of Exemplary Compounds Nos. H4-1, H4-4, H4-5, H4-8, H10-9, H11-8 & H12-3

The following Exemplary Compounds can be synthesized in the same manner as in Production Example 13 except that the following compounds are used, respectively, in place of the intermediate (III) used in Production Example 13.

In Production Example 24, Exemplary Compound No. H4-1: 2-(pyren-1-yl)-4,4,5,5-tetramethyl-[1,3,2]dioxabororane.

In Production Example 25, Exemplary Compound No. H4-4: 2-(7-tert-butyl-3-methylpyren-1-yl)-4,4,5,5-tetramethyl-[1,3,2]dioxabororane.

In Production Example 26, Exemplary Compound No. H4-5: 2-(pyren-4-yl)-4,4,5,5-tetramethyl-[1,3,2]dioxabororane.

In Production Example 27, Exemplary Compound No. H4-8: 2-(7-iso-propylpyren-1-yl)-4,4,5,5-tetramethyl-[1,3,2]dioxabororane.

In Production Example 28, Exemplary Compound No. H10-9: 2-(10-phenylanthracen-9-yl)-4,4,5,5-tetramethyl-[1,3,2]dioxabororane.

In Production Example 29, Exemplary Compound No. H11-8: 2-(phenanthren-9-yl)-4,4,5,5-tetramethyl-[1,3,2]dioxabororane.

In Production Example 30, Exemplary Compound No. H12-3: 2-(chrysen-6-yl)-4,4,5,5-tetramethyl-[1,3,2]dioxabororane.

Production Example 31

Production of Exemplary Compound No. H9-1

Exemplary Compound No. H9-1 of the present invention can be produced by, e.g., a process described below.

(1) Synthesis of intermediate (VI):

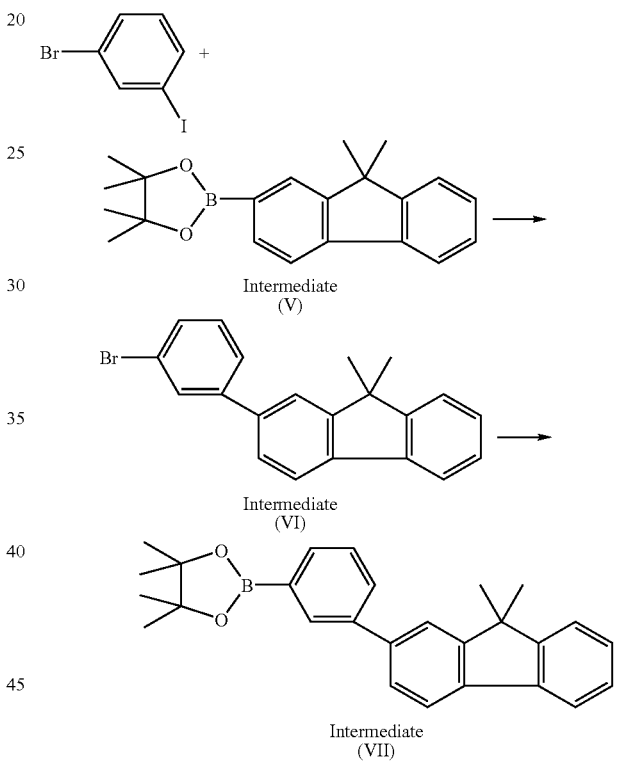

In an atmosphere of nitrogen, 3.08 g (10.9 mmol) of 1-bromo-3-iodobenzene and 3.5 g (10.9 mmol) of an intermediate (V) shown above were dissolved in a mixed solvent of toluene (120 ml) and ethanol (60 ml). To the solution formed, an aqueous solution prepared by dissolving 2.2 g (21.8 mmol) of sodium carbonate in 20 ml of distilled water was added, and stirred at 50° C. for 30 minutes. To the mixture obtained, tetrakis(triphenylphosphine)palladium (882 mg, 0.763 mmol) was added, and heated and stirred for 4 hours on a silicone oil bath heated to 90° C. The mixture obtained was cooled to room temperature, followed by adding water, toluene and ethyl acetate to separate an organic layer. The aqueous layer was further extracted (twice) with the mixed solvent of toluene and ethyl acetate, and the extract obtained was added to the organic layer solution having been separated first. This organic layer was washed with saturated brine, followed by drying with sodium sulfate. The solvent was distilled off, and then the resultant residue was purified by silica gel column chromatography (mobile phase; toluene: heptane=1:4) to obtain 3.3 g of an intermediate (VI).

(2) Synthesis of Exemplary Compound H9-1

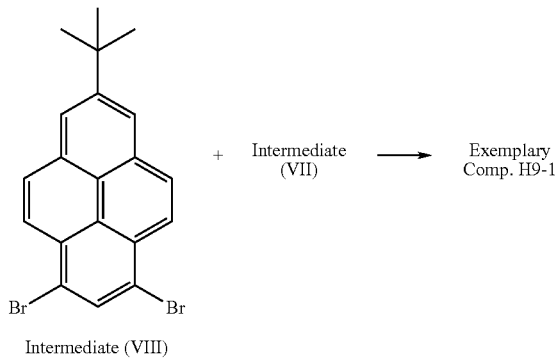

Intermediate (VIII)

In an atmosphere of nitrogen, 0.5 g (1.20 mmol) of an intermediate (VIII) derived from 7-tert-butylpyrene and 1 g (2.52 mmol) of the intermediate (VII) derived from the intermediate (VI) were dissolved in a mixed solvent of toluene (100 ml) and ethanol (50 ml). To the solution formed, an aqueous solution prepared by dissolving 1.64 g (5.04 mmol) of cesium carbonate in 15 ml of distilled water was added, and stirred at 50° C. for 30 minutes. To the mixture obtained, tetrakis(triphenylphosphine)palladium (222 mg, 0.192 mmol) was added, and heated and stirred for 5 hours on a silicone oil bath heated to 90° C. The mixture obtained was cooled to room temperature, followed by adding water, toluene and ethyl acetate to separate an organic layer. The aqueous layer was further extracted (twice) with the mixed solvent of toluene and ethyl acetate, and the extract obtained was added to the organic layer solution having been separated first. This organic layer was washed with saturated brine, followed by drying with sodium sulfate. The solvent was distilled off, and then the resultant residue was purified by silica gel column chromatography (mobile phase; toluene: heptane=1:3) to obtain 1.4 g of Exemplary Compound H9-1.

MALDI-TOF MS (matrix-assisted laser desorption/ionization time-of-flight mass spectrometry) ascertained 794.4 which was $M^+$ of this compound.

Further, $^1$H-NMR measurement ascertained the structure of this compound (see FIG. 6).

Glass transition temperature of the compound in a glass state was measured with a DSC (differential scanning calorimeter) PYRIS 1, manufactured by Perkin-Elmer Corporation, at a heating rate of 10° C./min from room temperature and found to be 161° C.

Production Example 32

Production of Exemplary Compounds No. H9-6

Exemplary Compound No. H9-6 can be synthesized in the same manner as in Production Example 31 except that 1-bromo-2-iodobenzene is used in place of 1-bromo-3-iodobenzene used in Production Example 31.

Production Example 33

Production of Exemplary Compound No. H14-3

Exemplary Compound No. H14-3 used in the present invention can be produced by, e.g., a process described below.

(1) Synthesis of Intermediate (IX):

An intermediate (IX) was produced in the same manner as in the intermediate (II) except that 1-bromo-4-iodobenzene was used in place of 1-bromo-3-iodobenzene.

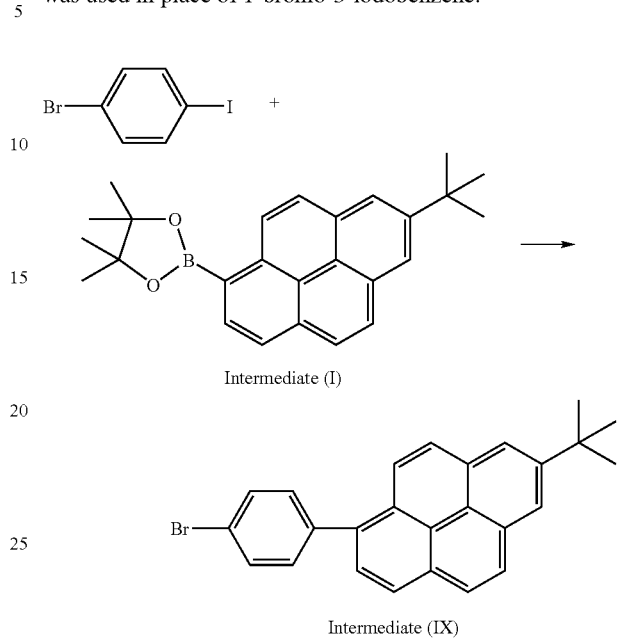

(2) Synthesis of Intermediate (X):

An intermediate (X) was produced in the same manner as in the intermediate (VII) except that 1-bromo-4-iodobenzene was used in place of the 1-bromo-3-iodobenzene).

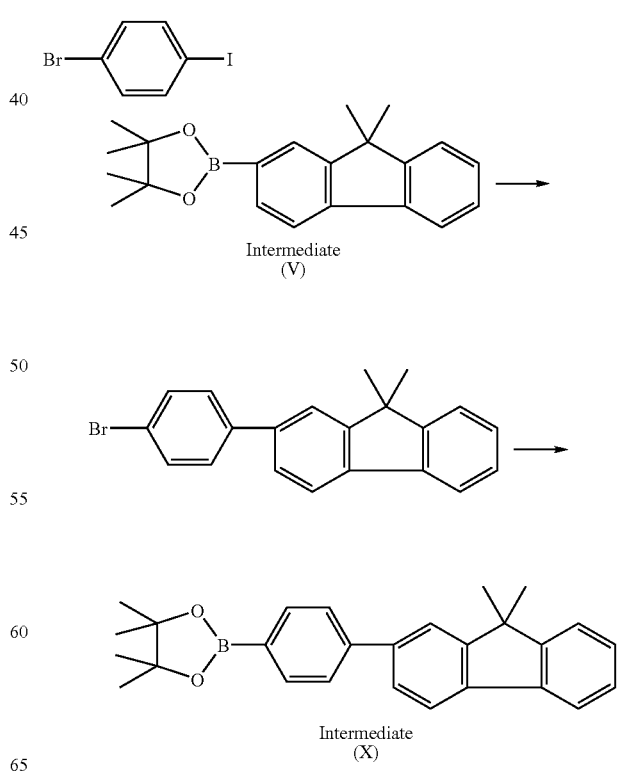

(3) Synthesis of Exemplary Compound H14-3:

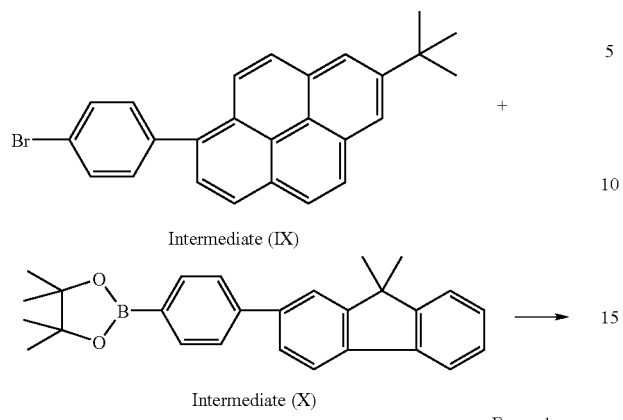

In an atmosphere of nitrogen, 2.33 g (5.65 mmol) of the intermediate (IX) and 2.28 g (5.76 mmol) of the intermediate (X) were dissolved in a mixed solvent of toluene (60 ml) and ethanol (30 ml). To the solution formed, an aqueous solution prepared by dissolving 1.51 g (14.2 mmol) of sodium carbonate in 15 ml of distilled water was added, and stirred at 50° C. for 30 minutes. To the mixture obtained, tetrakis(triphenylphosphine)palladium (339 mg, 0.29 mmol) was added, and heated and stirred for 4 hours on a silicone oil bath heated to 90° C. The mixture obtained was cooled to room temperature, followed by adding water, toluene and ethyl acetate to separate an organic layer. The aqueous layer was further extracted (twice) with the mixed solvent of toluene and ethyl acetate, and the extract obtained was added to the organic layer solution having been separated first. This organic layer was washed with saturated brine, followed by drying with sodium sulfate. The solvent was distilled off, and then the resultant residue was purified by silica gel column chromatography (mobile phase; toluene:heptane=1:3) to obtain 2.1 g of Exemplary Compound H14-3.

MALDI-TOF MS (matrix-assisted laser desorption/ionization time-of-flight mass spectrometry) ascertained 602.3 which was M$^+$ of this compound.

Further, $^1$H-NMR measurement ascertained the structure of this compound (see FIG. 7).

Glass transition temperature of the compound in a glass state was measured with a DSC (differential scanning calorimeter) PYRIS 1, manufactured by Perkin-Elmer Corporation, at a heating rate of 10° C./min from room temperature and found to be 123° C.

Example 1

An organic luminescent device having the structure shown in FIG. 1 was fabricated in the following way.

On a glass substrate as the substrate 1, an indium-tin oxide (ITO) film as the anode 2 was formed by sputtering in a layer thickness of 120 nm, and was used as a transparent conductive support substrate. This substrate was subjected to ultrasonic cleaning successively with acetone and isopropyl alcohol (IPA), and subsequently to cleaning with pure water, followed by drying. It was further subjected to UV/ozone cleaning, and was used as the transparent conductive support substrate.

Using as a hole transporting material Compound 1 represented by the following structural formula, its chloroform solution was prepared in a concentration of 0.1% by mass.

Compound 1

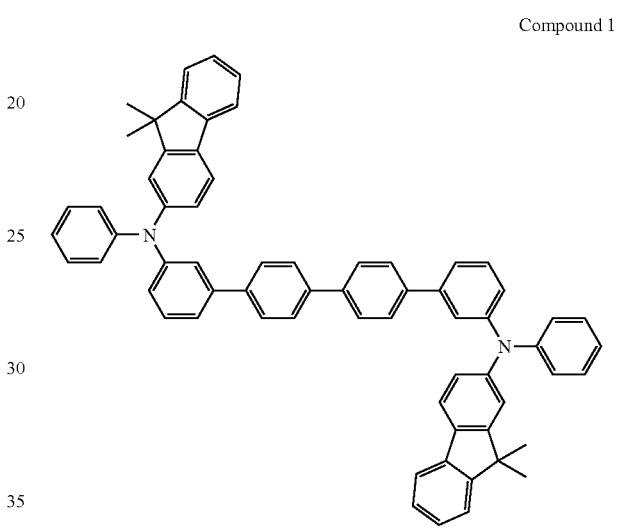

This solution was dropped on the above ITO electrode, and spin-coating was performed first at the number of revolutions of 500 rpm for 10 seconds and then at the number of revolutions of 1,000 rpm for 40 seconds to form a thin film. Thereafter, the film was dried for 10 minutes in a 80° C. vacuum oven to completely remove the solvent remaining in the thin film to form the hole transport layer 5.

Next, on the hole transport layer 5, Exemplary Compound No. 101 and Compound 2, as a second compound, represented by the following structural formula were vacuum-deposited together (mass ratio: 5:9) to form the luminescent layer 3 of 30 nm in thickness. The film formation by vacuum deposition was performed under conditions of a degree of vacuum of 1.0×10$^{-4}$ Pa and a rate of film formation of 0.1 nm/sec or more and 0.2 nm/sec or less.

Compound 2

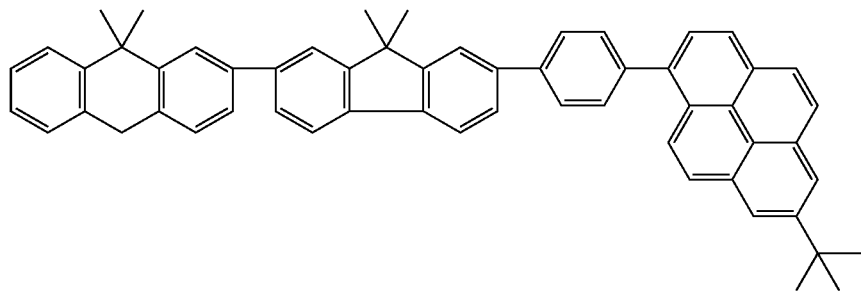

Further, as the electron transport layer 6, a 2,9-bis[2-(9,9'-dimethylfluorenyl)-1,10-phenanthroline film was formed by vacuum deposition in a layer thickness of 30 nm. The film formation by vacuum deposition was performed under conditions of a degree of vacuum of $1.0 \times 10^{-4}$ Pa and a rate of film formation of 0.1 nm/sec or more and 0.2 nm/sec or less.

Next, on the above organic layer, a lithium fluoride (LiF) film was formed by vacuum deposition in a layer thickness of 0.5 nm, and an aluminum film of 100 nm in thickness was further formed by vacuum deposition. An organic luminescent device (organic EL device) was fabricated having the aluminum-lithium film as an electron injection electrode (cathode 4). The film formation by vacuum deposition was performed under conditions of a degree of vacuum of $1.0 \times 10^{-4}$ Pa and a rate of film formation of 0.1 nm/sec for the lithium fluoride film and 0.5 nm/sec or more and 1.0 nm/sec or less for the aluminum film.

The organic EL device thus obtained was covered with a protecting glass plate in an atmosphere of dry air and sealed with an acrylic-resin adhesive so as not to cause device deterioration due to adsorption of moisture.

To the device thus obtained, a voltage was applied setting the ITO electrode (anode 2) as a positive pole and the Al—Li electrode (cathode 4) as a negative pole, where light emission of 6.4 cd/A in current efficiency was observed at an applied voltage of 4 V.

Compound 2 had an energy gap of 3.06 eV, and Exemplary Compound No. 101 had an energy gap of 2.81 eV. To examine the energy gaps, a method was used in which absorption spectra were measured with an ultraviolet-visible spectrophotometer Hitachi U-3010 and the values were calculated from absorption ends of the spectra.

Example 2

An organic luminescent device was fabricated in the same manner as in Example 1 except that Compound 3 represented by the following structural formula was used in place of Compound 1.

Compound 3

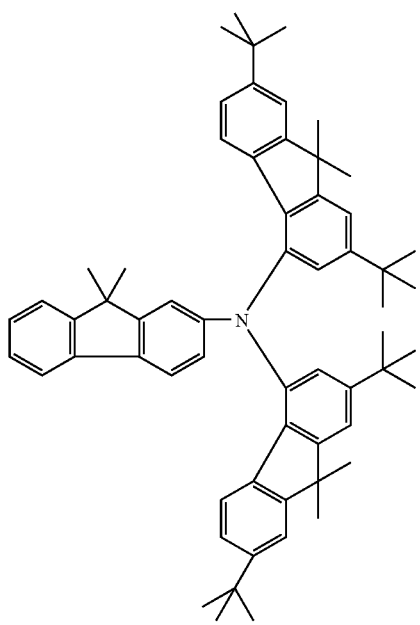

In the device of this Example, light emission of 7.6 cd/A in current efficiency was observed at an applied voltage of 4 V.

Example 3

An example is shown below in which a second compound represented by the general formula (4) is used.

An organic luminescent device was fabricated in the same manner as in Example 1 except that Compound 4 represented by the following structural formula was used in place of Compound 1, a film of the above Compound 3 was formed by vacuum deposition in a layer thickness of 15 nm to form the hole transport layer 5 and Exemplary Compound No. H2-3 was used as the second compound in place of the above Compound 2.

Exemplary Compound No. H2-3 had an energy gap of 3.18 eV and Exemplary Compound No. 101 had an energy gap of 2.81 eV. To examine the energy gaps, a method was used in which absorption spectra were measured with an ultraviolet-visible spectrophotometer Hitachi U-3010 and the values were calculated from absorption ends of the spectra.

Compound 4

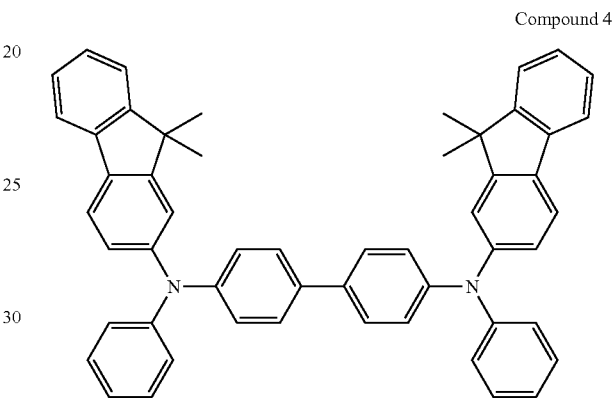

In the device of this Example, light emission of 6.8 cd/A in current efficiency was observed at an applied voltage of 4 V.

The voltage was further applied to this device for 100 hours in an atmosphere of nitrogen to ascertain that good light emission continued.

Example 4

An example is shown below in which a second compound represented by the general formula (4) is used.

An organic luminescent device was fabricated in the same manner as in Example 3 except that Exemplary Compound No. H14-3 was used as the second compound in place of the above Compound 2.

Exemplary Compound No. H14-3 had an energy gap of 3.03 eV. To examine the energy gap, a method was used in which an absorption spectrum was measured with an ultraviolet-visible spectrophotometer Hitachi U-3010 and the value was calculated from an absorption end of the spectrum.

In the device of this Example, light emission of 8.3 cd/A in current efficiency was observed at an applied voltage of 4 V.

The voltage was further applied to this device for 100 hours in an atmosphere of nitrogen to ascertain that good light emission continued.

Example 5

An example is shown below in which a second compound represented by the general formula (4) is used.

An organic luminescent device was fabricated in the same manner as in Example 3 except that Compound 5 represented by the following structural formula was used as the second compound in place of the above Compound 2.

Compound 5 had an energy gap of 3.06 eV. To examine the energy gap, a method was used in which an absorption spectrum was measured with an ultraviolet-visible spectrophotometer Hitachi U-3010 and the value was calculated from an absorption end of the spectrum.

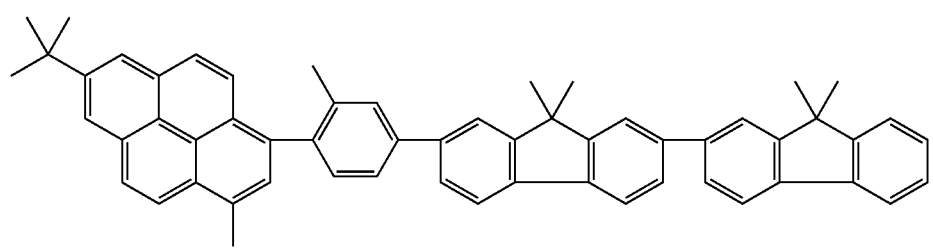

Compound 5

In the device of this Example, light emission of 7.7 cd/A in current efficiency was observed at an applied voltage of 4 V.

The voltage was further applied to this device for 100 hours in an atmosphere of nitrogen to ascertain that good light emission continued.

Example 6

An organic luminescent device was fabricated in the same manner as in Example 3 except that Compound 6 represented by the following structural formula was used as the second compound in place of the above Compound 2.

Compound 6 had an energy gap of 2.99 eV. To examine the energy gap, a method was used in which an absorption spectrum was measured with an ultraviolet-visible spectrophotometer Hitachi U-3010 and the value was calculated from an absorption end of the spectrum.

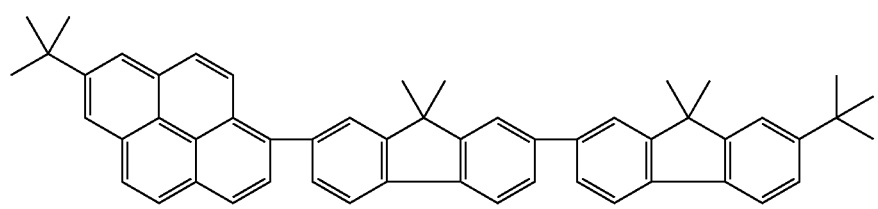

Compound 6

In the device of this Example, light emission of 5.2 cd/A in current efficiency was observed at an applied voltage of 4 V.

The voltage was further applied to this device for 100 hours in an atmosphere of nitrogen to ascertain that good light emission continued.

Example 7

An organic luminescent device was fabricated in the same manner as in Example 3 except that Compound 7 represented by the following structural formula was used as the second compound in place of the above Compound 2.

Compound 7 had an energy gap of 2.99 eV. To examine the energy gap, a method was used in which an absorption spectrum was measured with an ultraviolet-visible spectrophotometer Hitachi U-3010 and the value was calculated from an absorption end of the spectrum.

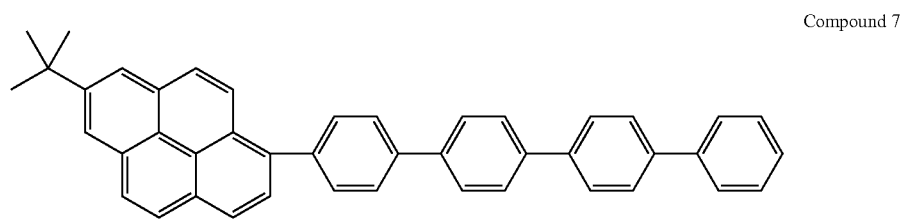

Compound 7

In the device of this Example, light emission of 7.2 cd/A in current efficiency was observed at an applied voltage of 4 V.

The voltage was further applied to this device for 100 hours in an atmosphere of nitrogen to ascertain that good light emission continued.

Example 8

An organic luminescent device was fabricated in the same manner as in Example 3 except that Compound 8 represented by the following structural formula was used as the second compound in place of the above Compound 2.

Compound 8 had an energy gap of 3.12 eV. To examine the energy gap, a method was used in which an absorption spectrum was measured with an ultraviolet-visible spectrophotometer Hitachi U-3010 and the value was calculated from an absorption end of the spectrum.

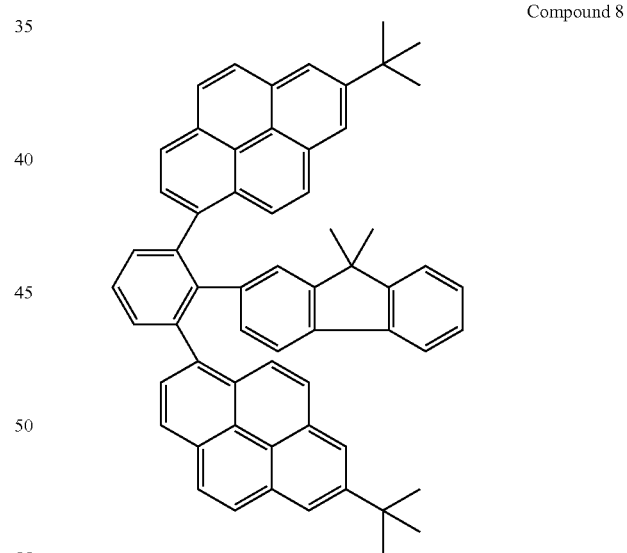

Compound 8

In the device of this Example, light emission of 6.8 cd/A in current efficiency was observed at an applied voltage of 4 V.

The voltage was further applied to this device for 100 hours in an atmosphere of nitrogen to ascertain that good light emission continued.

Example 9

An organic luminescent device was fabricated in the same manner as in Example 3 except that Compound 9 represented by the following structural formula was used as the second compound in place of the above Compound 2.

Compound 9 had an energy gap of 2.88 eV. To examine the energy gap, a method was used in which an absorption spectrum was measured with an ultraviolet-visible spectrophotometer Hitachi U-3010 and the value was calculated from an absorption end of the spectrum.

Compound 9

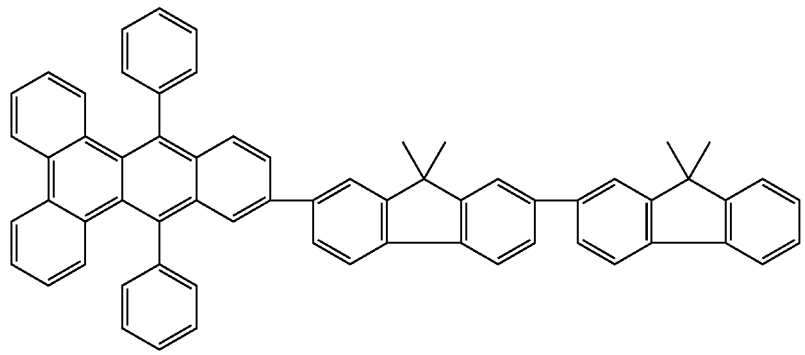

In the device of this Example, light emission of 6.4 cd/A in current efficiency was observed at an applied voltage of 4 V.

The voltage was further applied to this device for 100 hours in an atmosphere of nitrogen to ascertain that good light emission continued.

Example 10

An organic luminescent device was fabricated in the same manner as in Example 3 except that Compound 10 represented by the following structural formula was used as the second compound in place of the above Compound 2.

Compound 10 had an energy gap of 2.99 eV. To examine the energy gap, a method was used in which an absorption spectrum was measured with an ultraviolet-visible spectrophotometer Hitachi U-3010 and the value was calculated from an absorption end of the spectrum.

Compound 10

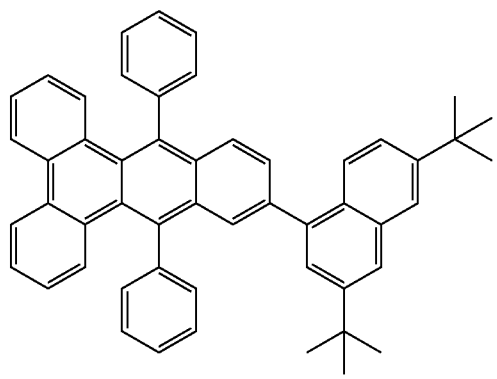

In the device of this Example, light emission of 4.4 cd/A in current efficiency was observed at an applied voltage of 4 V.

The voltage was further applied to this device for 100 hours in an atmosphere of nitrogen to ascertain that good light emission continued.

The present invention is not limited to the above embodiments and various changes and modifications can be made within the spirit and scope of the present invention. Therefore to apprise the public of the scope of the present invention, the following claims are made.

This application claims priorities from Japanese Patent Applications No. 2006-213606, filed Aug. 4, 2006, and No. 2007-120565, filed May 1, 2007, which are hereby incorporated by reference herein.

The invention claimed is:

1. An organic luminescent device which comprises an anode and a cathode at least one of which is transparent or semitransparent, and a layer containing an organic compound, held between a pair of electrodes consisting of the anode and the cathode, wherein;

the layer containing an organic compound contains a benzo[k]fluoranthene compound represented by the following general formula (1):

[1]

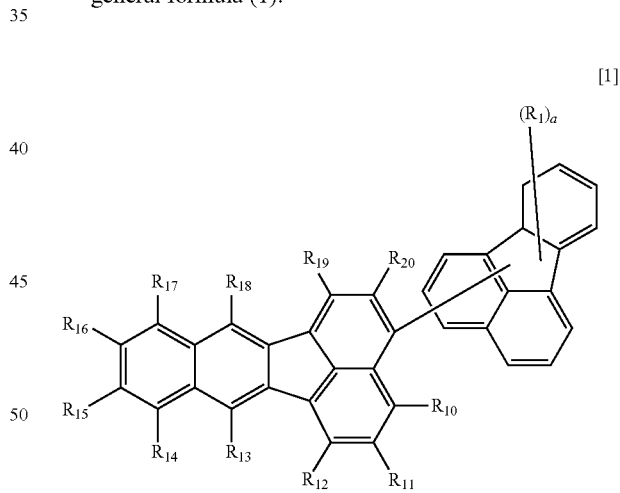

wherein $R_1$ is a group selected from the group consisting of a substituted or unsubstituted alkyl group, a substituted or unsubstituted aralkyl group and a substituted or unsubstituted heterocyclic ring group, and $R_1$'s may be the same or different; $R_{10}$ is a hydrogen atom; $R_{11}$ to $R_{20}$ are each independently a group selected from the group consisting of a hydrogen atom, a halogen atom, a substituted or unsubstituted alkyl group, a substituted or unsubstituted aralkyl group, a substituted or unsubstituted phenyl group, a substituted or unsubstituted condensed bicyclic aromatic group and a substituted or unsubstituted heterocyclic group; and a is an integer of 0 or more and 9 or less.

2. The organic luminescent device according to claim 1, wherein the benzo[k]fluoranthene compound is represented by the following general formula (2):

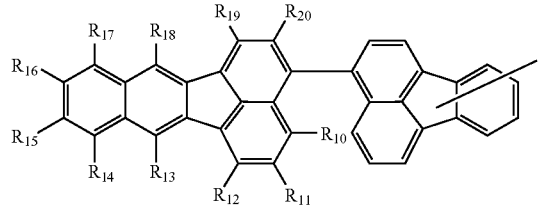

[2]

wherein $R_1$, $R_{10}$ to $R_{20}$ and a are as defined in the general formulas (1).

3. The organic luminescent device according to claim 1, wherein the benzo[k]fluoranthene compound is represented by the following general formula (3):

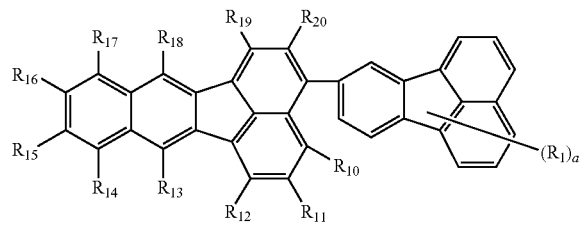

[3]

wherein $R_1$ is a group selected from the group consisting of a substituted or unsubstituted alkyl group, a substituted or unsubstituted aralkyl group and a substituted or unsubstituted heterocyclic group, and $R_1$'s may be the same or different; $R_{10}$ is a hydrogen atom; $R_{11}$ to $R_{20}$ are each independently a group selected from the group consisting of a hydrogen atom, a halogen atom, a substituted or unsubstituted alkyl group, a substituted or unsubstituted aralkyl group, a substituted or unsubstituted alkoxyl group, a substituted or unsubstituted phenyl group, a substituted or unsubstituted condensed bicyclic aromatic group and a substituted or unsubstituted heterocyclic group; and a is an integer of 0 or more and 9 or less.

4. The organic luminescent device according to claim 1, wherein the layer containing the benzo[k]fluoranthene compound further contains a second compound having a larger energy gap than the benzo[k]fluoranthene compound.

5. The organic luminescent device according to claim 4, wherein the second compound is represented by the following general formula (4):

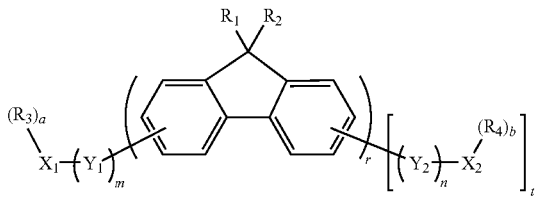

[4]

wherein $R_1$ and $R_2$ are each independently a group selected from the group consisting of a hydrogen atom, a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic group, $R_1$'s may be the same or different, $R_2$'s may be the same or different; $R_3$ and $R_4$ are each independently a group selected from the group consisting of a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic group, $R_3$'s may be the same or different, $R_4$'s may be the same or different; $X_1$ and $X_2$ are each independently a substituted or unsubstituted aryl group or a substituted or unsubstituted heterocyclic ring group; a and b are each independently an integer of 0 to 3; $Y_1$ and $Y_2$ are each independently a substituted or unsubstituted phenylene group, $Y_1$'s may be the same or different, $Y_2$'s may be the same or different; m and n are each independently an integer of 1 to 3; t is 0 or 1, and, when t is 0, the terminal fluorenyl group may be substituted, at its position where it is substituted with $Y_2$, with a group selected from the group consisting of a halogen atom, a substituted or unsubstituted alkyl group, a substituted or unsubstituted aralkyl group, a substituted or unsubstituted alkoxyl group and a substituted or unsubstituted phenyl group; and r is an integer of 1 to 5.

6. The organic luminescent device according to claim 5, wherein the second compound is a compound wherein $Y_1$ and $Y_2$ of the general formula (4) are each independently a group represented by the following general formulas (5) or (6):

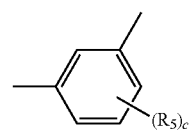

[5]

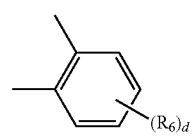

[6]

wherein $R_5$ and $R_6$ are each independently a group selected from the group consisting of a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic group, $R_5$'s may be the same or different, and $R_6$'s may be the same or different; and c and d are each an integer of 0 to 4.

7. The organic luminescent device according to claim 5, wherein the second compound is a compound wherein $Y_1$ and $Y_2$ of the general formula (4) are each independently a group represented by the following general formula (7):

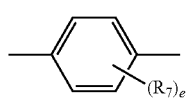

[7]

wherein $R_7$ is a group selected from the group consisting of a halogen atom, a substituted or unsubstituted alkyl group, a substituted or unsubstituted aralkyl group, a substituted or unsubstituted alkoxyl group, a substituted or unsubstituted aryl group and a substituted or unsubstituted heterocyclic group, and $R_7$'s may be the same or different; and e is an integer of 0 to 4.

8. The organic luminescent device according to claim 6, wherein the second compound is represented by the following general formula (8):

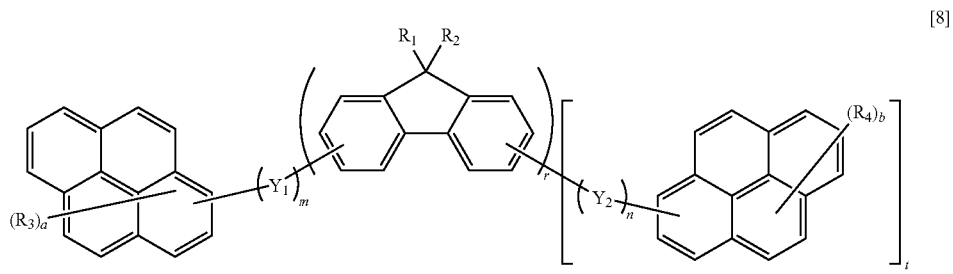

[8]

wherein $R_1$ to $R_4$, $Y_1$, $Y_2$, a, b, m, n, r and t are as defined in the general formula (4).

9. The organic luminescent device according to claim 8, wherein the second compound is represented by the following general formula (9):

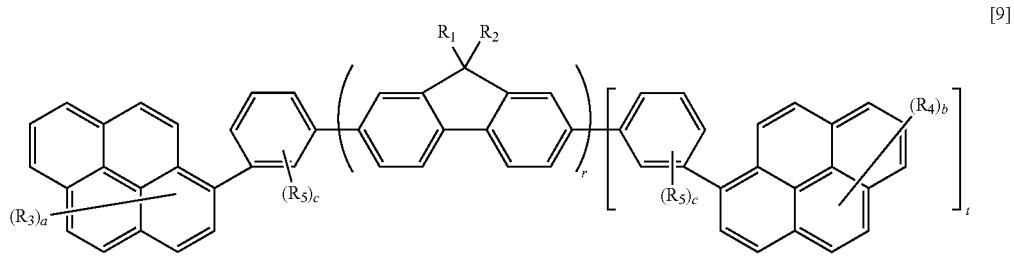

[9]

wherein $R_1$ to $R_4$, a, b and t are as defined in the general formula (4) and $R_5$ and c are as defined in the general formula (5).

10. The organic luminescent device according to claim 8, wherein the second compound is represented by the following general formula (10):

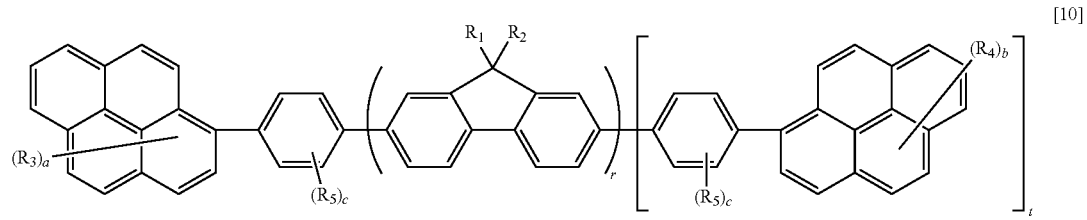

wherein $R_1$ to $R_4$, a, b and t are as defined in the general formula (4) and $R_5$ and c are as defined in the general formula (5).

11. The organic luminescent device according to claim 1, wherein the layer containing the benzo[k]fluoranthene compound is at least one layer having a luminescent region.

12. The organic luminescent device according to claim 11, wherein said at least one layer having a luminescent region is a luminescent layer.

13. A benzo[k]fluoranthene compound represented by the following general formula (3):

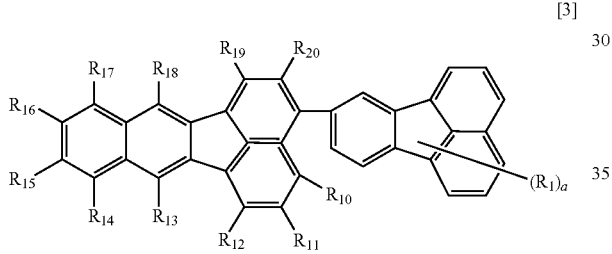

wherein $R_1$ is a group selected from the group consisting of a substituted or unsubstituted alkyl group, a substituted or unsubstituted aralkyl group and a substituted or unsubstituted heterocyclic group, and $R_1$'s may be the same or different; $R_{10}$ is a hydrogen atom; $R_{11}$ to $R_{20}$ are each independently a group selected from the group consisting of a hydrogen atom, a halogen atom, a substituted or unsubstituted alkyl group, a substituted or unsubstituted aralkyl group, a substituted or unsubstituted alkoxyl group, a substituted or unsubstituted phenyl group, a substituted or unsubstituted condensed bicyclic aromatic group and a substituted or unsubstituted heterocyclic group; and a is an integer of 0 or more to 9 or less.

* * * * *